United States Patent
Gatanaga et al.

(10) Patent No.: US 6,569,664 B1
(45) Date of Patent: May 27, 2003

(54) NATIVE TNF RECEPTOR RELEASING ENZYME

(75) Inventors: Tetsuya Gatanaga, Irvine, CA (US); Gale A. Granger, Laguna Beach, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 08/964,747

(22) Filed: Nov. 5, 1997

Related U.S. Application Data

(60) Provisional application No. 60/030,761, filed on Nov. 6, 1996.

(51) Int. Cl.[7] ............................. C12N 9/64; C07K 1/14; C07K 1/18; C07K 1/26
(52) U.S. Cl. ..................... 435/226; 435/68.1; 530/412; 530/416; 530/417
(58) Field of Search ......................... 435/226; 530/412, 530/413, 417; 424/94.63

(56) References Cited

U.S. PATENT DOCUMENTS

| | | | |
|---|---|---|---|
| 4,340,586 A | 7/1982 | Bekierkunst et al. | 424/282.1 |
| 4,695,590 A | 9/1987 | Lippman | 514/724 |
| 4,959,353 A | 9/1990 | Brown et al. | 514/12 |
| 4,983,586 A | 1/1991 | Bodor | 514/58 |

(List continued on next page.)

FOREIGN PATENT DOCUMENTS

| | | |
|---|---|---|
| EP | 211 077 | 5/1993 |
| EP | 568 925 | 11/1993 |
| EP | 623 676 | 11/1994 |
| EP | 657 536 | 6/1995 |
| EP | 418 014 | 12/1995 |
| WO | WO 90/11287 | 10/1990 |
| WO | WO 90/14363 | 11/1990 |
| WO | WO 91/04014 | 4/1991 |
| WO | WO 93/07286 | 4/1993 |
| WO | WO 93/20186 | 10/1993 |
| WO | WO 94/22309 | 10/1994 |
| WO | WO 95/09913 | 4/1995 |
| WO | WO 95/13365 | 5/1995 |
| WO | WO 95/31544 | 11/1995 |
| WO | WO 95/33051 | 12/1995 |
| WO | WO 96/01642 | 1/1996 |

OTHER PUBLICATIONS

Katsura, K., et al., 1996, Biochemical and Biophysical Research Communications, vol. 222, Identification of the proteolytic enzyme which cleaves human p75 TNF receptor in vitro, pp. 298–302.*

Solorzano, C.C., et al., 1997, The Journal of Immunology, vol. 97, "Involvement of 26–kDa cell–associated TNF–alpha in experimental hepatitis and exacerbation of liver injury with a matrix metalloproteinase inhibitor", pp. 414–419.*

Wu, A.J., et al., 1997, Journal of Cellular Physiology, vol. 171, "Modulation of MMP–2 (gelatinase A) and MMP–9 (gelatinase B) by interferon–gamma in a human salifary gland cell line", pp. 117–124.*

(List continued on next page.)

Primary Examiner—Ponnathapu Achutamurthy
Assistant Examiner—William W. Moore
(74) Attorney, Agent, or Firm—Bozicevic, Field and Francis LLP; Carol L. Francis

(57) ABSTRACT

The present invention relates to methods of regulating TNF activity indirectly by regulating the activity or concentration of TNF receptor releasing enzyme (TRRE). Preferably, the TRRE activity is regulated local to the site of the condition to be treated. In the case of diseases associated with elevated levels of TNF, such as rheumatoid arthritis, TRRE is administered to the site of inflammation in an amount sufficient to decrease the local levels of TNF. In the case of diseases, such as cancer, that benefit from increased levels of TNF, the level of TRRE is decreased at the disease site.

28 Claims, 13 Drawing Sheets

U.S. PATENT DOCUMENTS

| | | | | |
|---|---|---|---|---|
| 5,001,061 A | * | 3/1991 | Rolfe et al. | 435/172.3 |
| 5,002,935 A | | 3/1991 | Bodor | 514/58 |
| 5,017,566 A | | 5/1991 | Bodor | 514/58 |
| 5,130,298 A | | 7/1992 | Cini et al. | 514/12 |
| 5,140,043 A | | 8/1992 | Darr et al. | 514/474 |
| 5,153,179 A | | 10/1992 | Eibl | 514/34 |
| 5,192,537 A | | 3/1993 | Osband | 424/85.2 |
| 5,268,384 A | | 12/1993 | Galardy | 514/419 |
| 5,270,326 A | | 12/1993 | Galardy et al. | 514/323 |
| 5,376,682 A | | 12/1994 | Naiki et al. | 514/473 |
| 5,395,760 A | | 3/1995 | Smith et al. | 435/365 |
| 5,643,740 A | | 7/1997 | Billing et al. | 435/7.23 |
| 5,665,859 A | * | 9/1997 | Wallach et al. | 530/328 |
| 5,766,917 A | * | 6/1998 | Wallach et al. | 435/219 |
| 5,853,977 A | * | 12/1998 | Dalie et al. | 435/4 |
| 6,022,948 A | * | 2/2000 | Goldberg | 530/326 |
| 6,068,838 A | | 5/2000 | Furlan et al. | |
| 6,090,605 A | | 6/2000 | Elbien | |
| 6,191,258 B1 | | 2/2001 | Lamb et al. | |
| 6,261,556 B1 | | 7/2001 | Weinrich et al. | |
| 6,326,151 B1 | | 12/2001 | Katze et al. | |

OTHER PUBLICATIONS

Gallea–Robache, S., et al., 1997, Cytokine, vol. 9, "A metalloproteinase inhibitor blocks the shedding of soluble cytokine receptors and processing of transmembrane cytokine precursors in human monocyte cells", pp. 340–346.*

Azuma, M., et al., 1997, Laboratory Investigation, vol. 77, "Role of cytokines in the destruction of acinar structure in Sjogren's syndrome salivary glands", pp. 269–280.*

Smith, M.R., et al., 1997, Cytokine, vol. 9, "TIMP–3 induces cell death by stabilizing TNF–alpha receptors on the surface of human colon carcinoma cells", pp. 770–780.*

Black, R. A., et al., 1991, "A metalloprotease disintegrin that releases tumour–necrosis factor–alpha from cells", Nature, vol. 385, pp. 729–733.*

Moss, M. L., et al., 1991, "Cloning of a disintegrin metalloprotease that processes precursor tumour–necrosis factor–alpha", Nature, vol. 385, pp. 733–736.*

Peschon, J. J., et al., 1998, "An essential role for ectodomain shedding in mammalian development", Science, vol. 282, pp. 1281–1284.*

Park, M., et al., 1996, "TNF–receptor releasing enzyme is secreted by PMA–stimulated THP–1 cell line", The FASEB Journal, vol. 10, No. 6, pp. A1484, Abstract No. 2789.*

Gatanaga, T., et al, 1996, TNF–receptor releasing enzyme is secreted by PMA–stimulated THP–1 cell line, The European Cytokine Network, vol. 7, No. 2, p. 166, Abstract No. 14.*

Schlondorff, J., et al., 2001 "Biochemical and pharmacological criteria define two shedding activities for TRANCE/OPGL that are distinct from the Tumor Necrosis Factor convertase", The Journal of Bioogical Chemistry, vol. 276, pp. 14665–14674.*

Suganama, T., 2001, "Partial amino acid sequences of human TNF receptor releasing enzyme", Journal of the National Defense Medical College, vol. 26, pp. 11–21.*

Abraham et al., "p55 tumor necrosis factor fusion protein in the treatment of patients with severe sepsis and septic shock" (1997) *JAMA* 277:1531–1538.

Aderka et al., "Increased serum levels of soluble receptors for tumor necrosis factor in cancer patients" (1991) *Cancer Res.* 51:5602–5607.

Aderka et al., "Stabilization of the bioactivity of tumor necrosis factor by its soluble receptors" (1992) *J. Exp. Med.* 175:323–329.

Aderka et al., "Variation in serum levels of the soluble TNF receptors among healthy individuals" (1992) *Lymphokine Cytokine Res.* 11:157–159.

Alderson et al., "Regulation of human monocyte cell–surface and soluble CD23 (FCεRII) by granulocyte–macrophage colony–stimulating factor and IL–3" (1992) *J. Immunol.* 149:1252–1257.

Alexander et al., "Extracellular matrix degradation" (1991) *Cell Biology of Extracellular Matrix,* ed. Hay, Plenum Press, New York, Chapter 8, pp. 255–302.

Arbós et al., "Effects of tumour necrosis factor–α (cachectin) on glucose metabolism in the rat" (1992) *Mol. Cell. Biochem.* 112:53–59.

Argilés et al., "The metabolic environment of cancer" (1988) *Mol. Cell. Biochem.* 81:3–17.

Argilés et al., "Journey from cachexia to obesity by TNF" (1997) *FASEB J.* 11:743–751.

Armitage,R., "Tumor necrosis factor receptor superfamily members and their ligands" (1994) *Curr. Opin. Immunol.* 6:407–413.

Ashkenazi et al., "Protection against endotoxic shock by a tumor necrosis factor receptor immunoadhesin" (1991) *Proc. Natl. Acad. Sci. USA* 88:10535–10539.

Baba et al., "Intracarotid infusion of leukotriene $C_4$ selectively increased blood–brain barrier permeability after focal ischemia in rats" (1991) *J. Cereb. Blood Flow Metab.* 11:638–643.

Banner et al., "Crystal structure of the soluble human 55 kd receptor–human TNFβ complex: Implications for TNF receptor activation" (1993) *Cell* 73:431–445.

Baran et al., "Characterization of the soluble murine IL–2R and estimation of its affinity for IL–2" (1988) *J. Immunol.* 141:539–546.

Bauditz et al., "Treatment with tumour necrosis factor inhibitor oxpentifylline does not improve corticosteroid dependent chronic active Crohn's disease" (1997) *Gut* 40:470–474.

Baum et al., "Molecular characterization of murine and human OX40/OX40 ligand systems: identification of a human OX40 ligand as the HTLV–1 regulated protein gp34" (1994) *EMBO J.* 13:3992–4001.

Beretz et al., "Modulation by cytokines of leukocyte–endothelial cell interactions, implications for thrombosis" (1990) *Biorheology* 27:455–460.

Bermudez et al., "Effect of stress–related hormones on macrophage receptors and response to tumor necrosis factor" (1990) *Lymphokine Res.* 9:137–145.

Beutler et al., "Passive immunization against cachectin/tumor necrosis factor protects mice from lethal effect of endotoxin" (1985) *Science* 229:869–871.

Bianchi et al., "Increased Brown adipose tissue activity in children with malignant disease" (1989) *Horm. Metab. Res.* 21:640–641.

Bickel et al., "Pharmacologic effects in vivo in brain by vector–mediated peptide drug delivery" (1993) *Proc. Natl. Acad. Sci. USA* 90:2618–2622.

Birkedal–Hansen et al., "Matrix metalloproteinases: A review" (1993) *Crit. Rev. Oral Biol. Med.* 4:197–250.

Björnberg et al., "Metalloproteases and serineproteases are involved in the cleavage of the two tumour necrosis factor (TNF) receptors to soluble forms in the myeloid cell lines U–937 and THP–1" (1995) *Scand. J. Immunol.* 42:418–424.

Bogdan et al., "Macrophage deactivation by interleukin 10" (1991) *J. Exp. Med.* 174:1549–1555.

Boillot et al., "Myocardial and vascular adrenergic alterations in a rat model of endotoxin shock: Reversal by an anti–tumor necrosis factor–α monoclonal antibody" (1997) *Crit Care Medicine* 25:504–511.

Bonfil et al., "Invasive and metastatic potential of a v–Ha–ras transformed human bronchial epithelial cell line" (1989) *J. Natl. Cancer Inst.* 81:587–594.

Brennan et al., "Reduction of serum matrix metalloproteinase 1 and matrix metalloproteinase 3 in rheumatoid arthritis patients following anti–tumour necrosis factor–α (cA2) therapy" (1997) *Br. J. Rheumatology* 36:643–650.

Brockhaus et al., "Identification of two types of tumor necrosis factor receptors on human cell lines by monoclonal antibodies" (1990) *Proc. Natl. Acad. Sci. USA* 87:3127–3131.

Brown, "Matrix metalloproteinase inhibitors: A novel class of anticancer agents" (1995) *Advan. Enzyme Regul.* 35:293–301.

Buck et al., "Tumor necrosis factor–α inhibits collagen α1(1) gene expression and wound healing in a murine model of cachexia" (1996) *Am. J. Pathol.* 149:195–204.

Calvano et al., "Monocyte tumor necrosis factor receptor levels as a predictor of risk in human sepsis" (1996) *Arch. Surg.* 131:434–437.

Chin et al., "Stromelysin, a connective tissue–degrading metalloendopeptidase secreted by stimulated rabbit synovial fibroblasts in parallel with collagenase" (1985) *J. Biol. Chem.* 260:12367–12376.

Chitambar, "Shedding of transferrin receptor from rat reticulocytes during maturation in vitro: Soluble transferrin receptor is derived from receptor shed in vesicles" (1991) *Blood* 78:2444–2450.

Colditz, "Epidemiology of breast cancer" (1993) *Cancer Suppl.* 71:1480–1489.

Colotta et al., "Interleukin–1 type II receptor: A decoy for IL–1 that is regulated by IL–4" (1994) *Science* 261:472–475.

Conway et al., "Inhibition of cartilage and bone destruction in adjuvant arthritis in the rat by a matrix metalloproteinase inhibitor" (1995) *J. Exp. Med.* 182:449–457.

Corcoran et al., "Characterization of ligand binding by the human p55 tumour–necrosis–factor receptor" (1994) Eur. J. Biochem. 223:831–840.

Cornelius et al., "Regulation of lipoprotein lipase mRNA content in 3T3–L1 cells by tumour necrosis factor" (1988) *Biochem. J.* 249:765–769.

Cosman, "A family of ligands for the TNF receptor superfamily" (1994) *Stem Cells* (Dayt.) 12:440–455.

Costelli et al., "Tumor necrosis factor–α mediates changes in tissue protein turnover in a rat cancer cachexia model" (1993) *J. Clin. Invest.* 92:2783–2789.

Crowe et al., "A metalloprotease inhibitor blocks shedding of the 80–kD TNF receptor and TNF processing in T lymphocytres" (1995) *J. Exp. Med.* 181:1205–1210.

Dansette et al., "Continuous fluorometric assay of epoxide hydrase activity" (1979) *Anal. Biochem.* 97:340–345.

Davies et al., "A synthetic matrix metalloproteinase inhibitor decreases tumor burden and prolongs survival of mice bearing human ovarian carcinoma xenografts" (1993)*Cancer Res.* 53:2087–2091.

de Wall Malefyt et al., "Interleukin 10(IL–10) inhibits cytokine synthesis by human monocytes: An autoregulatory role of IL–10 produced by monocytes" (1991) *J. Exp. Med.* 174:1209–1220.

Dean et al., "Evidence for metalloproteinase and metalloproteinase inhibitor imbalance in human osteoarthritic cartilage" (1989) *J. Clin. Invest.* 84:678–685.

Dembic et al. "Two human TNF receptors have similar extracellular, but distinct intracellular, domain sequences" (1990) *Cytokine* 2:231–237.

Denhardt et al., "Tissue inhibitor of metalloproteinases (TIMP, aka EPA): Structure, control of expression and biological functions" (1993) *J. Pharmacol. Ther.* 59:329–341.

Derkx et al., "High levels of interleukin–10 during the initial phase of fulminant meningococcal septic shock" (1995) *J. Infect. Dis.* 171:229–232.

Dessi et al. "Perturbations of triglycerides but not of cholesterol metabolism are prevented by anti–tumor necrosis factor treatment in rats bearing an ascites hepatoma (Yoshida AH–130)" (1995) *Br. J. Cancer* 72:1138–1143.

Dett et al., "Enhancement of lymphokine–activated T killer cell tumor necrosis factor receptor mRNA transcription, tumor necrosis factor receptor membrane expression, and tumor necrosis factor/lymphotoxin release by IL–1β, IL–4, and IL–6 in vitro" (1991) *J. Immunol.* 146:1522–1526.

Diez–Ruiz et al., "Soluble receptors for tumour necrosis factor in clinical laboratory diagnosis" (1995) *Eur. J. Haematol.* 54:1–8.

DiStefano et al., "Involvement of a metalloprotease in low–affinity nerve growth factor receptor truncation: Inhibition of truncation in vitro and in vivo" (1993)*J. Neurosci.* 13:2405–2414.

Docherty et al., "The matrix metalloproteinases and their natural inhibitors: prospects for treating degenerative tissue diseases" (1992) *TibTech.* 10:200–207.

Driscoll, K., "Macrophage inflammatory proteins" (1994) *Exp. Lung Res.* 20:474–490.

Dubravec et al., "Circulating human peripheral blood granulocytes synthesis and secrete tumor necrosis factor α" (1990) *Proc. Natl. Acad. Sci. USA* 87:6758–6761.

Durez et al., "In vivo induction of interluekin 10 by anti–CD3 monoclonal antibody or bacterial lipopolysaccharide: Differential modulation by cyclosporin A" (1993) *J. Exp. Med.* 177:551–555.

Echtenacher et al., "Critical protective role of mast cells in a model of acute septic peritonitis" (1996) *Nature* 381:75–77.

Elliott et al., "Suppression of fever and the acute–phase response in a patient with juvenile chronic arthritis treated with monoclonal antibody to tumour necrosis factor–α (cA2)" (1997) *Br. J. Rheumatology* 36:589–593.

Engelmann et al., "A tumor necrosis factor–binding protein purified to homogeneity from human urine protects cells from tumor necrosis factor toxicity" (1989) *J. Biol. Chem.* 264:11974–11980.

Engelmann et al., "Two tumor necrosis factor–binding proteins purified from human urine" (1990) *J. Biol. Chem.* 265:1531–1536.

Ertel et al., "Increased release of soluble tumor necrosis factor receptor into blood during clinical sepsis" (1994) *Arch. Surg.* 129:1330–1337.

Evans et al., "Tumour nectosis factor α (cachectin) mimics some of the effects of tumour growth on the disposal of a [$^{14}$C]lipid load in virgin, lactating and litter–removed rats" (1988) *Biochem. J.* 256:1055–1058.

Ey et al., "Isolation of pure IgG$_1$, IgG$_{2a}$ and IgG$_{2b}$ immunoglobulins from mouse serum using protein A–Sepharose" (1978) *Immunochemistry* 15:429–436.

Fargeas et al., "Central actin of interleukin 1β on intestinal motility in rats: Mediation by two mechanisms" (1993) *Gastroenterology* 104:377–383.

Feingold et al., "Stimulation of lipolysis in cultured fat cells by tumor necrosis factor, interleukin–1, and the interferons in blocked by inhibition of prostaglandin synthesis" (1992) *Endocrinology* 130:10–16.

Fenner, H., "TNF–inhibitoren: Eine neue therapeutische perspektive bei chronisch–entzündlichen Erkrankungen in der Rheumatologie?" (English abstract included) (1995) *Z. Rheumatol.* 54:158–164.

Ferrante, "Activation of neutrophils by interleukins–1 and –2 and tumor necrosis factors" (1992) *Immunol. Ser.* 57:417–436.

Fiers, "Tumor necrosis factor: Characterization at the molecular, cellular and in vivo level" (1991) *FEBS Lett.* 285:199–212.

Fiorentino et al., "IL–10 inhibits cytokine production by activated macrophages" (1991) *J. Immunol.* 147:3815–3822.

Fisher et al., "Treatment of septic shock with the tumor necrosis factor receptor:Fc fusion protein" (1996) *N. Engl. J. Med.* 334:1697–1702.

Fletcher et al., "Recent advances in the understanding of the biochemistry and clinical pharmacology of interleukin–2"(1987) *Lymphokine Res.* 6:45–57.

Flores et al., "Infusion of tumor necrosis factor/cachectin promotes muscle catabolism in the rat" (1989) *J. Clin. Invest.* 83:1614–1622.

Fried et al., "Cachectin/tumor necrosis factor decreases human adipose tissue lipoprotein lipase mRNA levels, synthesis, and activity" (1989) *J. Lipid. Res.* 30:1917–1923.

Fukunaga et al., "Three different mRNAs encoding human granulocyte colony–stimulating factor receptor" (1990) *Proc. Natl. Acad. Sci. USA* 8702–8706.

Garcia–Martinez et al., "Tumour necrosis factor–α increased the ubiquitinization of rat skeletal muscle proteins" (1993) *FEBS Lett.* 323:211–214.

Gatanaga, et al., "Release of soluble TNF/LT receptors from a human ovarian tumor cell line (PA–1) by stimulation with cytokines in vitro" (1993) *Lymphokine and Cytokine Res.* 12:249–253.

Gatanaga et al., "Identification of TNF–LT blocking factor(s) in the serum and ultrafiltrates of human cancer patients" (1990) *Lymphokine Res.* 9:225–229.

Gatanaga et al., "Purification and characterization of an inhibitor (soluble tumor necrosis factor receptor) for tumor necrosis factor and lymphotoxin obtained from the serum ultrafiltrates of human cancer patients" (1990) *Proc. Natl. Acad. Sci USA* 87:8781–8784.

Gatanaga et al., "The regulation of TNF receptor mRNA synthesis, membrane expression, and release by PMA– and LPS–stimulated human monocytic THP–1 cells in vitro" (1991) *Cell Immunol.* 138:1–10.

Gearing et al., "Processing of tumour necrosis factor–α precursor by metalloproteinases" (1994) *Nature* 370:555–557.

Gearing et al., "Matrix metalloproteinases and processing of pro–TNF–α" (1995) *J. Leukoc. Biol.* 57:774–777.

Gehr et al., "Both tumor necrosis factor receptor types mediate proliferative signals in human mononuclear cell activation" (1992) *J. Immunol.* 149:911–917.

Gennuso et al., "Effect of blood–brain barrier and blood–tumor barrier modification on central nervous system liposomal uptake" (1993) *Cancer Invest.* 11:118–128.

Gérard et al., "Interleukin 10 reduces the release of tumor necrosis factor and prevents lethality in experimental endotoxemia" (1993) *J. Exp. Med.* 177:547–550.

Golstein et al., "Cell death mechanisms and the immune system" (1991) *Immunol. Rev.* 121:29–65.

Goodman, "Tumor necrosis factor induces skeletal muscle protein breakdown in rats" (1991) *Am. J. Physiol.* 260:E727–E730.

Goodwin et al., "Cloning of the human and murine interleukin–7 receptor: Demonstration of a soluble form and homology to a new receptor superfamily" (1990) *Cell* 60:941–951.

Gordon et al., "Mast cells as a source of both preformed and immunologically inducible TNF–α/cachetin" (1990) *Nature* 346:274–276.

Grau et al., "Tumor necrosis factor (cachectin) as an essential mediator in murine cerebral malaria" (1987) *Science* 237:1210–1212.

Grell et al., "Segregation of APO–1/Fas antigen– and tumor necrosis factor receptor/mediated apoptosis" (1994) *Euro. J. Immunol.* 24:2563–2566.

Grosen et al., "Measurement of the soluble membrane receptors for tumor necrosis factor and lymphotoxin in the sera of patients with gynecologic malignancy" (1993) *Gynecol. Oncol.* 50:68–77.

Grunfeld et al., "Endotoxin and cytokines induce expression of leptin, the ob gene product, in hamsters" (1996) *J. Clin. Invest.* 97:2152–2157.

Gullberg et al., "Involvement of an Asn/Val cleavage site in the production of a soluble form of a human tumor necrosis factor (TNF) receptor. Site–directed mutagenesis of a putative cleavage site in the p55 TNF receptor chain" *Eur. J. Cell. Biol.* (1992) 58:307–312.

Hahne et al., "A novel soluble form of mouse VCAM–1 is generated from a glycolipid–anchored splicing variant" (1994) *Eur. J. Immunol.* 24:421–428.

Halwachs et al., "Serum levels of the soluble receptor for tumor necrosis factor in patients with renal disease" (1994) *Clin. Investig.* 72:473–476.

Hansen et al., "A zinc metalloproteinase is responsible for the release of CD30 on human tumor cell lines" (1995) *Int. J. Cancer* 63:750–756.

Hauner et al., "Effects of tumour necrosis factor alpha (TNFα) on glucose transport and lipid metabolism of newly–differentiated human fat cells in cell culture" (1995) *Diabetologia* 38:764–771.

Heller et al., "Complementary DNA cloning of a receptor for tumor necrosis factor and demonstration of a shed form of the receptor" (1990) *Proc. Natl. Acad. Sci. USA* 87:6151–6155.

Henney et al., "Localization of stromelysin gene expression in atherosclerotic plaques by in situ hyb ridization" (1991) *Proc. Natl. Acad. Sci. USA* 88:8154–8158.

Hibbs et al., "Biochemical and immunological characterization of the secreted forms of human neutrophil gelatinase" (1985) *J. Biol. Chem.* 260:2493–2500.

Himmler et al., "Molecular cloning and expression of human and rat tumor necrosis factor receptor chain (p60) and its soluble derivative, tumor necrosis factor–binding protein" (1990) *DNA Cell Biol.* 9:705–715.

Hintzen et al., "Characterization of the human CD27 ligand, a novel member of the TNF gene family" (1994) *J. Immunol.* 152:1762–1773.

Hjemdahl et al., "β–adrenoceptors in human alveolar macrophages isolated by elutriation" (1990) *Br. J. Clin. Pharmacol.* 30:673–682.

Hofmann et al., "Altered gene expression for tumor necrosis factor–α and its receptors during drug and dietary modulation of insulin resistance" (1994) *Endocrinology* 134:264–270.

Holtmann et al., "Down regulation of the receptors for tumor necrosis factor by interleukin 1 and 4β–phorbol 12–myristate–13–acetate" (1987) *J. Immunol.* 139:1161–1167.

Hotamisligil et al., "Increased adipose tissue expression of tumor necrosis factor–α in human obesity and insulin resistance" (1995) *J. Clin. Invest.* 95:2409–2415.

Howard et al., "Interleukin 10 protects mice from lethal endotoxemia" (1993) *J. Exp. Med.* 177:1205–1208.

Hu et al., "The effect of norepinephrine on endotoxin–mediated macrophage activation" (1991) *J. Neuroimmunol.* 31:35–42.

Huizinga et al., "The PI–linked receptor FcRIII is released on stimulation of neutrophils" (1988) *Nature* 333:667–669.

Hwang et al., "Mechanism of release of soluble forms of tumor necrosis factor/lymphotoxin receptors by phorbol myristate acetate–stimulated human THP–1 cells in vitro" (1993) *J. Immunol..* 151:5631–5638.

Jin et al., "Protection against rat endotoxic shock by p55 tumor necrosis factor (TNF) receptor immunoadhesin: Comparison with anti–TNF monoclonal antibody" (1994) *J. Infect. Dis.* 170:1323–1326.

Joyce et al., "Two inhibitors of pro–inflammatory cytokine release, interleukin–10 and interleukin–4, have contrasting effects on release of soluble p75 tumor necrosis factor receptor by cultured monocytes" (1994) *Eur. J. Immunol.* 24:2699–2705.

Kalinkovich et al., "Increased soluble tumor necrosis factor receptor expression and release by human immunodeficiency virus type 1 infection" (1995) *J. Interferon Cyto. Res.* 15:749–757.

Katsikis et al., "Immunoregulatory role of interleukin 10 in rheumatoid arthritis" (1994) *J. Exp. Med.* 179:1517–1527.

Katsura et al., "Identification of the proleolytic enzyme which cleaves human p75 TNF receptor in vitro" (1996) *Biochem. Biophys. Res. Com.* 222:298–302.

Katsura et al., "Identification and characterization of soluble TNF receptor releasing enzyme (TRRE) from PMA–stimulated human monocytic THP–1 cells" (1996) *Proc. Amer. Cancer Res. Meeting* Apr. 20–24,37:492 (Abstract 3359).

Kawakami et al., "Human recombinant TNF suppresses lipoprotein lipase activity and stimulates lipolysis in 3T3–L1 cells" (1987) *J. Biochem.* 101:331–338.

Khire et al., "EGF stimulates the processing and export of a secreted form of EGF receptor" (1990) *Febs. Lett.* 272:69–72.

Khokha et al., "Antisense RNA–induced reduction in murine TIMP levels confers oncogenicity on Swiss 3T3 cells" (1989) *Science* 243:947–950.

Klinkert et al., "TNR–α receptor fusion protein prevents experimental auto–immune encephalomyelitis and demyelination in Lewis rats: an overview" (1997) *J. Neuroimmun.* 72:163–168.

Kohno et al., "A second tumor necrosis factor receptor gene product can shed a naturally occurring tumor necrosis factor inhibitor" (1990) *Proc. Natl. Acad. Sci. USA* 87:8331–8335.

Kostis et al., "Central nervous system effects of HMG CoA reductase inhibitors: Lovastatin and pravastatin on sleep and cognitive performance in patients with hypercholesterolemia" (1994) *J. Clin. Pharmacol.* 34:989–996.

Kriegler et al., "A novel form of TNF/cachectin is a cell surface cytotoxic transmembrane protein: Ramifications for the complex physiology of TNF" (1988) *Cell* 53:45–53.

Lambert et al., "Natural serum TNF antagonists in end–stage renal failure and following renal transplantation" (1994) *Nephrol. Dia. Transplant.* 9:1791–1796.

Landmann et al., "Interferon–γ and interleukin–4 down–regulate soluble CD14 release in human monocytes and macrophages" (1992) *J. Leukoc. Biol.* 52:323–330.

Latza et al., "CD30 antigen in embryonal carcinoma and embryogenesis and release of the soluble molecule" (1995) *Am. J. Pathol.* 146:463–471.

Lawson et al., "Metabolic approaches to cancer cachexia" (1982) *Annu. Rev. Nutr.* 2:277–301.

Leca et al., "Expression of VCAM–1 (CD106) by a subset of TCRγδ–bearing lymphocyte clones" (1995) *J. Immunol.* 154:1069–1077.

Leeuwenberg et al., "Slow release of soluble TNF receptors by monocytes in vitro" (1994) *J. Immunol.* 152:4036–4043.

Lesslauer et al., "Recombinant soluble tumor necrosis factor receptor proteins protect mice from lipopolysaccharide–induced lethality" (1991) *Eur. J. Immunol.* 21:2883–2886.

Levin, V. "Relationship of Octanol/water partition coefficient and molecular weight to rat brain capillary permeability" (1990) *J. Med. Chem.* 23:682–684.

Levy et al., "Increased expression of the $M_r$ 72,000 type IV collagenase in human colonic adenocarcinoma" (1991) *Cancer Res.* 51:439–444.

Llovera et al., "Effects of tumor necrosis factor–α on muscle–protein turnover in female Wistar rats" (1993) *J. Natl. Cancer Inst.* 85:1334–1339.

Loenen et al., "The CD27 membrane receptor, a lymphocyte–specific member of the nerve growth factor receptor family, gives rise to a soluble form by protein processing that does not involve receptor endocytosis" (1992) *Eur. J. Immunol.* 22:447–455.

Loetscher et al., "Purification and partial amino acid sequence analysis of two distinct tumor necrosis factor receptors from HL60 cells" (1990) *J. Biol. Chem.* 265:20131–20138.

Loetscher et al., "Molecular cloning can expression of the human 55 kd tumor necrosis factor receptor" (1990) *Cell* 61:351–359.

López–Casillas et al., "Structure and expression of the membrane proteoglycan betaglycan a component of the TGF–β receptor system" (1991) *Cell* 67:785–795.

Lovejoy et al., "Structure of the catalytic domain of fibroblast collagenase complexed with an inhibitor" (1994) *Science* 263:375–377.

Lowry et al., "Metal ion stabilization of the conformation of a recombinant 19–kDa catalytic fragment of human fibroblast collagenase" (1992) *Proteins* 12:42–48.

Lyons et al., "Characteristics of a 95–kDa matrix metalloproteinase produced by mammary carcinoma cells" (1991) *Biochemistry* 30:1449–1456.

Mack et al., "Candida infection following severe trauma exacerbates Th2 cytokines and increases mortality" (1997) *J. Surg. Res.* 69:399–407.

Madej et al., "Threading analysis suggests that the obese gene product may be a helical cytokine" (1995) *FEBS Lett.* 373:13–18.

Maini et al., "TNF blockade in rheumatoid arthritis: Implications for therapy and pathogenesis" (1997) *Ampis* 105:257–263.

Marchant,A. "Contemporary management of breast cancer" (1994) *Obstetrics and Gynecology Clinics of North America* 21:555–560.

Marchant et al., "Interleukin–10 controls interferon–γ and tumor necrosis factor production during experimental endotoxemia" (1994) *Eur. J. Immunol.* 24:1167–1171.

Marchant et al., "Interleukin–10 production during septicaemia" (1994) *Lancet* 343:707–708.

Massagué, "TGFβ signaling: Receptors, transducers, and mad proteins" (1996) *Cell* 85:947–950.

Massagué"Membrane–anchored growth factors" (1993) *Annu. Rev. Biochem.* 62:515–541.

Matrisian, "Metalloproteinases and their inhibitors in matrix remodeling" (1990) *Trends Genet.* 6:121–125.

Matrisian, "The matrix–degrading metalloproteinases" (1992) *Bioessays* 14:455–463.

Matrisian et al., "The role of the matrix metalloproteinase stromelysin in the progression of squamous cell carcinomas" (1991) *Am. J. Med. Sci.* 302:157–162.

McGeehan et al., "Regulation of tumour necrosis factor–α processing by a metalloproteinase inhibitor" (1994) *Nature* 370:558–561.

Meakin et al., "The nerve growth factor family of receptors" (1992) *Trends Neurosci.* 15:323–331.

Michie et al., "Detection of circulating tumor necrosis factor after endotoxin administration" (1988) *New Engl. J. Med.* 318:1481–1486.

Mignatti et al. "Tumor invasion through the human amniotic membrane: Requirement for a proteinase cascade" (1986) *Cell* 47:487–498.

Miles et al., "Induction of soluble tumour necrosis factor receptors during treatment with interleukin–2" (1992) *Br. J. Cancer* 66:1195–1199.

Miyazaki et al., "Purification and characterization of extracellular matrix–degrading metalloproteinase, Matrin (Pump–1), secreted from human rectal carcinoma cell line" (1990) *Cancer Res.* 50:7758–7764.

Mohler et al., "Soluble tumor necrosis factor (TNF) receptors are effective therapeutic agents in lethal endotoxemia and function simultaneously as both TNF carriers and TNF antagonists" (1993) *J. Immunol.* 151:1548–1561.

Mohler et al., "Protection against a lethal dose of endotoxin by an inhibitor of tumour necrosis factor processing" (1994) *Nature* 370:218–220.

Möller et al., "Expression of APO–1 (CD95), a member of the NGF/TNF receptor superfamily, in normal and neoplastic colon epithelium" (1994) *Int. J. Cancer* 57:371–377.

Moore, "Interleukin–10" (1993) *Annu. Rev. Immunol.* 11:165–190.

Moreland et al., "Treatment of rheumatoid arthritis with a recombinant human tumor necrosis factor receptor (P75)–Fc fusion protein" (1997) *N. Eng. J. Med.* 337:141–147.

Mosley et al., "The murine interleukin–4 receptor: Molecular cloning and characterization of secreted and membrane bound forms" (1989) *Cell* 59:335–348.

Müberg et al., "A metalloprotease inhibitor blocks shedding of the IL–6 receptor and the p60 TNF receptor" (1995) *J. Immunol..* 155:5198–5205.

Murphy et al., "Metalloproteinases and tissue damage" (1991) *Br. J. Rheumatol.* 30:25–31.

Naito et al., "Inhibition of growth of human tumor cells in nude mice by a metalloproteinase inhibitor" (1994) *Int. J. Cancer* 58:730–735.

Naume et al., "Involvement of the 55– and 75–kDa tumor necrosis factor receptors in the generation of lymphokine–activated killer cell activity and proliferation of natural killer cells" (1991) *J. Immunol.* 146:3045–3048.

Neurath et al., "Predominant pathogenic role of tumor necrosis factor in experimental colitis in mice" (1997) *Eur. J. Immun.* 27:1743–1750.

Neuwelt et al., "Modification of the blood–brain barrier in the chemotherapy of malignant brain tumors" (1984) *Fed. Proc.* 43:214–219.

Nicholls, "The thermogenic mechanism of brown adipose tissue" (1983) *Biosci. Rep.* 3:431–441.

Nophar et al., "Soluble forms of tumor necrosis factor receptors (TNF–Rs). The cDNA for the type 1 TNF–R, cloned using amino acid sequence data of its soluble form, encodes both the cell surface and a soluble form of the receptor" (1990) *EMBO J.* 9:3269–3278.

Novick et al., "Soluble cytokine receptors are present in normal human urine" (1989) *J. Exp. Med.* 170:1409–1414.

Ogiwara et al., "Diminished visceral adipose tissue in cancer cachexia" (1994) *J. Surg. Oncol.* 57:129–133.

Old, "Another chapter in the long history of endotoxin" (1987) *Nature* 330:602–603.

Oliff et al., "Tumors secreting human TNF/cachectin induce cachexia in mice" (1987) *Cell* 50:555–563.

Olsson et al., "Isolation and characterization of a tumor necrosis factor binding protein from urine" (1989) *Eur. J. Haematol.* 42:270–275.

Olsson et al., "The receptors for regulatory molecules of hematopoiesis" (1992) *Eur. J. Haematol.* 48:1–9.

Olsson et al., "Tumour necrosis factor (TNF) binding proteins (soluble TNF receptor forms) with possible roles in inflammation and malignancy" (1993) *Eur. Cytokine Netw.* 4:169–180.

Oudart et al., "Stimulation of brown adipose tissue activity in tumor–bearing rats" (1995) *Can. J. Physiol. Pharmacol.* 73:1625–1631.

Pandiella et al., "Cleavage of the membrane precursor for transforming growth factor α is a regulated process" (1991) *Proc. Natl. Acad. Sci. USA* 88:1726–1730.

Peetre et al., "A tumor necrosis factor binding protein is present in human biological fluids" (1988) *Eur. J. Haematol.* 41:414–419.

Phillips et al., "Leptin receptor missense mutation in the fatty Zucker rat" (1996) *Nature Genet.* 13:18–19.

Pizza et al, "Tumour regression after intralesional injection of interleukin 2(IL–2) in bladder cancer. Preliminary report" (1984) *Int. J. Cancer* 34:359–367.

Plata–Salamán et al., "Chemokines/intercrines and central regulation of feeding" (1994) *Am. J. Physiol.* 266:R1711–R1715.

Porat et al., "Glysolated recombinant human tumor necrosis factor binding protein–1 reduces mortality, shock, and production of tumor necrosis factor in rabbit *Escherichia coli* sepsis" (1995) *Crit. Care Med.* 23:1080–1089.

Porteu, "Tumor necrosis factor induces a selective shedding of its p75 receptor from human neutrophils" (1994) *J. Biol. Chem.* 269:2834–2840.

Porteu et al., "Shedding of tumor necrosis factor receptors by activated human neutrophils" (1990) *J. Exp. Med.* 172:599–607.

Porteu et al. "Human neutrophil elastase releases a ligand–binding fragment from the 75–kDa tumor necrosis factor (TNF) receptor" (1991) *J. Biol. Chem.* 266:18846–18853.

Powell et al., "Expression of the metalloproteinase matrilysin in DU–145 cells increases their invasive potential in severe combined immunodeficient mice" (1993) *Cancer Res.* 53:417–422.

Price et al., "Regulation of lipoprotein lipase synthesis by recombinant tumor necrosis factor – the primary regulatory role of the hormone in 3T3–L1 adipocytes" (1986) *Arch. Biochem. Biophys.* 251:738–746.

Rabinowich et al., "Functional analysis of mononuclear cells infiltrating into tumors: Lysis of autologous human tumor cells by cultured infiltrating lymphocytes" (1987) *Cancer Res.* 47:173–177.

Raines et al., "Identification and molecular cloning of a soluble human granulocyte–macrophage colony–stimulating factor receptor" (1991) *Proc. Natl. Acad. Sci. USA* 88:8203–8207.

Ray et al., "The role of matrix metalloproteases and their inhibitors in tumour invasion, metastasis and angiogenesis" (1994) *Eur. Respir. J.* 7:2062–2072.

Renauld et al., "Expression cloning of the murine and human interleukin 9 receptor cDNAs" (1992) *Proc. Natl. Acad. Sci. USA* 89:5690–5694.

Rose–John et al., "Soluble receptors for cytokines and growth factors: generation and biological function" (1994) *Biochem. J.* 300:281–290.

Rosenberg et al., "A new approach to the adoptive immunotherapy of cancer with tumor–infiltrating lymphocytes" (1986) *Science* 233:1318–1321.

Rothwell, "Cytokines and thermogenesis" (1993) *Int. J. Obesity* 17:S98–S101.

Saghizadeh et al., "The expression of TNFα by human muscle: Relationship to insulin resistance" (1996) *J. Clin. Invest.* 97:1111–1116.

Salat et al., "Hemostatic parameters in sepsis patients treated with anti–TNFα–monoclonal antibodies" (1996) *Shock* 6:233–237.

Sato et al., "Expression of genes encoding type IV collagen–degrading metalloproteinases and tissue inhibitors of metalloproteinases in various human tumor cells" (1992) *Oncogene* 7:77–83.

Schall et al., "Molecular cloning and expression of a receptor for human tumor necrosis factor" (1990) *Cell* 361–370.

Schwartz et al., "Hypothalamic response to starvation: implications for the study of wasting disorders" (1995) *Am. J. Physiol.* 269:R949–R957.

Scopes et al., "Analysis of proteins" (1987) *Current Protocols in Molecular Biology*, F. M. Ausubel et al., eds., pp. 10.0.1–10.0.19.

Scuderi et al., "Raised serum levels of tumour necrosis factor in parasitic infections" (1986) *Lancet* Dec. 13:1364–1365.

Seckinger et al., "A human inhibitor of tumor necrosis factor α" (1988) *J. Exp. Med.* 167:1511–1516.

Seckinger et al., "Purification and biologic characterization of a specific tumor necrosis factor α inhibitor " (1989) *J. Biol. Chem.* 264:11966–11973.

Seitz et al., "In vitro modulation of cytokine, cytokine inhibitor, and prostglandin E release from blood mononuclear cells and synovial fibroblasts by antirheumatic drugs" (1997) *J. Rheumatology* 24:1471–1476.

Seljelid et al., "Biological effects of the immunomodulator β1–3D polyglucose are strongly potentiated by conjugation to biodegradable microbeads" (1997) *Scand. J. Immunol.* 45:683–687.

Semb et al., "Multiple effects of tumor necrosis factor on lipoprotein lipase in vivo" (1987) *J. Biol. Chem.* 262:8390–8394.

Senior et al., "Elastin degradation by human alveolar macrophages" (1989) *Am. Rev. Respir. Dis.* 139:1251–1256.

Senior et al., "Human 92– and 72–kilodalton type IV collagenases are eleastases" (1991) *J. Biol. Chem.* 266:7870–7875.

Seth et al., "Circulating ICMA–1 isoforms: diagnostic prospects for inflammatory and immune disorders" (1991) *Lancet* 338:83–84.

Severn, et al. "Regulation of tumor necrosis factor production by adrenaline and β–adrenergic agonists" (1992) *J. Immunol.* 148:3441–3445.

Shalaby et al., "Binding and regulation of cellular functions by monoclonal antibodies against human tumor necrosis factor receptors" (1990) *J. Exp. Med.* 172:1517–1520.

Shohami et al., "Cytokine production in the brain following closed head injury: dexanabinol (HU–211) is a novel TNF–α inhibitor and an effective neuroprotectant" (1997) *J. Neuroimmun.* 72:169–177.

Simon et al., "Divergent T–cell cytokine patterns in inflammatory arthritis" (1994) *Proc. Natl. Acad. Sci. USA* 91:8562–8566.

Sledge et al., "Effect of matrix metalloproteinase inhibitor batimasta on breast cancer regrowth and metastasis in athymic mice" (1995) *J. Natl. Cancer Inst.* 87:1546–1550.

Smith et al., "A receptor for tumor necrosis factor defines an unusual family of cellular and viral proteins" (1990) *Science* 248:1019–1023.

Smith et al., "CD30 antigen, a marker for Hodgkin's lymphoma, is a receptor whose ligand defines an emerging family of cytokines with homology to TNF" (1993) *Cell* 73:1349–1360.

Solorzano et al., "A matrix metalloproteinase inhibitor prevents processing of tumor necrosis factor α (TNFα) and abrogates endotoxin–induced lethality" (1997) *Shock* 7:427–431.

Speiser et al., "TNF receptor p55 controls early acute graft–versus–host disease" (1997) *J. Immun.* 158:5185–5190.

Spengler et al., "Endogenous norepinephrine regulates tumor necrosis factor–α production from macrophages in vitro" (1994) *J. Immunol.* 152:3024–3031.

Spiegelman et al., "Through thick and thin: Wasting, obesity and TNFα" (1993) *Cell* 73:625–627.

Sreenath et al., "Expression of matrix metalloproteinase genes in transformed rat cell lines of high and low metastatic potential" (1992) *Cancer Res.* 52:4942–4947.

Stack et al., "Randomised controlled trial of CDP571 antibody to tumour necrosis factor–α in Crohn's disease" (1997) *Lancet* 349:521–524.

Stein et al., "Proteolytic processing of a plasma membrane–bound precursor to human macrophage colony–stimulating factor (CSF–1) is accelerated by phorbol ester" (1991) *Oncogene* 6:601–605.

Takaki et al., "Molecular cloning and expression of the murine interleukin–5 receptor" (1990) *EMBO J.* 9:4367–4374.

Talmadge et al., "Molecular pharmacology of the beta–adrenergic receptor on THP–1 cells" (1993) *Int. J. Immunopharmacol.* 15:219–228.

Tan et al., "Trauma causes early release of soluble receptors for tumor necrosis factor" (1993) *J. Trauma* 34:634–638.

Tartaglia et al., "Two TNF receptors" (1992) *Immunol. Today* 13:151–153.

Tartaglia et al., "The two different receptors for tumor necrosis factor mediate distinct cellular responses" (1991) *Proc. Natl. Acad. Sci. USA* 88:9292–9296.

Tiesman et al., "Identification of a soluble receptor for platelet–derived growth factor in cell–conditioned medium and human plasma" (1993) *J. Biol. Chem.* 268:9621–9628.

Tijssen et al., "Highly efficient and simple methods for the preparation of peroxidase and active peroxidase–antibody conjugates for enzyme immunoassays" (1984) *Anal. Biochem.* 136:451–457.

Tracey et al., "Anti–cachectin/TNF monoclonal antibodies prevent septic shock during lethal bacteraemia" (1987) *Nature* 330:662–664.

Tracey et al., "Cachectin/tumor necrosis factor induces lethal shock and stress hormone responses in the dog" (1987) *Surg. Gynecol. Obstet.* 164:415–422.

van der Poll, et al., "Endogenous IL–10 protects mice from death during septic peritonitis" (1995) *J. Immunol.* 155:5397–5401.

van der Poll et al., "Tumor necrosis factor is sepsis: Mediator of multiple organ failure or essential part of host defense?" (1995) *Shock* 3:1–12.

van Deuren, "Kinetics of tumour necrosis factor–alpha, soluble tumour necrosis factor receptors, interleukin 1–beta and its receptor antagonist during serious infections" (1994) *Eur. J. Clin. Microbiol. Infect. Dis.* 13(Suppl. 1): S12–S16.

van Deventer et al., "Monoclonal antibody therapy of inflammatory bowel disease" (1997) *Pharm. World Sci.* 19:55–59.

Van Hogezand et al., "New therapies for inflammatory bowel disease: an update on chimeric anti–TNFα antibodies and IL–10 therapy" (1997) *Scand. J. Gastro.* 223:105–107.

Van Wart et al., "The cysteine switch: A principle of regulation of metalloproteinase activity with potential applicability to the entire matrix metalloproteinase gene family" (1990) *Proc. Natl. Acad. Sci. USA* 87:5578–5582.

Van Zee et al., "Tumor necrosis soluble receptors circulate durng experimental and clinical inmflammation and can protect against excessive tumor necrosis factor α in vitro and in vivo" (1992) *Proc. Natl. Acads. Sci. USA* 89:4845–4849.

Vincenti et al., "Using inhibitors of metalloproteinases to treat arthritis" (1994) *Arth. & Rheum.* 37:1115–1126.

Waage et al., "Detection of tumour necrosis factor–like cytotoxicity in serum from patients with septicaemia but not from untreated cancer patients" (1986) *Scand. J. Immunol.* 24:739–743.

Watson et al., "Inhibition of organ invasion by the matrix metalloproteinase inhibitor batimastat (BB–94) in two human colon carcinoma metastasis models" (1995) *Cancer Res.* 55:3629–3633.

Woessner, Jr., "Matrix metalloproteinases and their inhibitors in connective tissue remodeling" (1991) *FASEB J.* 5:2145–2154.

Yamamoto et al., "The human LT system. II. Immunological relationships of LT molecules released by mitogen activated human lymphocytes in vitro" (1978) *Cell. Immunol.* 38:403–416.

Yamamoto et al., "FR167653, a dual inhibitor of interleukin–1 and tumor necrosis factor–60 , ameliorates endotoxin–induced shock" (1997) *Eur. J. Pharmacol.* 327:169–175.

Yui et al., "Cytotoxicity of tumour necrosis factor–alpha and gamma–interferon against primary human placental trophoblasts" (1994) *Placenta* 15:819–835.

Zamir et al., "Evidence that tumor necrosis factor participates in the regulation of muscle proteolysis during sepsis" *Arch. Surg.* 127:170–174.

Zhang et al., "Positional cloning of the mouse obese gene and its human homologue" (1994) *Nature* 372:425–432.

Zupan et al., "Identification, purification, and characterization of truncated forms of the human nerve growth factor receptor" (1989) *J. Biol. Chem.* 264:11714–11720.

\* cited by examiner

FIG. 3
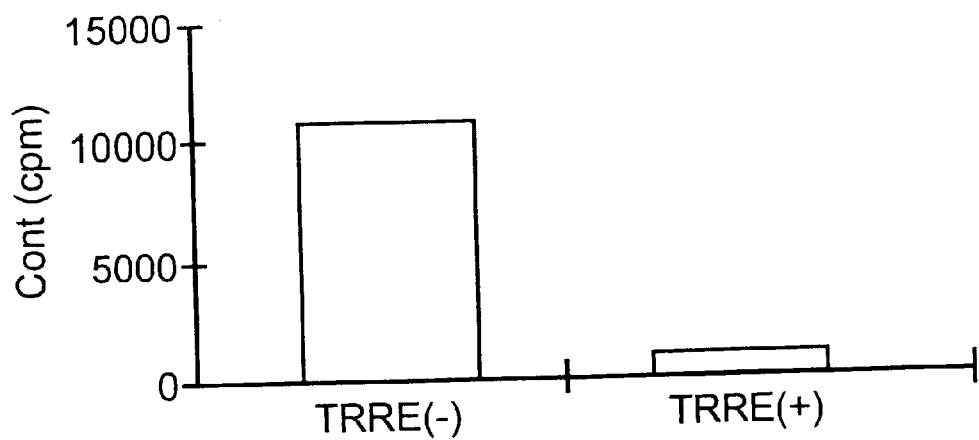
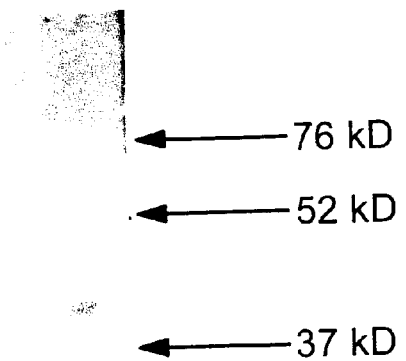
FIG. 4

A

B

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 14 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Asp Leu Asn Leu Gly Ala Gln Ala Thr Ile Thr Asn Leu Pro
1               5                   10

(2) INFORMATION FOR SEQ ID NO:2:

(i) SEQUENCE CHARACTERISTICS:
      (A) LENGTH: 13 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Gly Leu Asp Glu Thr Gln Asn Leu Ile Thr Val Pro Tyr
1               5                   10

(2) INFORMATION FOR SEQ ID NO:3:

(i) SEQUENCE CHARACTERISTICS:
      (A) LENGTH: 13 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:3:

Ser Glu Arg Trp Pro Gln Met Ala Asn Lys Val Ser Arg
1               5                   10

(2) INFORMATION FOR SEQ ID NO:4:

(i) SEQUENCE CHARACTERISTICS:

```
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:4:

Ile Val Val Thr Lys
1               5

(2) INFORMATION FOR SEQ ID NO:5:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 4
            (D) OTHER INFORMATION: /note= "Xaa is His or Ser (H/S)"

(xi) SEQUENCE DESCRIPTION: SEQ ID NO:5:

Glu Phe Pro Xaa Pro Val Asp Ala Ala Thr Arg
1               5                   10

(2) INFORMATION FOR SEQ ID NO:6:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 11
            (D) OTHER INFORMATION: /note= "Xaa is Leu or Glu (L/E)"

(ix) FEATURE:
            (A) NAME/KEY: Modified-site
            (B) LOCATION: 15
            (D) OTHER INFORMATION: /note= "Xaa is Ile or Asn (I/N)"

(xi) SEQUENCE DESCRIPTION: SEQ ID NO:6:

Ala Leu Phe Glu Leu Ile Tyr Glu Leu Leu Xaa Ala Thr Ile Xaa Val
1               5                   10                  15

(2) INFORMATION FOR SEQ ID NO:7:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 5
            (D) OTHER INFORMATION: /note= "Xaa is Glu or Thr (E/T)"

(xi) SEQUENCE DESCRIPTION: SEQ ID NO:7:

Leu Asp Tyr Gln Xaa Ser Tyr Ser Ala Ala Val Ala Arg
1               5                   10
```

(2) INFORMATION FOR SEQ ID NO:8:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "Xaa is Gln or Ile (Q/I)"

(ix) FEATURE:
        (A) NAME/KEY: Modified-site
        (B) LOCATION: 8
        (D) OTHER INFORMATION: /note= "Xaa is Ser or Pro (S/P)"

(xi) SEQUENCE DESCRIPTION: SEQ ID NO:8:

Leu Ala Leu Xaa Glu Ser Pro Xaa
1               5

(2) INFORMATION FOR SEQ ID NO:9:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Leu Phe Leu Lys Asn Thr Gly Leu Ala Arg
1               5                   10

(2) INFORMATION FOR SEQ ID NO:10:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Met Ala Leu Gln Lys Gly Asp Arg
1               5

(2) INFORMATION FOR SEQ ID NO:11:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Lys Leu Leu Glu Leu Asn Val Val Ala
1               5

(2) INFORMATION FOR SEQ ID NO:12:

(i) SEQUENCE CHARACTERISTICS:

(A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa is Val or Ile (V/I)"

(ix) FEATURE:
        (A) NAME/KEY: Modified-site
        (B) LOCATION: 9
        (D) OTHER INFORMATION: /note= "Xaa is any amino acid"

(xi) SEQUENCE DESCRIPTION: SEQ ID NO:12:

Xaa Thr Asp Met Val Val Gly Ile Xaa Gly
1               5                   10

(2) INFORMATION FOR SEQ ID NO:13:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /note= "Xaa is any amino acid"

(xi) SEQUENCE DESCRIPTION: SEQ ID NO:13:

Leu Val Asp Tyr Asp Xaa Leu Phe Gln Asn Leu
1               5                   10

(2) INFORMATION FOR SEQ ID NO:14:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Lys Glu Ala Leu Ile Ala Lys Ile Arg
1               5

(2) INFORMATION FOR SEQ ID NO:15:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 10
        (D) OTHER INFORMATION: /note= "Xaa is Ile or Leu (I/L)"

(xi) SEQUENCE DESCRIPTION: SEQ ID NO:15:

Asp Leu Asn Leu Gly Ala Gln Ala Thr Xaa Thr Asn Leu Pro
1               5                   10

(2) INFORMATION FOR SEQ ID NO:16:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /note= "Xaa is Gly or Leu (G/L)"

(ix) FEATURE:
        (A) NAME/KEY: Modified-site
        (B) LOCATION: 11
        (D) OTHER INFORMATION: /note= "Xaa is Glu or Gly (E/G)"

(xi) SEQUENCE DESCRIPTION: SEQ ID NO:16:

```
Leu Ala Glu Asp Tyr Leu Ser Xaa Trp Leu Xaa Arg
1               5                  10
```

(2) INFORMATION FOR SEQ ID NO:17:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa is Leu or Lys (L/K)"

(ix) FEATURE:
        (A) NAME/KEY: Modified-site
        (B) LOCATION: 2
        (D) OTHER INFORMATION: /note= "Xaa is Val or Leu (V/L)"

(ix) FEATURE:
        (A) NAME/KEY: Modified-site
        (B) LOCATION: 3
        (D) OTHER INFORMATION: /note= "Xaa is Asp or Glu (D/E)"

(ix) FEATURE:
        (A) NAME/KEY: Modified-site
        (B) LOCATION: 5
        (D) OTHER INFORMATION: /note= "Xaa is Asp or Glu (D/E)"

(ix) FEATURE:
        (A) NAME/KEY: Modified-site
        (B) LOCATION: 7
        (D) OTHER INFORMATION: /note= "Xaa is Leu or Phe (L/F)"

(ix) FEATURE:
        (A) NAME/KEY: Modified-site
        (B) LOCATION: 6
        (D) OTHER INFORMATION: /note= "Xaa is an unidentified
            amino acid"

(xi) SEQUENCE DESCRIPTION: SEQ ID NO:17:

```
Xaa Xaa Xaa Tyr Xaa Xaa Xaa Phe Gln Asn Leu
1               5                  10
```

NATIVE TNF RECEPTOR RELEASING ENZYME

CROSS-REFERENCE TO RELATED APPLICATIONS

This application is a continuation-in-part of Provisional Patent Application No. 60/030,761, filed Nov. 6, 1996.

FIELD OF THE INVENTION

This invention relates to the purification and characterization of tumor necrosis factor (TNF) receptor (TNF-R) releasing enzyme (TRRE), compositions derived from the enzyme, and methods of use thereof. Modulation of TRRE levels indirectly modulates effective levels of TNF. The invention further relates to methods of treatment of pathological conditions caused or exacerbated by altered levels or activity of TNF such as inflammatory conditions including autoimmune diseases, infections, septic shock, obesity, cachexia, and conditions that are associated with decreased levels or activity of TNF such as cancer.

BACKGROUND OF THE INVENTION

Tumor necrosis factor (TNF or TNF-α) and lymphotoxin (LT or TNF-β) are related cytokines that share 40 percent amino acid (AA) sequence homology. Old (1987) *Nature* 330:602–603. These cytokines are released mainly by macrophages, monocytes and natural killer (NK) cells in response to broad immune reactions. Gorton and Galli (1990) *Nature* 346:274–276; and Dubravec et al. (1990) *Proc. Natl. Acad. Sci. USA* 87:6758–6761. Although initially discovered as agents inducing hemorrhagic necrosis of tumors, these cytokines have been shown to have essential roles in both the inductive and effector phases of immune reactions and inflammation. The two cytokines cause a broad spectrum of effects on cells in vitro and tissues in vivo, including: (i) vascular thrombosis and tumor necrosis; (ii) inflammation; (iii) activation of macrophages and neutrophils; (iv) leukocytosis; (v) apoptosis; and (vi) shock. Beretz et al. (1990) *Biorheology* 27:455–460; Driscoll (1994) *Exp. Lung Res.* 20:473–490; Ferrante (1992) *Immunol. Ser.* 57:417–436; Golstein et al. (1991) *Immunol. Rev.* 121:29–65; and van der Poll and Lowry (1995) *Shock* 3:1–12. For a review of the mechanism of action of TNF, see Massague (1996) *Cell* 85:947–950. TNF has been associated with a variety of disease states including various forms of cancer, arthritis, psoriasis, endotoxic shock, sepsis, autoimmune diseases, infections, obesity, and cachexia. Attempts have been made to alter the course of a disease by treating the patient with TNF inhibitors with varying degrees of success. For example, oxpentifylline did not alter the course of Crohn's disease, a chronic inflammatory bowel disease. Bauditz et al. (1997) *Gut* 40:470–4. However, the TNF inhibitor dexanabinol provided protection against TNF following traumatic brain injury. Shohami et al. (1997) *J. Neuroimmun.* 72:169–77.

Human TNF and LT mediate their biological activities, both on cells and tissues, by binding specifically to two distinct, although related, glycoprotein plasma membrane receptors of 55 kDa and 75 kDa (p55 and p75 TNF-R, respectively). Holtmann and Wallach (1987) *J. Immunol.* 139:151–153. The two receptors share 28 percent AA sequence homology in their extracellular domains, which are composed of four repeating cysteine-rich regions. Tartaglia and Goeddel (1992) *Immunol. Today* 13:151–153. However, the receptors lack significant AA sequence homology in their intracellular domains. Dembic et al. (1990) *Cytokine* 2:231–237. Due to this dissimilarity, they may transduce different signals and, in turn, exercise diverse functions.

Recent studies have shown that most of the known cellular TNF responses, including cytotoxicity and induction of several genes, may be attributed to p55 TNF-R activation. Engelmann et al. (1990) *J. Biol. Chem.* 265:1531–1536; Shalaby et al. (1990) *J. Exp. Med.* 172:1517–1520; and Tartaglia et al. (1991) *Proc. Natl. Acad. Sci. USA* 88:9292–9296. In addition, the p55 receptor controls early acute graft-versus-host disease. Speiser et al. (1997) *J. Immun.* 158:5185–90. In contrast, information regarding the biological activities of p75 TNF-R is limited. This receptor shares some activities with p55 TNF-R and specifically participates in regulating proliferation of and secretion of cytokines by T cells. Shalaby et al. (1990); and Gehr et al. (1992) *J. Immunol.* 149:911–917. Both belong to an ever-increasing family of membrane receptors including low-affinity nerve growth factor receptor (LNGF-R), FAS antigen, CD27, CD30 (Ki-1), CD40 (gp50) and OX 40. Cosman (1994) *Stem Cells* (Dayt.) 12:440–455; Meakin and Shooter (1992) *Trends Neurosci.* 15:323–331; Grell et al. (1994) *Euro. J. Immunol.* 24:2563–2566; Moller et al. (1994) *Int. J. Cancer* 57:371–377; Hintzen et al. (1994) *J. Immunol.* 152:1762–1773; Smith et al. (1993) *Cell* 73:1349–1360; Corcoran et al. (1994) *Eur. J. Biochem.* 223:831–840; and Baum et al. (1994) *EMBO J.* 13:3992–4001.

All of these receptors share a repetitive pattern of cysteine-rich domains in their extracellular regions. In accord with the pleiotropic activities of TNF and LT, most human cells express low levels (2,000 to 10,000 receptors/cell) of both TNF-Rs simultaneously. Brockhaus et al. (1990) *Proc. Natl. Acad. Sci. USA* 87:3127–3131. Expression of TNF-R on both lymphoid and non-lymphoid cells may be up and down-regulated by many different agents, such as bacterial lipopolysaccharide (LPS), phorbol myristate acetate (PMA; a protein kinase C activator), interleukin-1 (IL-1), interferon-gamma (IFN-γ) and IL-2. Gatanaga et al. (1991) *Cell Immunol.* 138:1–10; Yui et al. (1994) *Placenta* 15:819–835; and Dett et al. (1991) *J. Immunol.* 146:1522–1526. Although expressed in different proportions, each receptor binds TNF and LT with equally high affinity. Brockhaus et al. (1990); and Loetscher et al. (1990) *J. Biol. Chem.* 265:20131–20138. Initial studies showed that the complexes of human TNF and TNF-R are formed on the cell membrane, internalized wholly, and then either degraded or recycled. Armitage (1994) *Curr. Opin. Immunol.* 6:407–413; and Fiers (1991) *FEBS Lett.* 285:199–212.

TNF binding proteins (TNF-BP) were originally identified in the serum and urine of febrile patients, individuals with renal failure, cancer patients, and even certain healthy individuals. Seckinger et al. (1988) *J. Exp. Med.* 167:1511–1516; Engelmann et al. (1989) *J. Biol. Chem.* 264:11974–11980; Seckinger et al. (1989) *J. Biol. Chem.* 264:11966–11973; Peetre et al. (1988) *Eur. J. Haematol.* 41:414–419; Olsson et al. (1989) *Eur. J. Haematol.* 42:270–275; Gatanaga et al. (1990a) *Lymphokine Res.* 9:225–229; and Gatanaga et al. (1990b) *Proc. Natl. Acad. Sci USA* 87:8781–8784. In fact, human brain and ovarian tumors produced high serum levels of TNF-BP. Gatanaga et al. (1990a); and Gatanaga et al. (1990b). These molecules were subsequently purified, characterized, and cloned by different laboratories. Gatanaga et al. (1990b); Olsson et al. (1989); Schall et al. (1990) *Cell* 61:361–370; Nophar et al. (1990) *EMBO J.* 9:3269–3278; Himmler et al. (1990) *DNA*

Cell Biol. 9:705–715; Loetscher et al. (1990) Cell 61:351–359; and Smith et al. (1990) Science 248:1019–1023. These proteins have been suggested for use in treating endotoxic shock. Mohler et al. (1993) J. Immunol. 151:1548–1561; Porat et al. (1995) Crit. Care Med. 23:1080–1089; Fisher et al. (1996) N. Engl. J. Med. 334:1697–1702; Fenner (1995) Z. Rheumatol. 54:158–164; and Jin et al. (1994) J. Infect. Dis. 170:1323–1326.

Human TNF-BP consist of 30 kDa and 40 kDa proteins found to be identical to the N-terminal extracellular domains of p55 and p75 TNF-R, respectively. The 30 kDa and 40 kDa TNF-BP are thus also termed soluble p55 and p75 TNF-R, respectively. Studies of these proteins have been facilitated by the availability of human recombinant 30 kDa and 40 kDa TNF-BP and antibodies which specifically recognize each form and allow quantitation by immunoassay. Heller et al. (1990) Proc. Natl. Acad. Sci. USA 87:6151–6155; U.S. Pat. No. 5,395,760; EP 418,014; and Grosen et al. (1993) Gynecol. Oncol. 50:68–77. X-ray structural studies have demonstrated that a TNF trimer binds with three soluble TNF-R (sTNF-R) molecules and the complex can no longer interact with TNF-R. Banner et al. (1993) Cell 73:431–445. The binding of the trimer and sTNF-R, however, is reversible and these reactants are not altered as a result of complex formation. At high molar ratios of sTNF-R to TNF, both recombinant and native human sTNF-R are potent inhibitors of TNF/LT biological activity in vitro as well as in vivo. Gatanaga et al. (1990b); Ashkenazi et al. (1991) Proc. Natl. Acad. Sci. USA 88:10535–10539; Lesslaur et al. (1991) Eur. J. Immunol. 21:2883–2886; Olsson et al. (1992) Eur. J. Haematol. 48:1–9; and Kohno et al. (1990) Proc. Natl. Acad. Sci. USA 87:8331–8335.

Increased levels of TNF-R are also associated with clinical sepsis (septic peritonitis), HIV-1 infection, and other inflammatory conditions. Kalinkovich et al. (1995) J. Interferon and Cyto. Res. 15:749–757; Calvano et al. (1996) Arch. Surg 131:434–437; and Ertel et al. (1994) Arch. Surg. 129:1330–1337. Sepsis, and septic shock affect thousands of patients every year and there is essentially no cure. This lethal syndrome is caused primarily by lipopolysaccharides (LPS) of Gram-negative bacteria and superantigens of Gram-positive bacteria. Clinical symptoms are initiated primarily by the release of endogenous mediators, such as TNF, from activated lymphoid cells into the bloodstream. TNF induces production of a cascade of other cytokines, including IL-1, gamma-Interferon, IL-8, and IL-6. These cytokines, along with other factors, promote the clinical symptoms of shock. Recombinant human sTNF-R is currently being tested in clinical trials to block TNF/LT activity in patients with septic shock and other conditions in which TNF and LT are thought to be pathogenic. Van Zee et al. (1992) Proc. Natl. Acad. Sci. USA 89:4845–4849. Balb/c mice, the primary animal model, and multiple techniques have been used to test the effects of TNF modulators and other treatments on septic peritonitis. Jin et al. (1994) J. Infect. Dis. 170:1323–1326; Mohler et al. (1993) J. Immunol. 151:1548–1561; Porat et al. (1995) Crit. Care Med. 23:1080–1089; and Echtenacher et al. (1996) Nature 381:75–77. Lipopolysaccharide-induced shock has been shown to be ameliorated by FR167653, a dual inhibitor of IL-1 and TNF production. Yamamoto et al. (1997) Eur. J. Pharmacol. 327:169–174.

Attempts have been made to ameliorate the untoward effects of TNF by treatment with monoclonal antibodies to TNF or with other proteins that bind TNF, such as modified TNF receptors. Patients with sepsis or septic shock were treated with anti-TNF antibodies. Salat et al. (1997) Shock 6:233–7. Some improvement in the clinical and histopathologic signs of Crohn's disease were afforded by treatment with anti-TNF antibodies. Neurath et al. (1997) Eur. J. Immun. 27:1743–50; van Deventer et al. (1997) Pharm. World Sci. 19:55–9; van Hogezand et al. (1997) Scand J. Gastro. 223:105–7; and Stack et al. (1997) Lancet 349:521–4. In the treatment of experimental autoimmune encephalitis (EAE), an animal model of the human disease multiple sclerosis (MS), treatment with TNF-R fusion protein prevents the disease and the accompanying demyelination, suggesting the possible use of this treatment in MS patients. Klinkert et al. (1997) J. Neuroimmun. 72:163–8. Neither coagulation nor the fibrinolytic system was affected by an anti-TNF antibody in a study of patients with sepsis or septic shock. Satal et al. (1996) Shock 6:233–7.

Regulation of TNF expression is being tested in treatment of endotoxic shock. Mohler et al. (1994) Nature 370:218–220. Modulation of TNF-R activity is also being approached by the use of peptides that bind intracellularly to the receptor or other component in the process to prevent receptor shedding. PCT patent publications: WO 95/31544, WO 95/33051; and WO 96/01642. Modulation of TNF-R activity is also postulated to be possible by binding of peptides to the TNF-R and interfering with signal transduction induced by TNF. European Patent Application EP 568 925.

While low levels of sTNF-R have been identified in the sera of normal individuals, high levels have been found in the sera of patients with chronic inflammation, infection, renal failure and various forms of cancer. Aderka et al. (1992) Lymphokine Cytokine Res. 11:157–159; Olsson et al. (1993) Eur. Cytokine Netw. 4:169–180; Diez-Ruiz et al. (1995) Eur. J. Haematol. 54:1–8; van Deuren (1994) Eur. J. Clin. Microbiol. Infect. Dis. 13 Suppl. 1:S12–6; Lambert et al. (1994) Nephrol. Dial. Transplant. 9:1791–1796; Halwachs et al. (1994) Clin. Investig. 72:473–476; Gatanaga et al. (1990a); and Gatanaga et al. (1990b). Serum levels of sTNF-R rise within minutes and remain high for 7 to 8 hours after the intravenous injection of human recombinant TNF or IL-2 into human cancer patients. Aderka et al. (1991) Cancer Res. 51:5602–5607; and Miles et al. (1992) Br. J. Cancer 66:1195–1199. Contrarily, serum sTNF-R levels are chronically elevated in cancer patients and may remain at high levels for years. Grosen et al. (1993). It is clear that sTNF-R are natural inhibitors of these cytokines and regulate their biological activity post secretion. Fusion proteins consisting of a sTNF-R linked to a portion of the human IgG1 have also been developed for treating rheumatoid arthritis and septic shock. Moreland et al. (1997) N. Eng. J. Med. 337:141–7; Abraham et al. (1997) JAMA 277:1531–8.

New evidence has yielded information on cellular regulation of secreted cytokines. The evidence indicates that cells release molecules which resemble or contain the binding site of the specific membrane receptors. Massague and Pandiella (1993) Annu. Rev. Biochem. 62:515–541; and Rose-John and Heinrich (1994) Biochem. J. 300:281–290. These soluble forms specifically bind and, in the appropriate molar ratios, inactivate the cytokine by steric inhibition. Therefore, this may be a general phenomenon responsible for the regulation of cytokines and membrane antigens.

Notably, in addition to TNF-R, various types of membrane molecules have both soluble and membrane forms, including (i) cytokine receptors, e.g., IL-1R, IL-2R, IL-4R, IL-5R, IL-6R, IL-7R, IL-9R, granulocyte-colony stimulating factor-R (G-CSF-R), granulocyte-macrophage-colony stimulating factor-R (GM-CSF-R), transforming growth factor-β-R (TGFβ-R), platelet-derived growth factor-R (PDGF-R), and epidermal growth factor-R (EGF-R); (ii) growth factors, e.g., TNF-(pro-TNF-α), TGF-α, and CSF-1; (iii) adhesion molecules, e.g., intracellular adhesion molecule-1 (ICAM-1/CD54) and vascular cell membrane adhesion molecule (VCAM-1/CD106); (iv) TNF-R/NGF-R superfamily, e.g., LNGF-R, CD27, CD30, and CD40; and (v) other membrane proteins, e.g. transferrin receptor, CD14 (receptor for LPS and LPS binding protein), CD16 (FcγRIII), and CD23 (low-affinity receptor for IgE). Colotta et al. (1993) *Science* 261:472–475; Baran et al. (1988) *J. Immunol.* 141:539–546; Mosley et al. (1989) *Cell* 59:335–348; Takaki et al. (1990) *EMBO J.* 9:4367–4374; Novick et al. (1989) *J. Exp. Med.* 170:1409–1414; Goodwin et al. (1990) *Cell* 60:941–951; Renauld et al. (1992) *Proc. Natl. Acad Sci. USA* 89:5690–5694; Fukunaga et al. (1990) *Proc. Natl. Acad. Sci. USA* 87:8702–8706; Raines et al. (1991) *Proc. Natl. Acad. Sci. USA* 88:8203–8207; Lopez-Casillas et al. (1991) *Cell* 67:785–795; Tiesman and Hart (1993) *J. Biol. Chem.* 268:9621–9628; Khire et al. (1990) *Febs. Lett.* 272:69–72; Kriegler et al. (1988) *Cell* 53:45–53; Pandiella and Massague (1991) *Proc. Natl. Acad. Sci. USA* 88:1726–1730; Stein et al. (1991) *Oncogene* 6:601–605; Seth et al. (1991) *Lancet* 338:83–84; Hahne et al. (1994) *Eur. J. Immunol.* 24:421–428; Zupan et al. (1989) *J. Biol. Chem.* 264:11714–11720; Loenen et al. (1992) *Eur. J. Immunol.* 22:447–455; Latza et al. (1995) *Am. J. Pathol.* 146:463–471; Chitambar (1991) *Blood* 78:2444–2450; Landmann et al. (1992) *J. Leukoc. Biol.* 52:323–330; Huizinga et al. (1988) *Nature* 333:667–669; and Alderson et al. (1992) *J. Immunol.* 149:1252–1257.

In vitro studies with various types of cells have revealed that there are two mechanisms involved in the production of soluble receptors and cell surface antigens. One involves translation from alternatively spliced mRNAs lacking transmembrane and cytoplasmic regions, which is responsible for the production of soluble IL-4R, IL-5R, IL-7R, IL-9R, G-CSF-R, and GM-CSF-R. Rose-John and Heinrich (1994); and Colotta et al. (1993). The other mechanism involves proteolytic cleavage of the intact membrane receptors and antigens, known as shedding. Proteolysis appears to be involved in the production of soluble LNGF-R, TNF-R, CD27, CD30, IL-1R, IL-6R, TGFβ-R, PDGF-R, and CD14 (Id.).

Matrix metalloproteinases (MMPs) are a family of enzymes that includes interstitial collagenase (MMP-1), 72 kDa and 92 kDa gelatinases (MMP-2 and MMP-9), stromelysins 1, 2 and 3, neutrophil collagenase, metalloelastase, matrilysin, and gelatinase A. These enzymes are secreted by cells within tissues and by infiltrating inflammatory cells. Collectively, they are capable of degrading most of the proteins in the extracellular matrix (ECM).

MMPs display different substrate specificities yet have several properties in common. They are all zinc-containing enzymes that require calcium for activity. They are secreted as zymogens and activated in situ, usually by release of an inhibitory N-terminal pro-piece containing a single cysteine residue. The attached pro-piece is believed to coordinate with the zinc in the active site of the proteinase, thereby suppressing the proteolytic activity. Activation may be accompanied by additional proteolytic cleavages that can generate active enzymes of lower molecular weights. All members of the MMP family have a short conserved region consisting of the HEXGH motif that provides two Zn-coordinating histidine residues and a glutamic acid residue that is considered part of the catalytic site. With few exceptions, MMPs also contain a hemopexin/vitronectin domain. The function of the hemopexin domain is unknown. For review see Ray and Stetter-Stevenson (1994) *Eur. Respir. J.* 7:2062–2072.

A variety of studies have indicated that MMPs are involved in tumor invasion and metastasis. A number of methods have been utilized to assess the presence of MMPs in human tumor tissues and serum from cancer patients. Positive correlations have been found between MMP expression and tumor invasion and metastasis in vitro, as well as in in vivo animal models. Matrisian et al. (1991) *Am. J. Med. Sci.* 302:157–162; Sato et al. (1992) *Oncogene* 7:77–83; Lyons et al. (1991) *Biochemistry* 30:1449–1456; Levy et al. (1991) *Cancer Res.* 51:439–444; Bonfil et al. (1989) *J. Natl. Cancer Inst.* 81:587–594; Sreenath et al. (1992) *Cancer Res.* 52:4942–4947; and Powell et al. (1993) *Cancer Res.* 53:415–422. MMPs have been associated with the malignant phenotype in a wide variety of human tissues, including lung, prostate, stomach, colon, breast, ovaries and thyroid, as well as squamous carcinoma of the head and neck. Matrisian et al. (1991); Sato et al. (1992); Levy et al. (1991); and Lyons et al. (1991). To date, the proposed role of MMPs in cancer has been limited to tissue remodeling in invasion and metastasis.

The MMPs are inhibited by members of the family of tissue inhibitors of metalloproteinases (TIMPs, e.g., TIMP-1, TIMP-2, and TIMP-3), which bind at the active site and block access to substrate. Matrix remodeling, which occurs during various normal and pathological processes depends on a critical balance between activated MMPs and inhibiting TIMPs. For reviews of MMPs and their inhibitors see Alexander and Werb (1991), *In: Cell Biology of Extracellular Matrix*, ed. Hay, Plenum Press, New York, pp. 205–302; Murphy et al. (1991) *Br. J. Rheumatol.* 30:25–31; Woessner (1991) *FASEB J.* 5:2145–2154; Matrisian (1992) *Bioessays* 14:455–463; Birkedal-Hansen et al. (1993) *Crit. Rev. Oral Biol. and Med.* 4:197–250; and Denhardt et al. (1993) *J. Pharmacol. Ther.* 59:329–341.

Recent studies suggest that metalloproteases may be involved in the cleavage of both TNF-Rs, LNGF-R, IL-6R, pro-TNF-α, VCAM-1, and CD30 and are thereby responsible for the production of the soluble forms. Crowe et al. (1995) *J. Exp. Med.* 181:1205–1210; Mullberg et al. (1995) *J. Immunol.* 155:5198–5205; Bjornberg et al. (1995) *Scand. J. Immunol.* 42:418–424; DiStefano et al. (1993) *J. Neurosci.* 13:2405–2414; Mohler et al. (1994) *Nature* 370:218–220; Gearing et al. (1994) *Nature* 370:555–557; McGeehan et al. (1994) *Nature* 370:558–561; Leca et al. (1995) *J. Immunol.* 154:1069–1077; and Hansen et al. (1995) *Int. J. Cancer* (1995) 63:750–756. Interestingly, a MMP is suggested to be responsible for the cleavage of pro-TNF-α. Gearing et al. (1994); and Gearing et al. (1995) *J. Leukoc. Biol.* 57:774–777. In addition, levels of serum matrix metalloproteinase 1 and 3 in rheumatoid arthritis patients were reduced following anti-TNF antibody therapy. Brennan et al. (1997) *Br. J. Rheumatology* 36:643–50. Anti-TNF antibodies have also been used to suppress fever, inflammation and the acute-phase response in juvenile chronic arthritis and rheumatoid arthritis cases, and to reverse endotoxin shock in rats. Elliott et al. (1997) *Br. J. Rheumatology* 36:589–93; Maini et al. (1997) *Apmis* 105:257–63; and Boillot et al. (1997) *Crit. Care Medicine* 25:504–11. One MMP inhibitor, GM-6001, prevents the release of TNF both in vitro and in vivo. Solorzano et al. (1997) *Shock* 7:427–31.

A number of MMP inhibitors have been described and the use thereof has also been suggested for treating various pathologic indications, including: angiogenesis; wound healing; gum disease; skin disorders; keratoconus; inflammatory conditions; rheumatoid arthritis; cancer; corneal and skin ulcers; cardiovascular disease; central nervous system disorders; and diabetes. U.S. Pat. Nos. 5,268,384 and 5,270,326; PCT publications WO 94/22309, WO 95/09913, WO 90/11287, WO 90/14363; EP patents 211 077, 623 676; and Naito et al. (1994) *Int. J. Cancer* 58:730–735; Watson et al. (1995) *Cancer Res.* 55:3629–3633; Davies et al. (1993) *Cancer Res.* 53:2087–2091; Brown (1995) *Advan. Enzyme Regul.* 35:293–301; Sledge et al. (1995) *J. Natl. Cancer Inst.* 87:1546–1550; Conway et al (1995) *J. Exp. Med.* 182:449–457; and Docherty et al. (1992) *TibTech* 10:200–207. However, the ability to treat arthritis by inhibiting matrix metalloproteases has been questioned. Vincenti et al. (1994) *Arth. & Rheum.* 37:1115–1126.

Both soluble p55 and p75 TNF-R do not appear to be generated from processed mRNA, since only full length receptor mRNA has been detected in human cells in vitro. Gatanaga et al. (1991). Carboxyl-terminal sequencing of the human soluble p55 TNF-R indicates that a cleavage site may exist between Asn 172 and Val 173. Gullberg et al. (1992) *Eur. J. Cell Biol.* 58:307–312. This evidence is supported by the finding that human TNF-R with the mutation at Asn 172 and Val 173 was not released as effectively as native TNF-R on COS-1 cells transduced with cDNA of human TNF-R. Gullberg et al. (1992). The cytoplasmic portion of TNF-R does not appear to play an important role in releasing the soluble receptor forms from transduced COS-1 cells. COS-1 cells release sTNF-R even when transduced with cDNA of human p55 TNF-R which expresses only the extracellular domain but not the cytoplasmic domain. (Id.) sTNF-R shedding is not affected by dexamethasone, gold sodium thiomalate, or prostaglandin E2. Seitz et al. (1997) *J. Rheumatology* 24:1471–6. Collectively, these data support the concept that human sTNF-R are produced by proteolytic cleavage of membrane TNF-R protein.

It would be useful to purify and characterize the protease that cleaves TNF-R and results in the generation of sTNF-R. The purification and characterization of this proteinase will reveal the role of sTNF-R in host-tumor interactions and in treatment of pathogenic conditions mediated or exacerbated by TNF. Although claims have been made to the TRRE (EP 657 536), analysis of the claimed protein sequences given by BLAST Protein Sequence Homology Search reveals that they match the TNF-R. This may be due to the use of a TNF-R affinity column during protein purification. Thus, the nature of the protein and its DNA and AA sequences have not yet been elucidated.

In spite of numerous advances in medical research, cancer remains the second leading cause of death in the United States. In the industrialized nations, roughly one in five persons will die of cancer. Traditional modes of clinical care, such as surgical resection, radiotherapy and chemotherapy, have significant failure rates, especially for solid tumors. Failure occurs either because the initial tumor is unresponsive, or because of recurrence due to regrowth at the original site and/or metastases. Even in cancers such as breast cancer where the mortality rate has decreased, successful intervention relies on early detection of the cancerous cells. The etiology, diagnosis and ablation of cancer remain a central focus for medical research and development.

Neoplasia resulting in benign tumors can usually be completely cured by removing the mass surgically. If a tumor becomes malignant, as manifested by invasion of surrounding tissue, it becomes much more difficult to eradicate. Once a malignant tumor metastasizes, it is much less likely to be eradicated.

The three major cancers, in terms of morbidity and mortality, are colon, breast and lung. New surgical procedures offer an increased survival rate for colon cancer. Improved screening methods increase the detection of breast cancer, allowing earlier, less aggressive therapy. Lung cancer remains largely refractory to treatment.

Excluding basal cell carcinoma, there are over one million new cases of cancer per year in the United States alone, and cancer accounts for over one half million deaths per year in this country. In the world as a whole, the five most common cancers are those of lung, stomach, breast, colon/rectum, and uterine cervix, and the total number of new cases per year is over 6 million. Only about half the number of people who develop cancer die of it.

Melanoma is one of the human diseases for which there is an acute need of new therapeutic modalities. It is a particularly aggressive form of skin cancer, and occurs in increased frequency in individuals with regular unguarded sun exposure. In the early disease phases, melanoma is characterized by proliferation at the dermal-epidermal junction, which soon invades adjacent tissue and metastasizes widely. Once it has metastasized, it is often impossible to extirpate and is consequently fatal. Worldwide, 70,000 patients are diagnosed annually with melanoma and it is responsible for 25,000 reported deaths each year. The American Cancer Society projects that by the year 2000, 1 out of every 75 Americans will be diagnosed with melanoma.

Neuroblastoma is a highly malignant tumor occurring during infancy and early childhood. Except for Wilm's tumor, it is the most common retroperitoneal tumor in children. This tumor metastasizes early, with widespread involvement of lymph nodes, liver, bone, lung, and marrow. While the primary tumor is resolvable by resection, the recurrence rate is high.

Small cell lung cancer is the most malignant and fastest growing form of lung cancer and accounts for 20–25% of new cases of lung cancer. Approximately 60,000 cases are diagnosed in the U.S. every year. The primary tumor is generally responsive to chemotherapy, but is followed by wide-spread metastasis. The median survival time at diagnosis is approximately 1 year, with a 5 year survival rate of 5–10%.

Breast cancer is one of the most common cancers and is the third leading cause of death from cancers in the United States with an annual incidence of about 182,000 new cases and nearly 50,000 deaths. In the industrial nations, approximately one in eight women can expect to develop breast cancer. The mortality rate for breast cancer has remained unchanged since 1930. It has increased an average of 0.2% per year, but decreased in women under 65 years of age by an average of 0.3% per year. Preliminary data suggest that breast cancer mortality is beginning to decrease, probably as a result of increased diagnoses of localized cancer and carcinoma in situ. See e.g., Marchant (1994) Contemporary Management of Breast Disease II: Breast Cancer, In: *Obstetrics and Gynecology Clinics of North America* 21:555–560; and Colditz (1993) *Cancer Suppl.* 71:1480–1489.

Non-Hodgkin's B cell lymphomas are cancers of the immune system that are expected to afflict approximately 225,000 patients in the United States in 1996. These cancers are diverse with respect to prognosis and treatment, and are generally classified into one of three grades. The median survival of the lowest grade is 6.6 years and the higher grade cancers have much lower life expectancy. Virtually all non-Hodgkin's B cell lymphomas are incurable. New diagnoses of non-Hodgkins lymphomas have increased approximately 7% annually over the past decade, with 52,700 new diagnoses estimated for 1996. The increase is due in part to the increasing prevalence of lymphomas in the AIDS patient population.

In spite of the difficulties, effective cures using anticancer drugs (alone or in combination with other treatments) have been devised for some formerly highly lethal cancers. Most notable among these are Hodgkin's lymphoma, testicular cancer, choriocarcinoma, and some leukemias and other cancers of childhood. For several of the more common cancers, early diagnosis, appropriate surgery or local radiotherapy enables a large proportion of patients to recover.

Current methods of cancer treatment are relatively non-selective. Surgery removes the diseased tissue, radiotherapy shrinks solid tumors and chemotherapy kills rapidly dividing cells. Chemotherapy, in particular, results in numerous side effects, in some cases severe enough to preclude the use of potentially effective drugs. Moreover, cancers often develop resistance to chemotherapeutic drugs.

Recently, a method of in situ treatment of cancers, particularly pancreas, has been shown to be efficacious. The method involves creating an mixed lymphocyte reaction (MLR) between the host (cancer patient's) peripheral blood lymphocytes and a donor's allogeneic lymphocytes and administering the MLR directly to the tumor. This method is described more fully, for example, in WO 93/20186 and JP 62096426. In the case of large solid tumors, administration of the MLR is preceded by resection of the tumor.

Like cancers, weight problems are also associated with TNF. TNF is linked to the three factors contributing to body weight control: intake, expenditure, and storage of energy. Administration of either TNF or IL-1, for example, induces a decrease in food intake. Rothwell (1993) *Int. J. Obesity* 17:S98–S101; Arbos et al. (1992) *Mol. Cell. Biochem.* 112:53–59; Fargeas et al. (1993) *Gastroenterology* 104:377–383; Plata-Salaman et al. (1994) *Am. J. Physiol.* 266:R1711–1715; Schwartz et al. (1995) *Am. J. Physiol.* 269:R949–957; and Oliff et al. (1987) *Cell* 50:555–563. Interestingly, TNF may have a key roles in both extremes of weight problems. Abnormalities in its activity may lead to obesity; changes in its production result in the opposite effect, cachexia. Argilés et al. (1997) *FASEB J.* 11:743–751.

Cachexia is pathological weight loss generally associated with anorexia, weakness, anemia, asthenia, and loss of body lipid stores and skeletal muscle protein. This state often accompanies burns, trauma, infection, and neoplastic diseases. Lawson et al. (1982) *Annu. Rev. Nutr.* 2:277–301; Argilés et al. (1988) *Mol. Cell. Biochem.* 81:3–17; and Ogiwara et al. (1994) *J. Surg. Oncol.* 57:129–133. TNF concentrations are elevated in many patients with cachexia. Scuderi et al. (1986) *Lancet* 2:1364–65; Grau et al. (1987) *Science* 237:1210–1212; and Waage et al. (1986) *Scand. J. Immunol.* 24:739–743. TNF inhibits collagen alpha I gene expression and wound healing in a murine model of cachexia. Buck et al. (1996) *Am. J. Pathol.* 149:195–204. In septicemia (the invasion of bacteria into the bloodstream), increased endotoxin concentrations may raise TNF levels, causing cachexia. Beutler et al. (1985) *Science* 229:869–871; Tracey et al. (1987) *Nature* 330:662–664; and Michie et al. (1988) *New Engl. J. Med.* 318:1481–1486. During cachexia, the loss of white adipose tissue is caused by the decreased activity of lipoprotein lipase (LPL); TNF lowers the activity of this enzyme. Price et al. (1986) *Arch. Biochem. Biophys.* 251:738–746; Cornelius et al. (1988) *Biochem. J.* 249:765–769; Fried et al. (1989) *J. Lipid. Res.* 30:1917–1923; Semb et al. (1987) *J. Biol. Chem.* 262:8390–8394; and Evans et al. (1988) *Biochem. J.* 256:1055–1058. Fat tissue loss is also associated with an increase in lipase activity and inhibition of glucose transport; TNF is also linked to both of these changes. Kawakami et al. (1987) *J. Biochem.* 331–338; Feingold et al. (1992) *Endocrinology* 130:10–16; and Hauner et al. (1995) *Diabetologia* 38:764–771. TNF mediates hypertriglyceridaemia associated with cachexia. Dessi et al. (1995) *Br. J. Cancer* 72:1138–43. TNF also participates in the protein wasting, loss of skeletal muscle and loss of nitrogen associated with cachexia. Costelli et al. (1993) *J. Clin. Invest.* 92:2783–2789; Flores et al. (1989) *J. Clin. Invest.* 83:1614–1622; Goodman (1991) *Am. J. Physiol.* 260:E727–730; Zamir et al. (1992) *Arch. Surg.* 127:170–174; Llovera et al. (1993) *J. Natl. Cancer Inst. USA* 85:1334–1339; and Garcia-Martinez et al. (1993) *FEBS Lett.* 323:211–214.

TNF has additional, related roles. It is involved in thermogenesis, particularly nonshivering thermogenesis in brown adipose tissue (BAT), which has an elevated level in cachexia. Nicholls (1983) *Biosci. Rep.* 3:431–441; Rothwell (1993) *Int. J. Obesity* 17:S98–S101; Bianchi et al. (1989) *Horm. Metab. Res.* 21:11; and Oudart et al. (1995) *Can. J. Physiol. Pharmacol.* 73:1625–1631. TNF has also been implicated in non-insulin-dependent (type II) diabetes. Hotamisligil et al. (1995) *J. Clin. Invest.* 95:2409–2415; Arner (1996) *Diabetes Metab.* 13:S85–S86; Spiegelman et al. (1993) *Cell* 73:625–627; Saghizadeh et al. (1996) *J. Clin. Invest.* 97:1111–16; and Hofmann et al. (1994) *Endocrinology* 134:264–270. These data help explain how TNF mediates the opposite effects of obesity and cachexia. TNF has functional similarities to those of leptin, which has been proposed to be an "adipostat." Zhang et al. (1994) *Nature* 372:425–432; Phillips et al. (1996) *Nature Genet.* 13:18–19; and Madej et al. (1995) *FEBS Lett.* 373:13–18. Like leptin, for example, TNF is expressed and secreted by adipocytes and can travel to the brain. TNF administration also results in an increase in circulating leptin concentrations. Grunfeld et al. (1996) *J. Clin. Invest.* 97:2152–57. It is possible to reconcile the participation of TNF in obesity and cachexia. TNF can be considered one of many signals coming from adipose tissue that participate in the feedback mechanism that informs the hypothalamic center about the state of the adipocyte energy depot. It probably counteracts excessive energy intake and is able to stimulate thermogenesis either directly or by increasing sympathetic activity. TNF released by adipose tissue will also stimulate lipolysis, decrease LPL activity, decrease the expression of the glucose transporter GLUT4, and inhibit lipogenesis in the adipocyte, thus contributing to the maintenance (but not increased fat deposition) of the adipose tissue mass. In cachexia, however, the situation is different. A high production of TNF by activated macrophages (as a result of a tumor or an infection) also contributes to anorexia, increased thermogenesis, and adipose tissue dissolution. However, it represents a pathological state where there is an excess of the molecules that inform the brain that adipose tissue needs dissolution. The two situations can thus be reconciled: in cachexia there is a pathological overproduction of TNF; in obesity, the physiological action of TNF as a signal to control food intake and energy expenditure is impaired. Argilés et al. (1997). *FASEB J.* 11:743–751.

SUMMARY OF THE INVENTION

The invention encompasses compositions of a substantially purified protein having tumor necrosis factor receptor (TNFR) releasing enzymatic activity, termed TRRE. The protein can be purified by any method known in the art, preferably as described in the examples below. In one embodiment, the TRRE in its native form has an apparent molecular weight of about 120 kDa on sodium dodecyl sulfate polyacrylamide gel electrophoresis (SDS-PAGE). In another embodiment of the present invention, the TRRE has internal amino acid sequences of: D-L-N-L-G-A-Q-A-T-I-T-N-L-P (SEQ ID NO:1); G-L-D-E-T-Q-N-L-I-T-V-P-Y (SEQ ID NO:2); S-E-R-W-P-Q-M-A-N-K-V-S-R (SEQ ID NO:3); I-V-V-T-K (SEQ ID NO:4); E-F-P-H/S-P-V-D-A-A-T-R (SEQ ID NO:5); A-L-F-E-L-I-Y-E-L-L-L/E-A-Y-I-I/N-V-L (SEQ ID NO:6); L-D-Y-Q-E/T-S-Y-S-A-A-V-A-R (SEQ ID NO:7); L-A-L-Q/I-E-S-P-S/P (SEQ ID NO:8); L-F-L-K-N-T-G-L-A-R (SEQ ID NO:9); M-A-L-Q-K-G-D-R (SEQ ID NO:10); K-L-L-E-L-N-V-V-A (SEQ ID NO:11); V/I-T-D-M-V-V-G-I-X-G (SEQ ID NO:12) where X is an unidentified amino acid residue; L-V-D-Y-D-X-L-F-Q-N-L (SEQ ID NO:13); and/or K-E-A-L-I-A-K-I-R (SEQ ID NO:14). Alternatively, in another embodiment of the present invention, the TRRE in its native form has an apparent molecular weight of about 60 kDa on SDS-PAGE. In another embodiment, the TRRE has internal amino acid sequences of D-L-N-L-G-A-Q-A-T-I/L-T-N-L-P (SEQ ID NO:15); L-A-E-D-Y-L-S-G/L-W-L-E/G-R (SEQ ID NO:16); and/or L/K-V/L-D/E-Y-D/E-X-L/F-F-Q-N-L (SEQ ID NO:17). Fragments of TRRE containing TRRE activity are also encompassed by the invention.

The invention further encompasses methods of treating a disease associated with altered levels or activities of tumor necrosis factor. The methods include the steps of administering an amount of TRRE sufficient to indirectly moderate or modulate local levels of tumor necrosis factor.

The invention likewise encompasses methods of treating a disease associated with elevated levels of soluble TNF-R. The method includes administering an amount of an inhibitor of TRRE effective to decrease the levels of soluble TNF-R.

The invention also encompasses methods of diagnosing a disease associated with elevated levels of TRRE, comprising obtaining a biological sample from a patient; measuring activity of TRRE in the sample and comparing the measured activity to the TRRE activity of a control biological sample. Excess TRRE activity compared to control is indicative of the presence of a disease state associated with elevated levels of TRRE.

The invention further encompasses methods of treating a disease associated with decreased levels of tumor necrosis factor. The methods include the steps of administering an amount of an inhibitor of TRRE sufficient to modulate the levels of TNF-TNF receptor complexes on cell surfaces.

The invention also encompasses a method for measuring TRRE activity. The method comprises the steps of comparing TNF-R release in TNF-R expressing cells (TNF-R$^+$) incubated with TRRE to TNF-R release by TNF-R$^+$ cells not incubated with TRRE and to TNF-R release by cells that do not express significant amounts of TNF-R (TNF-R$^-$). The amount of TNF-R released by the TNF-R$^+$ cells incubated with TRRE minus the amount of TNF-R released by the TNF-R$^+$ cells without TRRE and the amount of TNF-R released by TNF-R$^-$ cells yields the amount of TRRE in a sample. Preferably the TNF-R$^+$ cells are recombinant TNF-R$^-$ cells transformed to express TNF-R recombinantly.

The invention further encompasses methods for screening for agents that modulate the activity of TRRE. The activity of TREE is measured in the presence (test) or absence (control) of a particular agent or drug. If the activity of the test sample exceeds or is less than that of the control, the agent or drug increases or decreases, respectively, TRRE activity.

BRIEF DESCRIPTION OF THE DRAWINGS

FIG. 3 is a bar graph depicting the effect of TRRE on TNF binding to C75R.

FIG. 4 depicts the results of Western Blot analysis of soluble receptors released from C75R cells by TRRE.

FIG. 5A depicts the short course (5–30 minutes) and FIG. 5B depicts the long course (30–90 minutes).

DETAILED DESCRIPTION OF THE INVENTION

Figure 1:
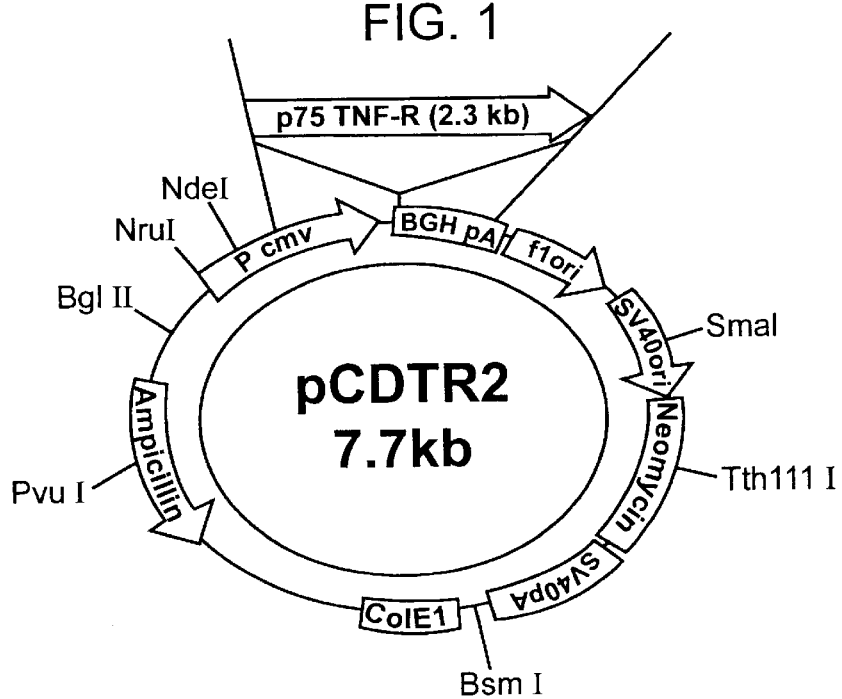
FIG. 1 is a schematic representation of plasmid pCDTR2 which expresses p75 TNF-R. PCMV stands for cytomegalovirus; BGHpA stands for bovine growth hormone polyadenylation signal.

TNF is a major proinflammatory and immunomodulatory cytokine produced during immune responses. TNF also regulates the expression of IL-2R leading to enhanced T cell responses mediated by IL-2 and appears to be required for generating proliferative responses in mixed lymphocyte cultures. Additional studies have shown that $CD8^+$, CTL and lymphokine activated killer cells are optimally induced with TNF, in combination with IL-2, suggesting the importance of this cytokine in regulating cytotoxic effector function. As discussed in detail above, TNF mediates its activity by binding to a TNF-R. Soluble TNF-Rs inhibit TNF activity by two methods: they decrease the available binding sites on a cell and bind to soluble TNF to decrease the local concentration. The present invention encompasses compositions and methods for modulating the level of soluble TNF-R by decreasing the cleavage of TNF-R from the cell surface and thus indirectly modulating the effect of TNF.

In this invention, a novel assay system was devised to detect and quantitate TRRE, resulting in the generation of sTNF-R. This proteolytic activity, induced from PMA-stimulated THP-1 cells (a human tumor monocytic cell line) into culture medium, was defined as TNF-R releasing enzyme (TRRE). Based on this assay system, TRRE was characterized and purified. The invention further encompasses the TRRE assay discussed in more detail below.

The invention encompasses compositions of a substantially purified protein having tumor necrosis factor receptor (TNFR) releasing enzymatic activity, termed TRRE. The protein can be purified as described in the examples below and, in addition to having the described enzymatic activity, the native enzyme has an apparent molecular weight of about 120 kDa on SDS-PAGE. In some embodiments of the present invention, the TRRE has internal amino acid sequences of: D-L-N-L-G-A-Q-A-T-I-T-N-L-P (SEQ ID NO:1); G-L-D-E-T-Q-N-L-I-T-V-P-Y (SEQ ID NO:2); S-E-R-W-P-Q-M-A-N-K-V-S-R (SEQ ID NO:3); I-V-V-T-K (SEQ ID NO:4); E-F-P-H/S-P-V-D-A-A-T-R (SEQ ID NO:5); A-L-F-E-L-I-Y-E-L-L-L/E-A-Y-I-I/N-V-L (SEQ ID NO:6); L-D-Y-Q-E/T-S-Y-S-A-A-V-A-R (SEQ ID NO:7); L-A-L-Q/I-E-S-P-S/P (SEQ ID NO:8); L-F-L-K-N-T-G-L-A-R (SEQ ID NO:9); M-A-L-Q-K-G-D-R (SEQ ID NO:10); K-L-L-E-L-N-V-V-A (SEQ ID NO:11); V/I-T-D-M-V-V-G-I-X-G (SEQ ID NO:12) where X is an unidentified amino acid residue; L-V-D-Y-D-X-L-F-Q-N-L (SEQ ID NO:13); and K-E-A-L-I-A-K-I-R (SEQ ID NO:14). Alternatively, the TRRE in its native form has an apparent molecular weight of about 60 kDa on SDS-PAGE. In some embodiments of the present invention, the TRRE has internal amino acid sequences of D-L-N-L-G-A-Q-A-T-I/L-T-N-L-P (SEQ ID NO:15); L-A-E-D-Y-L-S-G/L-W-L-E/G-R (SEQ ID NO:16); and L/K-V/L-D/E-Y-D/E-X-L/F-F-Q-N-L (SEQ ID NO:17) where X is an unidentified amino acid residue. The banding pattern on SDS-PAGE is somewhat diffuse, indicating that the protein may be a glycoprotein. Thus, recombinant proteins (i.e. "non-native" proteins) may have differing apparent molecular weights depending on the degree of glycosylation.

The enzymatic activity of the TRRE is inhibited by metalloprotease inhibitors. Thus, the method of inhibiting the activity of TRRE by the addition of metalloprotease inhibitors is also encompassed by the invention.

The terms "polypeptide", "peptide" and "protein" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling or bioactive component. Unless stated or implied otherwise, the term TRRE includes any polypeptide monomer or polymer with TRRE enzymatic specificity, including the intact TRRE, and smaller and larger functionally equivalent polypeptides, as described herein.

A "fusion polypeptide" is a polypeptide comprising regions in a different position in the sequence than occurs in nature. The regions may normally exist in separate proteins and are brought together in the fusion polypeptide; they may normally exist in the same protein but are placed in a new arrangement in the fusion polypeptide; or they may be synthetically arranged. For instance, as described below, the invention encompasses recombinant proteins that are comprised of a functional portion of TRRE and an antibody. Methods of making these fusion proteins are known in the art and are described, for instance, in WO93/07286.

A "functionally equivalent fragment" of a TRRE polypeptide varies from the native sequence by addition(s), deletion(s), or substitution(s), or any combination thereof, while preserving at least one functional property of the fragment relevant to the context in which it is being used. A functionally equivalent fragment of a TRRE polypeptide typically has the ability to bind membrane bound TNF-R and enzymatically cleave TNF-R to provide soluble TNF-R. Amino acid substitutions, if present, are preferably conservative substitutions that do not deleteriously affect folding or functional properties of the peptide. Groups of functionally related amino acids within which conservative substitutions can be made are glycine/alanine; valine/isoleucine/leucine; asparagine/glutamine; aspartic acid/glutamic acid; serine/threonine/methionine; lysine/arginine; and phenylalanine/tyrosine/tryptophan. Polypeptides of this invention can be in glycosylated or unglycosylated form, can be modified post-translationally (e.g., removal of signal peptide, transmembrane or cytoplasmic regions, acetylation, and phosphorylation) or can be modified synthetically (e.g., by a labeling group).

The invention also encompasses compositions of TRRE and a physiologically acceptable buffer. Suitable physiologically acceptable buffers include, but are not limited to, saline and phosphate buffered saline (PBS). If TRRE is to be administered to an individual, it is preferably at least 80% pure, more preferably it is at least 90% pure, even more preferably it is at least 95% pure and free of pyrogens and other contaminants. In this context, the percent purity is calculated as a weight percent of the total protein content of the preparation, and does not include constituents which are deliberately added to the composition after the TRRE is purified.

The invention further encompasses antibodies (or antigen-binding fragments thereof) specific for TRRE proteins. The compositions contain a therapeutically effective amount of substantially purified antibody binding fragment specific for TRRE. Preferably, the antibody neutralizes TRRE TNF-R releasing activity. Methods of antibody production and isolation are well known in the art. See, for example, Harlow and Lane (1988) *Antibodies: A Laboratory Manual*, Cold Spring Harbor Laboratory, New York. Antibodies can be isolated by any technique suitable for immunoglobulins of this isotype. Purification methods include salt precipitation (for example, with ammonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and anti-immunoglobulin. Anti-TRRE antibodies can also be purified on affinity columns comprising TRRE. Preferably, anti-TRRE antibodies are purified using Protein-A-CL-Sepharose™ 4B chromatography followed by chromatography on a DEAE-Sepharose™ 4B ion exchange column.

The term "antigen-binding fragment" includes any peptide that binds to TRRE in a specific manner. These derivatives include such immunoglobulin fragments as Fab, F(ab')$_2$, Fab', scfv (both monomers and polymeric forms) and isolated H and L chains. Antigen-binding fragments retain the specificity of the intact immunoglobulin, although avidity and/or affinity can be altered.

The antigen-binding fragments (also termed "derivatives" herein) are typically generated by genetic engineering, although they can alternatively be obtained by other methods and combinations of methods. This classification includes, but is not limited to, engineered peptide fragments and fusion peptides. Preferred compounds include polypeptide fragments of the CDRs, antibody fusion proteins comprising cytokine effector components, antibody fusion proteins comprising adjuvants or drugs, and single-chain, V region proteins.

Scfv can be produced either recombinantly or synthetically. For synthetic production of scfv, an automated synthesizer can be used. For recombinant production of scfv, a suitable plasmid containing polynucleotide that encodes the scfv can be introduced into a suitable host cell, either eukaryotic, such as yeast, plant, insect or mammalian cells, or prokaryotic, such as *E. coli*, and the expressed protein can be isolated using standard protein purification techniques.

A particularly useful system for the production of scfvs is plasmid pET-22b(+) (Novagen, Madison, Wis.) in *E. coli*. pET-22b(+) contains a nickel ion binding domain consisting of 6 sequential histidine residues, which allows the expressed protein to be purified on a suitable affinity resin. Another example of a suitable vector is pcDNA3 (Invitrogen, San Diego, Calif.), described above.

The invention also encompasses hybrid antibodies, in which one pair of H and L chains is obtained from a first antibody, while the other pair of H and L chains is obtained from a different second antibody. For purposes of this invention, one pair of L and H chains is from anti-TRRE. In one example, each L-H chain pair binds different epitopes of TRRE. Such hybrids can also be formed using humanized H or L chains. Also encompassed by the invention are peptides in which various immunoglobulin domains have been placed in an order other than that which occurs in nature. Additionally, the antigen-binding fragments of this invention can be used as diagnostic and imaging reagents.

The invention further encompasses polynucleotides encoding antibodies (or fragments thereof) capable of binding to a TRRE polypeptide (or fragments thereof). The polynucleotide can be native or recombinant, and can be incorporated into a vector or plasmid and operably linked to a promoter.

The invention further encompasses methods of treating a disease associated with altered levels or activities of TNF by administering an amount of TRRE sufficient to indirectly reduce local levels of TNF. Suitable indications for treatment include, but are not limited to, diseases such as cancer, obesity and cachexia, autoimmune diseases such as diabetes, juvenile onset rheumatoid arthritis, systemic lupus erythematosus, and other inflammatory conditions, psoriasis, endotoxin shock, rheumatoid arthritis, trauma, and multiple sclerosis. Infections associated with microbial or parasitic infection in which TNF has an important role include, but are not limited to, septic shock and malaria. In addition, TRRE can be used to treat indications previously associated with aberrant MMP expression. As mentioned above, these include, but are not limited to, angiogenesis; wound healing; gum disease; skin disorders; keratoconus; inflammatory conditions; rheumatoid arthritis; cancer; corneal and skin ulcers; cardiovascular disease; central nervous system disorders; and diabetes. Also included are immuno-inflammatory diseases or diseases with an immunological base and a tissue destructive component in which TNF has an important role such as Crohn's disease and inflammatory bowel disease. Other inflammatory conditions such as traumatic shock are also included.

Methods of administration include any known in the art. Preferably, administration is directly to the site of inflammation in the case of rheumatoid arthritis and is parenteral, subcutaneous, intramuscular, intraperitoneal, intracavity, intrathecal, and intravenous in the case of systemic disorders. Administration can also be systemic to treat localized disorders or local to treat systemic disorders. Methods of administration are discussed in more detail below. Local administration can be achieved by, for example, local infusion during surgery, by direct injection to the site, by means of a catheter, or by means of an implant, said implant being of a porous, non-porous, or gelatinous material, including membranes, such as silastic membranes, or fibers. A suitable such membrane is Gliadel® provided by Guilford sciences.

With external ailments such as psoriasis, treatment is by topical application. The invention thus further includes compositions of effective amounts of TRRE and a topical pharmaceutically or cosmetically acceptable carrier.

"Topical pharmaceutically acceptable carrier" as used herein is any substantially non-toxic carrier conventionally useable for topical administration of pharmaceuticals in which TRRE will remain stable and bioavailable when applied directly to skin or mucosal surfaces. For example, TRRE can be dissolved in a liquid, dispersed or emulsified in a medium in a conventional manner to form a liquid preparation or mixed with a semi-solid (gel) or solid carrier to form a paste, powder, ointment, cream, lotion or the like.

Suitable topical pharmaceutically acceptable carriers include water, petroleum jelly (Vaseline™), petrolatum, mineral oil, vegetable oil, animal oil, organic and inorganic waxes, such as microcrystalline, paraffin and ozocerite wax, natural polymers, such as xanthanes, gelatin, cellulose, collagen, starch, or gum arabic, synthetic polymers, such as discussed below, alcohols, polyols, and the like. The carrier can be a water miscible carrier composition that is substantially miscible in water. Such water miscible topical pharmaceutically acceptable carrier composition can include those made with one or more appropriate ingredients set forth above but can also include sustained or delayed release carriers, including water containing, water dispersible or water soluble compositions, such as liposomes, microsponges, microspheres or microcapsules, aqueous base ointments, water-in-oil or oil-in-water emulsions, gels or the like.

In one embodiment of the invention, the topical pharmaceutically acceptable carrier comprises a sustained release or delayed release carrier. The carrier is any material capable of sustained or delayed release of the TRRE to provide a more efficient administration resulting in one or more of less frequent and/or decreased dosage of the TRRE, ease of handling, and extended or delayed effects on dermatologic conditions. The carrier is capable of releasing TRRE when exposed to any oily, fatty, waxy, or moist environment on the area being treated or by diffusing or by release dependent on the degree of loading of TRRE to the carrier in order to obtain release of TRRE. Non-limiting examples of such carriers include liposomes, microsponges, microspheres, or microcapsules of natural and synthetic polymers and the like. Examples of suitable carriers for sustained or delayed release in a moist environment include gelatin, gum arabic, xanthane polymers; by degree of loading include lignin polymers and the like; by oily, fatty or waxy environment include thermoplastic or flexible thermoset resin or elastomer including thermoplastic resins such as polyvinyl halides, polyvinyl esters, polyvinylidene halides and halogenated polyolefins, elastomers such as brasiliensis, polydienes, and halogenated natural and synthetic rubbers, and flexible thermoset resins such as polyurethanes, epoxy resins and the like. Preferably, the sustained or delayed release carrier is a liposome, microsponge, microsphere or gel.

The compositions used in the method of treating dermatologic conditions of the invention are applied directly to the areas to be treated. While not required, it is desirable that the topical composition maintain TRRE at the desired location for about 24 to 48 hours.

If desired, one or more additional ingredients conventionally found in topical pharmaceutical or cosmetic compositions can be included with the carrier, such as a moisturizer, humectants, odor modifier, buffer, pigment, preservative, Vitamins such as A, C and E, emulsifier, dispersing agent, wetting agent, odor-modifying agent, gelling agents, stabilizer, propellant, antimicrobial agents, sunscreen, enzymes and the like. Those of skill in the art of topical pharmaceutical formulations can readily select the appropriate specific additional ingredients and amounts thereof. Suitable non-limiting examples of additional ingredients include superoxide dismutase, stearyl alcohol, isopropyl myristate, sorbitan monooleate, polyoxyethylene stearate, propylene glycol, water, alkali or alkaline earth lauryl sulfate, methylparaben, octyl dimethyl-p-amino benzoic acid (Padimate O), uric acid, reticulin, polymucosaccharides, hyaluronic acids, aloe vera, lecithin, polyoxyethylene sorbitan monooleate, Vitamin A or C, tocopherol (Vitamin E), alpha-hydroxy of alpha-keto acids such as pyruvic, lactic or glycolic acids, or any of the topical ingredients disclosed in U.S. Pat. Nos. 4,340,586, 4,695, 590, 4,959,353 or U.S. Pat. Nos. 5,130,298 and 5,140,043.

Because dermatologic conditions to be treated can be visible, the topical carrier can also be a topical cosmetically acceptable carrier. By "topical cosmetically acceptable carrier" as used herein is meant any substantially non-toxic carrier conventionally useable for topical administration of cosmetics in which TRRE will remain stable and bioavailable when applied directly to the skin surface. Suitable cosmetically acceptable carriers are known to those of skill in the art and include, but are not limited to, cosmetically acceptable liquids, creams, oils, lotions, ointments, gels, or solids, such as conventional cosmetic night creams, foundation creams, suntan lotions, sunscreens, hand lotions, make-up and make-up bases, masks and the like. Thus, to a substantial extent, topical cosmetically acceptable carriers and pharmaceutically acceptable carriers are similar, if not often identical, in nature so that most of the earlier discussion on pharmaceutically acceptable carriers also applies to cosmetically acceptable carriers. The compositions can contain other ingredients conventional in cosmetics including perfumes, estrogen, Vitamins A, C or E, alpha-hydroxy or alpha-keto acids such as pyruvic, lactic or glycolic acids, lanolin, Vaseline™ petroleum jelly, aloe vera, methyl or propyl paraben, pigments and the like.

The effective amount of TRRE in the compositions used to treat dermatologic conditions or diseases can vary depending on such factors as condition of the skin, age of the skin, the degree of purity of TRRE employed, the type of formulation and carrier ingredients used, frequency of administration, overall health of the individual being treated and the like. The precise amount for any particular patient used can be determined by those of skill in the pharmaceutical art taking into consideration these factors and the present disclosure. Preferably the composition is administered in at least two doses and no more than about six doses per day, or less when a sustained or delayed release form is used.

The compositions for topical, oral and parenteral administration usually contain from about 0.001% to about 10% by weight of TRRE compared to the total weight of the composition, preferably from about 0.01% to about 2% by weight of TRRE to composition, and especially from about 0.1% to about 1.5% by weight of TRRE to the composition.

The topical composition is administered by applying a coating or layer to the skin or mucosal area desired to be treated. As a practical matter of convenience, the applied material is rubbed into the area. Applications need not be rubbed into the skin and the layer or coating can be left on the skin overnight.

The amount of TRRE administered is sufficient to effectively reduce levels of TNF. Typically, reduced levels of TNF result in an amelioration of symptoms. Ameliorate denotes a lessening of the detrimental effect of the cancer on the individual. Administrations are typically conducted on a weekly or biweekly basis until a desired, measurable parameter is detected, such as diminution of disease symptoms. Administration can then be continued on a less frequent basis, such as biweekly or monthly, as appropriate. The effective amount is readily determined by one of skill in the art. The dosage ranges are those large enough to produce the desired effect in which the symptoms of the disease are ameliorated without causing undue side effects such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any complication.

The invention further encompasses methods of treating a disease associated with elevated levels of soluble TNF-R by administering an amount of an inhibitor of TRRE effective to decrease the levels of soluble TNF-R. Preferably, the disease treated is cancer. More preferably, the cancer includes, but is not limited to, astrocytoma, oligodendroglioma, ependymoma, medulloblastoma, primitive neural ectodermal tumor, pancreatic ductal adenocarcinoma, small and large cell lung adenocarcinomas, squamous cell carcinoma, bronchoalveolarcarcinoma, epithelial adenocarcinoma and liver metastases thereof, hepatoma, cholangiocarcinoma, ductal and lobular adenocarcinoma, squamous and adenocarcinomas of the uterine cervix, uterine and ovarian epithelial carcinomas, prostatic adenocarcinomas, transitional squamous cell bladder carcinoma, B and T cell lymphomas (nodular and diffuse), plasmacytoma, acute and chronic leukemias, malignant melanoma, soft tissue sarcomas and leiomyosarcomas.

The TRRE inhibitor can be any known in the art, including, but not limited to, metalloprotease inhibitors, antibodies that block the effective interaction between TNF-R and TRRE, antisense oligonucleotides specific for the gene encoding TRRE and ribozymes specific for the gene encoding TRRE. Methods of making antibodies are known in the art. Antibodies that block effective binding of TRRE to the TNF-R are easily screened for by using the assay method described herein.

The dosage ranges for the administration of TRRE inhibitors are those large enough to produce the desired effect in which the symptoms of the malignant disease are ameliorated without causing undue side effects such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any complication. For instance, when the inhibitor is an antibody, dosage can vary from about 0.1 mg/kg to about 2000 mg/kg, preferably about 0.1 mg/kg to about 500 mg/kg, in one or more dose administrations daily, for one or several days. Generally, when the antibodies are administered conjugated with therapeutic agents, lower dosages, can be used.

Therapeutic compositions of TRRE inhibitors can be administered by injection or by gradual perfusion over time. The inhibitors can be administered intravenously, intraperitoneally, intramuscularly, subcutaneously, intracavity, intrathecally or transdermally, alone or in combination with effector cells.

Preferably, in the case of cancer treatment, administration is intralesionally, for instance by direct injection directly into the tumor. Intralesional administration of various forms of immunotherapy to cancer patients does not cause the toxicity seen with systemic administration of immunologic agents. Fletcher et al. (1987) *Lymphokine Res.* 6:45; Rabinowich et al. (1987) *Cancer Res.* 47:173; Rosenberg et al. (1989) *Science* 233:1318; and Pizz et al (1984) *Int. J. Cancer* 34:359. Preferably, the intralesional administration is in conjunction with the cancer therapy technology described in, for example, U.S. Pat. Nos. 5,376,682, 5,192,537, and 5,643,740.

When the site of delivery is the brain, the therapeutic agent must be capable of being delivered to the brain. The blood-brain barrier limits the uptake of many therapeutic agents into the brain and spinal cord from the general circulation. Molecules which cross the blood-brain barrier use two main mechanisms: free diffusion; and facilitated transport. Because of the presence of the blood-brain barrier, attaining beneficial concentrations of a given therapeutic agent in the CNS may require the use of drug delivery strategies. Delivery of therapeutic agents to the CNS can be achieved by several methods.

One method relies on neurosurgical techniques. In the case of gravely ill patients, surgical intervention is warranted despite its attendant risks. For instance, therapeutic agents can be delivered by direct physical introduction into the CNS, such as intraventricular, intralesional, or intrathecal injection. Intraventricular injection can be facilitated by an intraventricular catheter, for example, attached to a reservoir, such as an Ommaya reservoir. Methods of introduction can also be provided by rechargeable or biodegradable devices. Another approach is the disruption of the blood-brain barrier by substances which increase the permeability of the blood-brain barrier. Examples include intraarterial infusion of poorly diffusible agents such as mannitol, pharmaceuticals which increase cerebrovascular permeability such as etoposide, or vasoactive agents such as leukotrienes. Neuwelt and Rappoport (1984) *Fed. Proc.* 43:214–219; Baba et al. (1991) *J. Cereb. Blood Flow Metab.* 11:638–643; and Gennuso et al. (1993) *Cancer Invest.* 11:638–643.

Further, it may be desirable to administer the compositions locally to the area in need of treatment; this can be achieved by, for example, local infusion during surgery, by injection, by means of a catheter, or by means of an implant, said implant being of a porous, non-porous, or gelatinous material, including membranes, such as silastic membranes, or fibers. A suitable such membrane is Gliadel® provided by Guilford sciences.

Another method involves pharmacological techniques such as modification or selection of the inhibitor to provide an analog which will cross the blood-brain barrier. Examples include increasing the hydrophobicity of the molecule, decreasing net charge or molecular weight of the molecule, or modifying the molecule, such as to resemble one normally transported across the blood-brain barrier. Levin (1980) *J. Med. Chem.* 23:682–684; Pardridge (1991) in: *Peptide Drug Delivery to the Brain*; and Kostis et al. (1994) *J. Clin. Pharmacol.* 34:989–996.

Encapsulation of an inhibitor in a hydrophobic environment such as liposomes is also effective in delivering drugs to the CNS. For example, WO 91/04014 describes a liposomal delivery system in which the drug is encapsulated within liposomes to which molecules have been added that are normally transported across the blood-brain barrier.

Another method of formulating the inhibitors to pass through the blood-brain barrier is encapsulation in cyclodextrin. Any suitable cyclodextrin which passes through the blood-brain barrier can be employed, including, but not limited to, β-cyclodextrin, γ-cyclodextrin and derivatives thereof. See generally, U.S. Pat. Nos. 5,017,566, 5,002,935 and 4,983,586. Such compositions can also include a glycerol derivative as described by U.S. Pat. No. 5,153,179.

Yet another method takes advantage of physiological techniques such as conjugation of the inhibitor to a transportable agent to yield a new chimeric transportable αC. For example, vasoactive intestinal peptide analog (VIPa) exerted its vasoactive effects only after conjugation to a Mab to the specific carrier molecule transferrin receptor, which facilitated the uptake of the VIPa-Mab conjugate through the blood-brain barrier. Pardridge (1991); and Bickel et al. (1993) *Proc. Natl. Acad. Sci. USA* 90:2618–2622. Several other specific transport systems have been identified, these include, but are not limited to, those for transferring insulin, or insulin-like growth factors I and II. Other suitable, non-specific carriers include, but are not limited to, pyridinium, fatty acids, inositol, cholesterol, and glucose derivatives. Certain prodrugs have been described whereby, upon entering the central nervous system, the drug is cleaved from the carrier to release the active drug. U.S. Pat. No. 5,017,566.

The TRRE inhibitor can be administered in conjunction with at least one cytokine effective to enhance an immune response against the cancer. Suitable cytokines include, but are not limited to, TNF, interleukin 2 (IL-2), interleukin 4 (IL-4), granulocyte macrophage colony stimulating factor (GM-CSF), and granulocyte colony stimulating factor (GCSF).

The TRRE inhibitor can be further administered in conjunction with at least one chemotherapeutic agent. Suitable chemotherapeutic agents include, but are not limited to, radioisotopes, vinca alkaloids, adriamycin, bleomycin sulfate, Carboplatin, cisplatin, cyclophosphamide, Cytarabine, Dacarbazine, Dactinomycin, Duanorubicin hydrochloride, Doxorubicin hydrochloride, Etoposide, fluorouracil, lomustine, mechlororethamine hydrochloride, melphalan, mercaptopurine, methotrexate, mitomycin, mitotane, pentostatin, pipobroman, procarbaze hydrochloride, streptozotocin, taxol, thioguanine, and uracil mustard.

Suitable subjects include those who are suspected of being at risk of a pathological effect of any neoplasia, particularly carcinoma, are suitable for treatment with the pharmaceutical compositions of this invention. Those with a history of cancer are especially suitable. Suitable human subjects for therapy comprise two groups, which may be distinguished by clinical criteria. Patients with "advanced disease" or "high tumor burden" are those who bear a clinically measurable tumor. A clinically measurable tumor is one that can be detected on the basis of tumor mass (e.g., by palpation, CAT scan, or X-ray; positive biochemical or histopathological markers on their own are insufficient to identify this population). A pharmaceutical composition embodied in this invention is administered to these patients to elicit an anti-tumor response, with the objective of palliating their condition. Ideally, reduction in tumor mass occurs as a result, but any clinical improvement constitutes a benefit. Clinical improvement includes decreased risk or rate of progression or reduction in pathological consequences of the tumor.

A second group of suitable subjects is known in the art as the "adjuvant group". These are individuals who have had a history of cancer, but have been responsive to another mode of therapy. The prior therapy may have included (but is not restricted to) surgical resection, radiotherapy, and traditional chemotherapy. As a result, these individuals have no clinically measurable tumor. However, they are suspected of being at risk for progression of the disease, either near the original tumor site, or by metastases.

This group may be further subdivided into high-risk and low-risk individuals. The subdivision is made on the basis of features observed before or after the initial treatment. These features are known in the clinical arts, and are suitably defined for each different cancer. Features typical of high risk subgroups are those in which the tumor has invaded neighboring tissues, or who show involvement of lymph nodes.

Another suitable group of subjects is those with a genetic predisposition to cancer but who have not yet evidenced clinical signs of cancer. For instance, women testing positive for a genetic mutation associated with breast cancer, but still of childbearing age, may wish to receive TRRE inhibitor treatment prophylactically to prevent the occurrence of cancer until it is suitable to perform preventive surgery.

A pharmaceutical TRRE inhibitor composition embodied in this invention is administered to patients in the adjuvant group, or in either of these subgroups, in order to elicit an anti-cancer response. Ideally, the composition delays recurrence of the cancer, or even better, reduces the risk of recurrence (i.e., improves the cure rate). Such parameters may be determined in comparison with other patient populations and other modes of therapy.

Of course, crossovers between these two patient groups occur, and the pharmaceutical compositions of this invention can be administered at any time that is appropriate. For example, therapy can be conducted before or during traditional therapy of a patient with high tumor burden, and continued after the tumor becomes clinically undetectable. Therapy can be continued in a patient who initially fell in the adjuvant group, but is showing signs of recurrence. The attending physician can determine how or when the compositions of this invention are to be used.

The invention also encompasses methods of diagnosing a disease associated with elevated levels of TRRE by obtaining a biological sample from a patient; measuring activity of TRRE in the sample and comparing the activity to the activity of a control biological sample. In the case of cancer diagnosis, the increased level of TRRE activity compared to the control can indicate that cancer is present. In the case of monitoring progression or recurrence of the disease, measurement of TRRE can indicate the status of the disease and can be an early marker for recurrence.

As provided herein, treatment, diagnosis and monitoring of cancers includes any cancers known in the art. These include, but are not limited to, glioblastoma, melanoma, neuroblastoma, adenocarcinoma, soft tissue sarcoma, leukemias, lymphomas and carcinoma. The invention is particularly useful for treatment, diagnosis and monitoring of carcinomas. Carcinomas include, but are not limited to, astrocytoma, oligodendroglioma, ependymoma, medulloblastoma, primitive neural ectodermal tumor, pancreatic ductal adenocarcinoma, small and large cell lung adenocarcinomas, squamous cell carcinoma, bronchoalveolarcarcinoma, epithelial adenocarcinoma and liver metastases thereof, hepatoma, cholangiocarcinoma, ductal and lobular adenocarcinoma, squamous and adenocarcinomas of the uterine cervix, uterine and ovarian epithelial carcinomas, prostatic adenocarcinomas, transitional squamous cell bladder carcinoma, B and T cell lymphomas (nodular and diffuse), plasmacytoma, acute and chronic leukemias, malignant melanoma, soft tissue sarcomas and leiomyosarcomas.

Embodied in this invention are compositions comprising polynucleotides with a therapeutically relevant genetic sequence as an active ingredient. The polynucleotide can be administered, for example, to augment or attenuate the natural level of expression of TRRE within a target cell.

In a another approach to attenuate TRRE activity, a polynucleotide encodes an antibody (or a fragment thereof) capable to binding to TRRE (or a fragment thereof). The polynucleotide would be introduced into the cell, and then expressed to produce the antibody or antibody fragment, which would then act as described supra to bind to TRRE and modulate its activity.

A polynucleotide for enhancing or attenuating TRRE expression can be introduced into cells as part of any suitable delivery vehicle known in the art. The polynucleotide can be administered to cells or injected into a tissue site as naked DNA, preferably in a supercoiled configuration. It is generally preferred to administer the polynucleotide as part of a composition that enhances expression in the target cell. Components of the composition can include those that protect the polynucleotide until delivery to the cell, enhance binding to or localization near target cells, enhance uptake or endocytosis into cells, promote translocation of the polynucleotide across the membrane into the cytoplasm, or enhance transport of the polynucleotide inside the cell to the site of action.

In one example, the composition comprises one half of a ligand-receptor binding pair, the other of which is present on the surface of the target cell. This can promote localization near the cell surface, endocytosis into the cell, or homing to the cell in vivo, or any combination thereof. Suitable components for including in the composition include, but are not limited to, antibodies or antibody fragments specific for the target tissue (for example, a tumor-associated antigen), integrins and integrin ligands optionally specific for the target tissue, and ligands for cytokine receptors on the target tissue. Where the object is to decrease TNF-R levels on the target cell by enhancing TRRE expression, a particularly preferred ligand is TNF itself. In this way, the composition will be focused towards cells with the phenotype to be treated, in preference to other cell types and cells already treated effectively.

In another example, the composition comprises a delivery vehicle that protects the polynucleotide and enhances its delivery into the cell. One type of suitable vehicle is a liposome that either encapsulates the polynucleotide, or (in the case of cationic liposomes) binds it by charge association. Another type of suitable vehicle is the capsid or envelope of a virus, defective viral particle, or synthetic viral particle, encapsidating or enveloping the polynucleotide. Preferred amongst such virally related particles are those that are tropic for the target tissue type, and comprise polypeptides (such as the influenza hemagglutinin) that promote fusion and delivery of the polynucleotide. The composition can also optionally comprise genetic elements of a virus that promotes replication of the therapeutic polynucleotide and/or integration into the genome of the target cell. Suitable viral systems for use with this invention include adenovirus vectors, retroviral vectors, adeno-associated viral vectors, sindbis virus vectors, and the like. Preferred are vectors that comprise viral genetic elements required in cis for packaging, the genetic elements required for replication or integration of the therapeutic polynucleotide, but not other viral genetic elements. Such vectors can be produced by packaging systems in which viral elements required only in trans are supplied by a host cell or second virus. See, e.g., Flotte et al. WO 95/13365.

It is often preferable to combine several such components and strategies into the composition with the therapeutic polynucleotide. For example, a polynucleotide can be enveloped in an adenovirus vector that expresses a targeting molecule like TNF as part of the viral package. The vector might alternatively express a coupling molecule, such as an avidin binding site, that can then be coupled with biotin-TNF for purposes of targeting to the target cell.

The following examples are meant to illustrate, but not limit, the claimed invention.

EXAMPLE 1

Materials and Methods

Cell Lines & Reagents

COS-1, a monkey kidney fibroblast-like cell line, was obtained from American Type Culture Collection (ATCC) (Rockville, Md.) were maintained as an adherent monolayer in RPMI-1640 medium (GIBCO Laboratories, Grand Island, N.Y.) supplemented with heat inactivated 10% fetal calf serum (FCS) (Irvine Scientific, Santa Ana, Calif.) and passed twice weekly. The cells were maintained at 37° C. in a humidified atmosphere of 5% $CO_2$. The transfected COS-1 cell line termed C75R was maintained in the same medium with the addition of 600 µg/ml Geneticin (G418-sulfate) (GIBCO BRL Life Technologies, Gaithersburg, Md.) and passed twice weekly. THP-1, a human monocytic leukemia cell line, was obtained from ATCC and maintained as a suspension culture in RPMI-1640 supplemented with 10% heat-inactivated FCS. PMA was purchased from Sigma Chemical Co. (St. Louis, Mo.). Recombinant forms of human soluble p55 and p75 TNF-R and TNF were kindly provided by Synergen Inc. (Boulder, Colo.).

ELISA assays were performed by the following methods. Polyclonal antibodies to human p75 TNF-R were generated by immunization of New Zealand white female rabbits according to the techniques described by Yamamoto et al. (1978) *Cell. Immunol.* 38:403–416. The IgG fraction of the immunized rabbit serum was purified using a protein G (Pharmacia Fine Chemicals, Uppsala, Sweden) affinity column by the method of Ey et al. (1978) *Immunochemistry* 15:429–436. The IgG fraction was then labeled with horseradish peroxidase (Sigma Chemical Co., St. Louis, Mo.) as described by Tijssen and Kurstok (1984) *Anal. Biochem.* 136:451–457.

The ELISA for p75 TNF-R was performed as follows: first, 5 µg of unlabeled IgG in 100 µl of 0.05 M carbonate buffer (pH 9.6) was bound to a 96-well ELISA microplate (Corning, Corning, N.Y.) by overnight incubation at 4° C. Individual wells were washed three times with 300 µl of 0.2% Tween-20 in phosphate buffered saline (PBS). The 100 µl of samples and recombinant receptor standards were then added to each well and incubated at 37° C. for 1 to 2 hours. The wells were then washed in the same manner, 100 µl of horseradish peroxidase-labeled IgG added and incubated for 1 hour at 37° C. The wells were washed once more and the color was developed for 20 minutes (min) at room temperature with the substrate of 2,2'-azinobis-3-ethylbenzothiazoline-6-sulfonic acid diammonium salt (ABTS) (Pierce, Rockford, Ill.) and 30% $H_2O_2$ (Fisher Scientific, Fair Lawn, N.J.) prepared according to manufacturer's instructions. The results were obtained by measuring the absorbance at 405 nm using an EAR 400AT plate reader (SLT-Lab Instruments, Salzburg, Austria). The concentration of sTNF-R in each sample was calculated from the regression line computed by known standards. Most of the R2 values of the linear regression were greater than 0.99. Duplicate wells of each dilution or sample were tested and the average of the results was reported.

In order to induce secretion of TRRE from THP-1 cells, the following experiment was performed. THP-1 cells growing in logarithmic phase were collected and resuspended to $1 \times 10^6$ cells/ml of RPMI-1640 supplemented with 1% FCS and incubated with $10^{-6}$ M PMA for 30 min in 5% $CO_2$ at 37° C. The cells were collected and washed once with serum-free medium to remove PMA and resuspended in the same volume of RPMI-1640 with 1% FCS. After 2 hours incubation in 5% $CO_2$ at 37° C., the cell suspension was collected, centrifuged, and the cell-free supernatant was collected as the TRRE-containing sample.

The level of TRRE activity in the THP-1 supernatant collected was detected and quantitated as described and was measured with a novel assay system described herein in detail below. Briefly, C75R and COS-1 cells were seeded at $2.5 \times 10^5$ cells/ml/well in a 24-well culture plate and incubated in 5% $CO_2$ at 37° C. for 12 to 16 hours. The medium in the wells was aspirated and 300 μl of TRRE experimental sample was incubated with C75R and COS-1 cells for 30 min in 5% $CO_2$ at 37° C. Simultaneously, C75R was incubated with 300 μl of fresh medium or buffer. At the end of the incubation period, the samples from each well were collected and the levels of soluble p75 TNF-R were measured by ELISA. The background level of sTNF-R, which was measured by incubation of the TRRE experimental sample with COS-1, and the spontaneous release of receptors by C75R, which was measured by incubation of medium or buffer alone with C75R cells, were subtracted from the level measured by the TRRE experimental sample incubated with C75R in order to calculate the net TRRE activity.

EXAMPLE 2

In vitro TRRE Assay System

The objective of this study was to establish an assay system that measures TRRE activity on the human TNF-R in its native conformation integrated into the cell surface membrane. The transfected COS-1 cell line was chosen for the assay system since no background of endogenous p75 TNF-R was observed. Attempts to study and characterize the enzyme responsible for sTNF-R release have been difficult because the presence of an active form of the proteolytic enzyme is indicated only indirectly by the generation of soluble receptors. Studies of release of other membrane bound proteins as well as TNF-R have been carried out by measuring the levels of soluble counterparts by ELISA or by FACS analysis for the presence or absence of the surface antigens. Therefore, the level of the enzyme itself has not yet been quantitated. We therefore devised a novel assay system to detect and quantitate TRRE. It was found that the level of soluble forms released into the medium depends on the level of expression of surface antigens on the membrane and the rate at which the cells can synthesize more and express these proteins on the membrane. In some studies, the enzyme levels and the kinetics of active enzyme formed have been correlated with the levels of soluble forms released and the kinetics of their release. We have now devised a more defined assay system to detect and also quantitate TRRE specifically and enzymes that cleave membrane receptor proteins in general.

Membrane-associated TNF-R was chosen as the substrate for TRRE instead of the recombinant TNF-R molecule, because the membrane-associated TNF-R simulates a more physiological microenvironment and substrate for the evaluation of TRRE activity. Membrane-associated TNF-R can also assist in alleviating nonspecific cleavage by other proteases which can occur in nonmembrane-associated forms. Since most human cells express only extremely low levels of both TNF-Rs, human p75 TNF-R-overexpressing cells were constructed by cDNA transfection into monkey COS-1 cells which do not express either TNF-Rs.

The cDNA of the human p75 TNF-R was cloned from a λgt10 cDNA library derived from human monocytic U-937 cells (Clonetech Laboratories, Palo Alto, Calif.). The cDNA was then subcloned into the EcoRI site of the mammalian expression vector pCDNA3 (Invitrogen, San Diego, Calif.) which contains the neomycin-resistance gene for the selection of transfected cells in the presence of G418. This construct was transfected into COS-1 cells using the calcium phosphate-DNA precipitation method described by Chen and Okayama. 24 hours post transfection, the transfected cells were placed in 600 μg/ml G418 (GIBCO BRL Life Technologies, Gaithersburg, Md.) for the selection of neomycin-resistant clones. The resistant cells were pooled and named C75R. These cells expressed approximately 70,000 receptors/cell by Scatchard analysis.

The first 300 bp on both 5' and 3' ends of the cloned fragment was sequenced and compared to the reported cDNA sequence of human p75 TNF-R. The cloned sequence was a 2.3 kb fragment covering positions 58–2380 of the reported p75 TNF-R sequence, which encompasses the full length of the p75 TNF-R-coding sequence from positions 90–1475. The 2.3 kb p75 TNF-R cDNA was then subcloned into the multiple cloning site of the pCDNA3 eukaryotic expression vector. The orientation of the p75 TNF-R cDNA was verified by restriction endonuclease mapping. The final 7.7 kb construct, pCDTR2, carried the neomycin-resistance gene for the selection of transfected cells in G418, and the expression of the p75 TNF-R was driven by the cytomegalovirus promoter (FIG. 1). The pCDTR2 was then transfected into monkey kidney COS-1 cells using the calcium phosphate-DNA precipitation method. The selected clone in G418 medium, termed C75R, was identified and subcultured.

$^{125}$I was purchased from ICN Pharmaceuticals, Inc. (Costa Mesa, Calif.) and the human recombinant TNF was radiolabeled using the Chloramine-T method. To determine the level of p75 TNF-R expression on C75R cells, $2 \times 10^5$ cells/well were plated into a 24-well culture plate and incubated for 12 to 16 hours in 5% $CO_2$ at 37° C. They were then incubated with 2–30 ng $^{125}$I radiolabeled human recombinant TNF in the presence or absence of 100-fold excess of unlabeled human TNF at 4° C. for 2 hours. After three washes with ice-cold PBS, cells were lysed with 0.1N NaOH and radioactivity was determined in a Pharmacia Clini-gamma counter (Uppsala, Sweden). To determine the effect of TRRE on the surface levels of p75 TNF-R, cells were incubated with or without the TRRE-containing supernatant for 30 min at 37° C., and then the medium was aspirated before incubation with radiolabeled TNF.

Soluble p75 TNF-R was generated from C75R cells by incubation with TRRE-containing supernatant. After a 30 min incubation, the supernatant was collected and centrifugally concentrated with Centriprep-10 filter (10,000 MW cut-off membrane) (Amicon, Beverly, Mass.) and applied to 10% acrylamide SDS-PAGE. The proteins were then electrophoretically transferred to a polyvinylidene difluoride membrane (Immobilon) (Millipore, Bedford, Mass.). Immunostaining was performed using the biotin-streptavidin system (Amersham, Amersham, UK) and the peroxidase substrate kit DAB (Vector Laboratories, Burlingame, Calif.).

Figure 2:
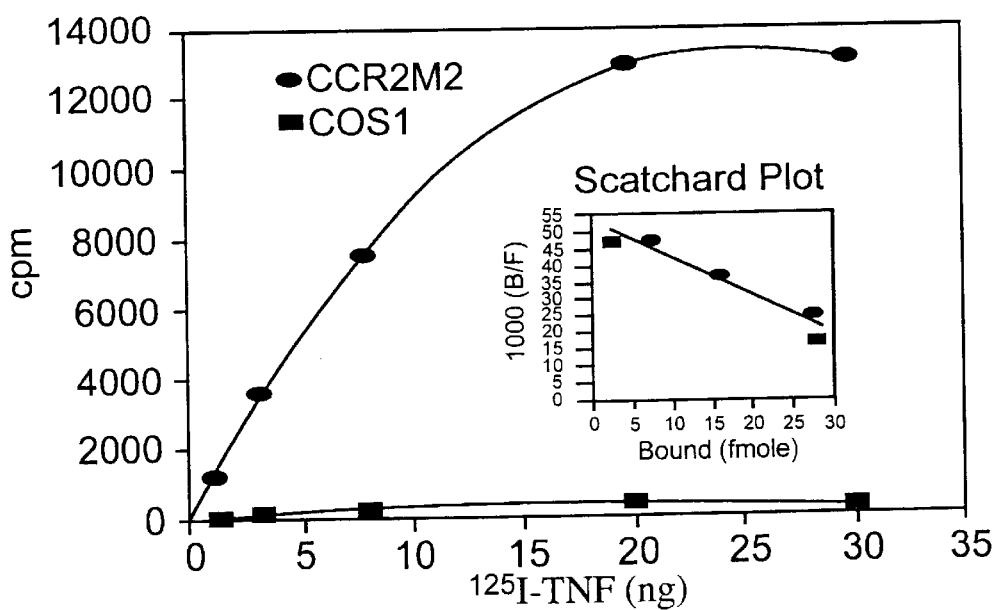
FIG. 2 is a graph depicting the results of measurement of p75 TNF-R on transfected COS-1 cells (C75R) by the method described herein. The results obtained with the C75R cells (●) is compared to that obtained with that from the parental COS-1 cells (■). The receptor number was calculated from a Scatchard plot (inset).

The results obtained are shown in FIG. 2, C75R had a very high level of specific binding of radiolabeled $^{125}$I-TNF, while parental COS-1 cells did not. The number of TNF-R expressed on C75R was determined to be 60,000–70,000 receptors/cell by Scatchard analysis (FIG. 2, inset). The level of TNF-R expression in this clone was 40 to 50 times higher than that of THP-1 cells. The Kd value calculated from the TNF binding assay of C75R was $5.6 \times 10^{-10}$ M. This Kd value was in close agreement to the values previously reported for native p75 TNF-R. Thus, transfected COS-1 cells expressed high levels of human p75 TNF-R in a form that appeared to be similar to native TNF-R.

In order to measure the effect of TRRE on membrane-bound TNF-R, the following experiment was performed.

C75R cells were seeded at a density of $2\times10^5$ cells/well in a 24-well cell culture plate and incubated for 12 to 16 hours at 37° C. in 5% $CO_2$. The medium in the wells was aspirated, replaced with fresh medium alone or with TRRE medium, and incubated for 30 min at 37° C. Throughout the examples, the "TRRE-medium" was that collected by stimulation of THP-1 cells with PMA followed by incubation of the cells in fresh medium for 2 hours as described. After this incubation, the medium was replaced with fresh medium containing 30 ng/ml $^{125}$I-labeled TNF. After 2 hours at 4° C., the cells were lysed with 0.1 N NaOH and the level of bound radioactivity was measured. The level of specific binding of C75R by $^{125}$I-TNF was significantly decreased after incubation with TRRE. The radioactive count was 1,393 cpm on the cells incubated with TRRE compared to 10,567 cpm on the cells not treated with TRRE, a loss of 87% of binding capacity.

In order to determine the size of the p75 TNF-R cleared from C75R by TRRE, the following experiment was performed. $15\times10^6$ C75R cells were seeded in a 150 mm cell culture plate and incubated at 37° C. in 5% $CO_2$ for 12 to 16 hours. TRRE medium was incubated with C75R cells in the 150 mm plate for 30 min and the resulting supernatant was collected and centrifuged. The concentrated sample was applied to 10% acrylamide SDS-PAGE and electrophoretically transferred to a polyvinylidene difluoride membrane (Immobilon). Immunostaining resulted in a single band of 40 kDa, similar to the size found in biological fluids (FIG. 4).

The following method and assay were used throughout the Examples to measure TRRE activity. C75R cells and COS-1 cells were seeded into 24-well culture plates at a density of $2.5\times10^5$ cells/ml/well and incubated overnight (for 12 to 16 hours) in 5% $CO_2$ at 37° C. After aspirating the medium in the well, 300 µl of TRRE medium was incubated in each well of both the C75R and COS-1 plates for 30 min in 5% $CO_2$ at 37° C. (corresponding to A and C mentioned below, respectively). Simultaneously, C75R cells in 24-well plates were also incubated with 300 µl of fresh medium or buffer (corresponding to B mentioned below). The supernatants were collected, centrifuged, and then assayed for the concentration of soluble p75 TNF-R by ELISA as described above.

The following values were assigned and calculations made. A=(amount of soluble p75 TNF-R in a C75R plate treated with the TRRE containing sample); i.e. the total amount of sTNF-R in a C75R plate. B=(amount of soluble p75 TNF-R spontaneously released in a C75R plate treated with only medium or buffer containing the same reagent as the corresponding samples but without exogenous TRRE); i.e. the spontaneous release of sTNF-R from C75R cells. C=(amount of soluble p75 TNF-R in a COS-1 plate treated with the TRRE sample or the background level of soluble p75 TNF-R released by THP-1.); i.e. the degraded value of transferred (pre-existing) sTNF-R in the TRRE sample during 30 min incubation in a COS-1 plate. This corresponds to the background level of sTNF-R degraded in a C75R plate.

The net release of soluble p75 TNF-R produced only by TRRE activity existing in the initial sample is calculated as follows: (Net release of soluble p75 TNF-R only by TRRE)= A-B-C. We assigned the net release value of soluble p75 TNF-R as the amount of TRRE activity and defined 1 pg of soluble p75 TNF-R net release (A-B-C) as one unit (U) of TRRE activity.

Figure 5:
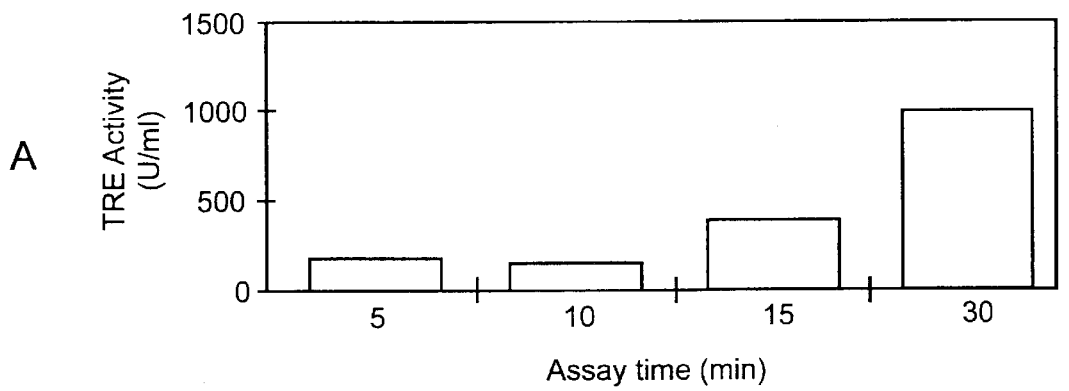
FIG. 5 is a series of graphs depicting the time course of TNF-R shedding induced by TRRE.
Figure 5:
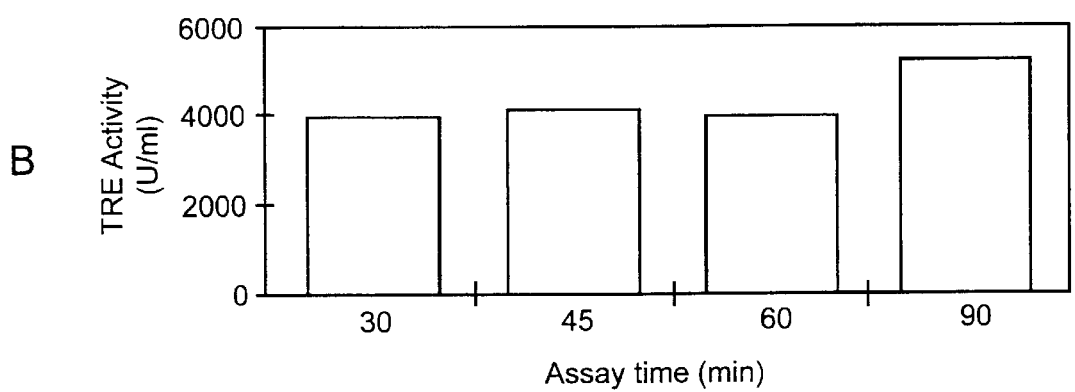

Once the TRRE assay was devised, the time course of receptor shedding was assayed by the following method. TRRE-medium was incubated with C75R and COS-1 cells for varying lengths of time between 5 and 90 min. The supernatants were then collected and assayed for the level of soluble p75 TNF-R by ELISA and the net TRRE activity was calculated as described above. Detectable levels of soluble receptor were released by TRRE within 5 min and increased up to 30 min (FIG. 5A). Subsequent experiments with longer incubation times showed that the level of TRRE remained relatively constant after 30 min, presumably from the depletion of substrates (FIG. 5B). Therefore, 30 min was determined to be the optimal incubation time for this assay system.

The binding assay clearly showed that the parental COS-1 cells did not bind human $^{125}$I-TNF, whereas the transfected C75R cells showed strong specific binding. Scatchard analysis indicated receptor levels of 70,000 per cell which were 40 to 50 times higher than that typically found on other cell lines. This higher level of substrate allowed detection of TRRE activity with much more sensitivity than with other cell lines. The Kd value calculated from Scatchard analysis was $5.6\times10^{-10}$ M, similar to the values previously reported for the native human p75 TNF-R. Thus, the transfected cells provided the membrane form of the receptor in its native configuration, resulting in an excellent source of substrate.

When C75R cells were incubated with TRRE medium, soluble p75 TNF-R was released into the supernatant which was measurable by ELISA. The amount of receptors released corresponded to level of TRRE activity. As C75R cells were incubated with TRRE medium, another well of C75R cells was simultaneously incubated with medium or buffer alone to measure the level of spontaneous release by C75R. The spontaneous release can be due to an endogenous source of proteolytic enzyme, a homolog of the human TRRE of monkey origin. In addition, TRRE medium was incubated with the parent COS-1 cells to detect the level of soluble receptors that was pre-existing in the sample. For this purpose, rather than directly measuring the level of soluble receptors in the supernatant by ELISA, we incubated the sample with COS-1 cells because we found that after incubation for 30 min with COS-1 cells, significant degradation of the soluble receptors was observed. The level of initial soluble receptors in the supernatant may decrease up to 50% after a 30 min incubation with COS-1 cells. Incorporating these two sources of background soluble receptors was the most accurate way to calculate the net TRRE activity.

The premise that increase in the level of soluble receptors in the supernatant was due to the proteolytic cleavage of membrane bound receptors was also supported by the loss of binding of $^{125}$I-labeled TNF to C75R cells after incubation with TRRE. Since the receptor generated by TRRE was similar in size to that found in biological fluids, this reinforced the finding that TRRE generates sTNF-R in vivo.

EXAMPLE 3

Mechanism of TRRE Production

In Example 2, a novel assay system was used to detect and quantitate the proteolytic activity of TRRE. Using this assay system, the mechanism of TRRE production was further investigated including (a) PMA requirement, (b) FCS dependence, (c) universality among other human cell lines and monocytes besides THP-1, (d) time course for secretion, (e) effect of PMA on TRRE secretion and synthesis, and (f) physiological inducers other than PMA.

THP-1 (a human monocytic leukemia cell line), U-937 (a human histiocytic lymphoma cell line), HL-60 (a human promyelocytic leukemia cell line), Raji (a human Burkitt lymphoma cell line) and K-562 (a human myelogenous leukemia cell line), which grow in suspension, and ME-180 (a human epidermoid carcinoma cell line) and MRC-5 (a human lung fibroblast cell line), which grow adherently, were purchased from American Type Culture Collection (Rockville, Md.). These cell lines were passed twice a week in RPMI-1640/10% heat-inactivated FCS.

Mononuclear cells were harvested at the interface of an isotonic Ficoll cushion (specific gravity, 1.05) from a Leukopac obtained from normal healthy volunteers according to the manufacturer's instructions (Sigma). Then monocytes were isolated by counterflow centrifugal elutriation with a Beckman JE-5.0 system. On average, the purity of the monocyte fraction was over 95%, as judged by morphologic examination and nonspecific esterase staining, and viability was over 98% as assessed by the trypan blue dye exclusion test.

THP-1 cells and human peripheral blood monocytes at a density of 1×106 cells/ml in RPMI-1640/1% FCS-contained were stimulated with 10-8, 10-7 and 10-6 M PMA for 30 min in 5% CO2 at 37° C. The stimulated cells were washed with serum-free medium and resuspended in the same volume of PMA-free medium with 1% FCS for 2 more hours in 5% $CO_2$ at 37° C. Then, the culture supernatants were collected and assayed for TRRE activity.

THP-1 cells and human monocytes were stimulated with $10^{-8}$, $10^{-7}$ and $10^{-6}$ M PMA and each supernatant was assayed for TRRE activity as described. $10^{-6}$ M PMA had a consistent, strong stimulation of THP-1 cells and human monocytes, inducing TRRE release at concentrations of 1,304 and 883 U/ml, respectively (Table 1). $10^{-7}$ M PMA stimulation induced relatively low amounts of TRRE and $10^{-8}$ M PMA stimulation did not induce any TRRE from either monocytes or THP-1 cells (data not shown). PMA stimulation at the concentration of $10^{-6}$ M was adopted in all subsequent experiments for the induction of TRRE from THP-1 cells.

TABLE 1

| Cell | Activator | | TRRE Activity (U) |
|---|---|---|---|
| Human Monocyte | PMA | $10^{-7}$ M | 51 |
| | | $10^{-6}$ M | 883 |
| THP-1 | PMA | $10^{-7}$ M | 368 |
| | | $10^{-6}$ M | 1,304 |

Suspension cell lines including THP-1, U-937, HL-60, Raji and K-562 at a density of $1 \times 10^6$ cells/ml were stimulated in RPMI-1640/1% FCS-with $10^{-6}$ M PMA for 30 min in 5% $CO_2$ at 37° C. After pelleting the cells and discarding the supernatants, the cells were washed once with serum-free medium and then incubated for 2 more hours at the same density of $1 \times 10^6$ cells/ml in PMA-free RPMI-1640/1% FCS. Adherent cell lines including ME-180 and MRC-5 were seeded in 100 mm cell culture plates with RPMI-1640/ 10% FCS-at a density of $6 \times 10^6$ cells/10 ml/plate in 5% $CO_2$ at 37° C. overnight. After discarding the medium from the 100 mm plates, these adherent cells were stimulated in 6 ml of RPMI-1640/1% FCS with $10^{-6}$ M PMA (at an approximate density of $1 \times 10^6$ cells/ml) for 30 min in 5% $CO_2$ at 37° C. Following washing of the plates with serum-free medium 3 times, the cells were incubated for 2 more hours in 6 ml of PMA-free RPMI-1640/1% FCS. These supernatants from suspension and adherent cells were collected and assayed for TRRE activity (as described in Example 1).

$10^{-6}$ M PMA-stimulated suspension cell lines including THP-1, U-937, HL-60, Raji, and K-562 and adherent cell lines including ME-180 and MRC-5 produced TRRE activity at concentrations of 2,884 U/ml, 3,288 U/ml, 3,144 U/ml, 2,390 U/ml, 3,356 U/ml, 1,694 U/ml, and 1,477 U/ml per $1 \times 10^6$ cells, respectively (Table 2). Thus, TRRE can be induced not only by THP-1 cells but also by all cell lines investigated with PMA-stimulation.

TABLE 2

| Cell line | TRRE (U/ml/$10^6$ cells) |
|---|---|
| THP-1 (human monocytic leukemia) | 2,884 |
| U-937 (human histiocytic lymphoma) | 3,288 |
| HL-60 (human promyelocytic leukemia) | 3,144 |
| ME-180 (human epidermoid carcinoma) | 1,694 |
| MRC-5 (human lung fibroblast) | 1,477 |
| Raji (Burkitt lymphoma) | 2,390 |
| K-562 (human myelogenous leukemia) | 3,356 |

THP-1 cells were stimulated with 10-6 M PMA in RPMI-1640 with 1% FCS for 30 min. The stimulated cells were then washed and incubated for 2 more hours in PMA-free RPMI 1640 with 0%, 1%, and 10% FCS, which led to the release of 224, 1,356, and 2,275 U/ml TRRE, respectively (Table 3). This suggests that some serum factors are required by cells for a normal response to PMA.

TABLE 3

| FCS Concentration | TRRE Activity (U/ml) |
|---|---|
| 0% | 224 |
| 1% | 1,356 |
| 10% | 2,275 |

Figure 6:
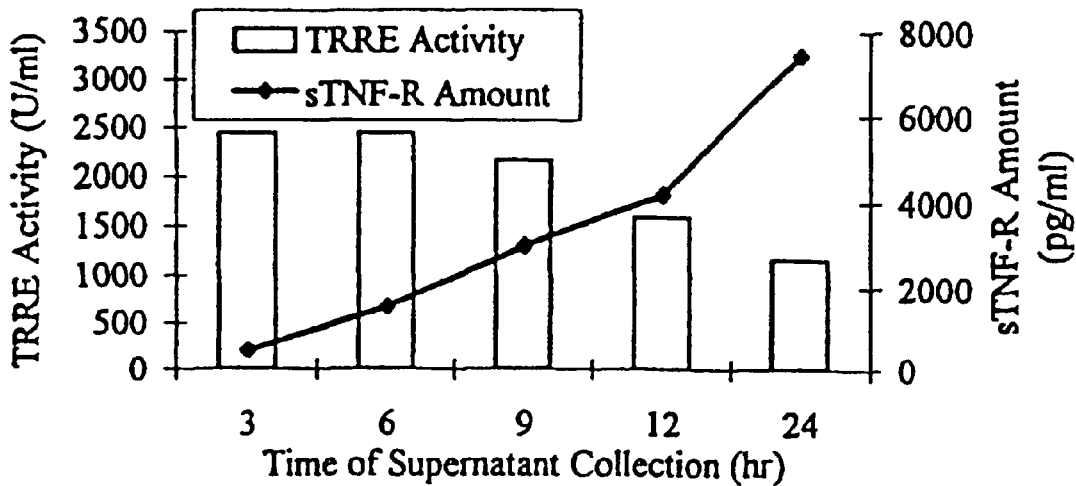
FIG. 6 is a graph depicting the time course of TRRE induction from PMA-stimulated cells. The kinetics of TRRE activity and sTNF-R were conducted on the incubation time from 3 to 24 hours including the initial 30 min. PMA-stimulation time.

THP-1 cells were stimulated with $10^{-6}$ M PMA in RPMI-1640 with 1% FCS for 30 min and then washed and resuspended in the same volume of PMA-free medium with 1% FCS. The cells were incubated for additional 2 to 23 hours making the total induction time of TRRE 3 to 24 hours from initial stimulation. This kinetic study revealed that the release of TRRE into culture supernatants peaked as early as 3 hours, followed by a gradual decline afterwards, while the level of sTNF-R derived from THP-1 cells increased over time (FIG. 6). Consequently, in order to obtain higher TRRE activity with lower sTNF-R background, 2 hours incubation (total 3 hours induction) was adopted in subsequent experiments.

Figure 7:
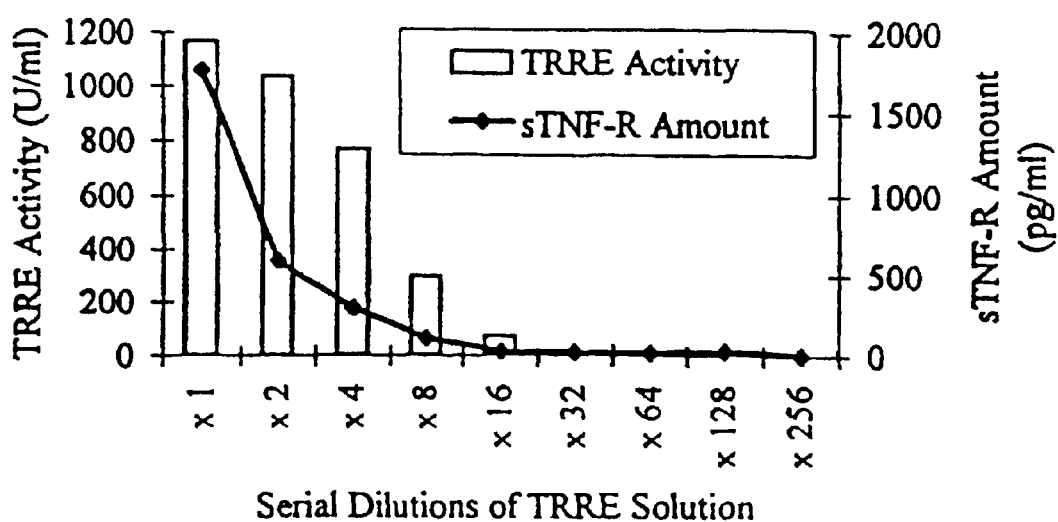
FIG. 7 is a graph depicting the effects of serial dilution of TRRE medium on production of sTNF-R.

TRRE media were serially diluted up to 1:256 dilution. Detectable levels of TRRE activity were present in samples diluted 16-fold (FIG. 7). While the level of sTNF-R present in TRRE supernatants decreased in proportion to their dilution, no significant differences in TRRE activity were found between the original and 2-fold diluted supernatant, suggesting a depletion of substrates and that the level of TRRE activity in the original supernatant might be saturating the assay system.

Several inhibitors including cycloheximide (Chx) (an inhibitor of protein synthesis), actinomycin D (ActD) (an inhibitor of RNA synthesis), N-ethylmaleimide (NEM) (an inhibitor of membrane internalization and movement), cytochalasin B (CytB) (an inhibitor of microfilament formation), and colchicine (Col) (an inhibitor of microtubule formation) were purchased from Sigma Chemical (St. Louis, Mo.). THP-1 cells at a density of $1 \times 10^6$ cells/ml in RPMI-1640/1% FCS with $10^{-6}$ M PMA was co-stimulated along with 10 μg/ml Chx, 1 μg/ml ActD, 1 mM NEM, 0.1 mM CytB, or 0.1 mM Col for 30 min at 37° C. in 5% $CO_2$.

Following centrifugation at 400×g for 5 min, the supernatant was discarded and the cells were washed once with serum-free medium. The cells were incubated for an additional 2 hours at the same density ($1\times10^6$ cells/ml) in PMA-free RPMI-1640 with corresponding inhibitors. These supernatants were collected and assayed for TRRE activity. The supernatant from THP-1 cells stimulated only with $10^{-6}$ M PMA, but without any inhibitor, was used as a control. % TRRE production was expressed by dividing TRRE activity induced with PMA plus inhibitors by that of the control.

To understand the mechanism of PMA in the production of TRRE, several inhibitors were co-incubated with PMA as described. 10 µg/ml Chx, 1 µg/ml ActD, 1 mM NEM, 0.1 mM CytB, and 0.1 mM Col modified PMA-induced TRRE activity to 104%, 97%, 17%, 91%, and 111%, respectively (Table 4). The results obtained indicate that only NEM inhibited PMA-induced TRRE production, suggesting that membrane internalization and movement are only involved in the release of TRRE induced by PMA. Protein synthesis, RNA synthesis and transmission within the cytoplasm may not be required for PMA-induced TRRE release.

TABLE 4

| Inhibitor | Concentration | % of TRRE production |
|---|---|---|
| Actinomycin D | 1 µg/ml | 104 |
| Cycloheximide | 10 µg/ml | 97 |
| N-ethyl-maleimide | 1 mM | 17 |
| Cytochalasin B | 0.1 mM | 91 |
|  | 0.01 mM | 103 |
| Colchicine | 1 mM | 125 |
|  | 0.1 mM | 111 |
|  | 0.01 mM | 95 |

THP-1 cells at a density of $1\times10^6$ cells/ml were stimulated in 1% FCS-contained RPMI-1640 with $10^{-6}$ M PMA for 30 min at 37° C. in 5% $CO_2$. After washing the cells with serum-free medium to remove PMA, the cells were incubated in the same volume of 1% FCS-contained RPMI-1640 without PMA for 2 hours at 37° C. in 5% $CO_2$. Then the cells were centrifuged down and the supernatant was collected for TRRE assay. These pelleted cells were again resuspended in 1% FCS-contained RPMI-1640 with or without $10^{-6}$ M PMA and incubated for 30 min at 37° C. in 5% $CO_2$. After washing the cells with serum-free medium to remove PMA, the cells, stimulated or non-stimulated by PMA, were incubated in the same volume of 1% FCS-contained RPMI-1640 without PMA for 2 and 4 hours each at 37° C. in 5% $CO_2$. Then, all 4 types of supernatants were collected for TRRE assay (as described in Example 1).

Figure 8:
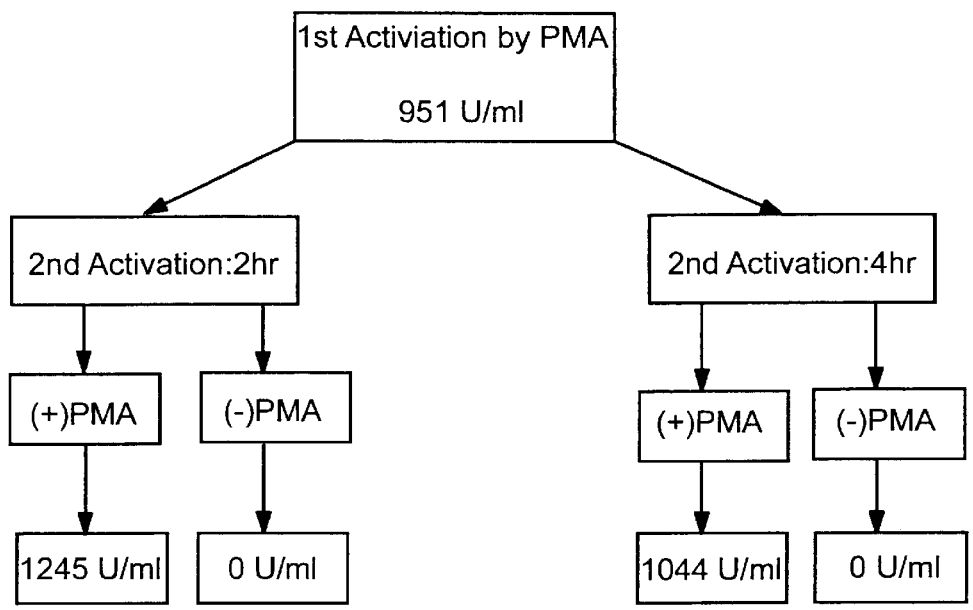
FIG. 8 is a schematic diagram depicting the effect of successive PMA stimulations of THP-1 cells on TRRE production.
Figure 9:
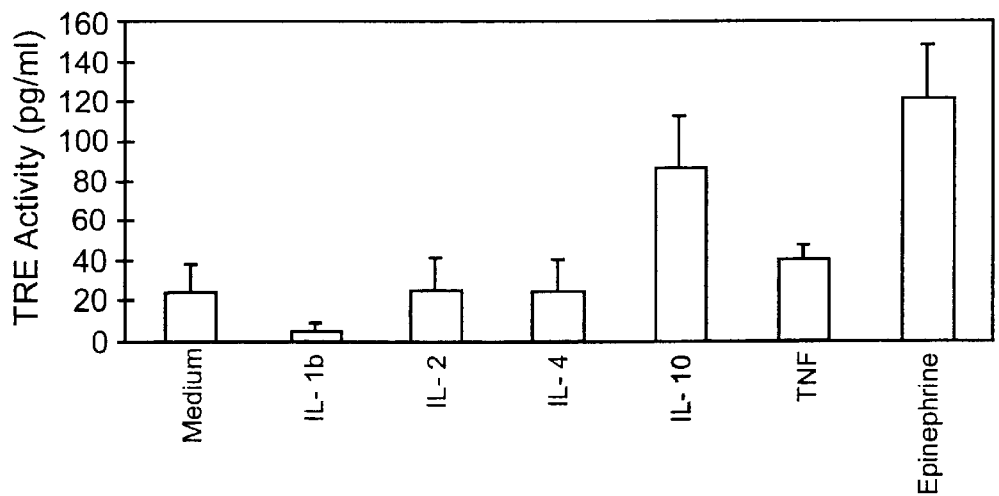
FIG. 9 depicts the induction of TRRE from THP-1 cells treated with various cytokines and hormones.

THP-1 cells were stimulated with PMA twice to investigate the successive induction of TRRE as described. By the first stimulation of PMA, THP-1 cells released 951 U/ml TRRE. Then, these cells, which were again stimulated by PMA for 30 min and incubated for additional 2 hours and 4 hours in PMA-free medium, released 1,245 U/ml and 1,044 U/ml TRRE, respectively (FIG. 8). On the other hand, after the first stimulation of PMA, the THP-1 cells, which were again incubated for 2 hours and 4 hours in PMA-free medium following 30 min incubation in PMA-free medium and washing, released no TRRE activity. These data revealed that TRRE could be released again by a second PMA-stimulation with nearly identical concentrations between 2 hours and 4 hours incubation; whereas new TRRE release was not detected without the second PMA-stimulation even though once stimulated with PMA. According to these data, the response of THP-1 cells to PMA for the release of TRRE may be very quick and repeatable, however the response does not last more than 2 hours once PMA is removed.

THP-1 cells at a density of $1\times10^6$ cells/ml were stimulated for 2 hours in 1% FCS-contained RPMI-1640 alone, or with cytokines including IL-1β (10 ng/ml), IL-2 (4 µg/ml), IL-4 (10 ng/ml), IL-6 (100 ng/ml), IL-10 (100 ng/ml), TNF (1 µg/ml), LT (1 µg/ml) and IFN-γ (100 ng/ml), and hormones including epinephrine ($10^{-6}$ M), insulin ($10^{-7}$ M), prostaglandin $E_2$ ($PGE_2$)($10^{-7}$ M) and hydrocortisone ($10^{-6}$ M). After pelleting the cells, culture supernatants were collected and assayed for TRRE activity. For the TRRE assay, the level of spontaneous release of soluble p75 TNF-R was obtained by incubating C75R cells in RPMI-1640/1% FCS which contained only the stimulants described above, and no exogenous TRRE.

We have shown that PMA is a very strong and rapid inducer of sTNF-R. Gatanaga et al (1991); and Hwang et al. (1993) J. Immunol. 151:5631–5638. However, in order to determine physiological inducers of TRRE other than PMA, several cytokines and hormones were investigated as described. Among cytokines including IL-1β, IL-2, IL-4, IL-6, IL-10, TNF, LT, and IFN-γ, and hormones including epinephrine, insulin, $PGE_2$, and hydrocortisone, epinephrine and IL-10 induced TRRE activity with 2 hours stimulation. The level of TRRE activity induced by IL-10 and epinephrine, was significantly lower than that caused by PMA.

Tables 1 and 2 showed that the TRRE induction protocol and its assay system were not only effective to all the tumor cell lines investigated, but also to normal human monocytes. Therefore, TRRE activity is probably not a unique characteristic of transformed cell lines, but a common trait possessed by most human cells. This is in agreement with the previous work that reported most human cells express both TNF-Rs simultaneously. Gehr et al. (1992); Naume et al. (1991) J. Immunol. 146:3045–3048; and Porteu et al. (1991) J. Biol. Chem. 266:18846–18853. Thus, cells can autoregulate their susceptibility to TNF by controlling the number of their own TNF-R by synthesizing TRRE. The reason that a PMA-concentration as high as $10^{-6}$ M was required to observe an effective induction of TRRE can be due to the protocol used. Here, THP-1 cells were pulse stimulated for 30 min, washed once to remove PMA and incubated in PMA-free medium for 2 more hours for the induction of TRRE. Also, it is quite possible that these cells release high levels of active TRRE immediately when stimulated with PMA during the 30 min pulse stimulation. The TRRE released during this period can be discarded when the cells are washed and incubated with fresh medium.

Although the production of TRRE was FCS-dependent, FCS-enriched medium alone in the absence of PMA-stimulation did not induce TRRE activity. Therefore, some serum factors may assist in the secretion of TRRE induced by PMA, while serum itself does not induce. Since the incubation of PMA-stimulated THP-1 cells in the presence of 1% FCS would significantly decrease the level of contaminating proteins from FCS and increase the specific activity of TRRE (the value of TRRE units/A280) in the supernatant, TRRE induction at 1% FCS concentration was adopted for subsequent experiments.

PMA is an extremely strong and rapid inducer of TRRE and, indirectly, TNF-R. After a 30 min stimulation of THP-1 cells with $10^{-6}$ M PMA the secretion of TRRE started immediately and reached its maximum as quickly as within 2 hours. This suggests that TRRE is already stored in THP-1 cells ready to be secreted in response to PMA-stimulation. Basically, PMA is a powerful stimulator of protein kinase C which is anchored inside the cell membrane once activated. Thus, it is likely that (i) TRRE is stored in the cytoplasm very close to the cell membrane ready to be secreted through the protein kinase C cascade by PMA stimulation; (ii) TRRE is a peripheral (or extrinsic) membrane protein which is dissociated from the membrane through the change of interactions with other proteins or with any phospholipid by stimulated protein kinase C; or (iii) TRRE is an integral (or intrinsic) membrane protein which is cleaved and secreted to be an active form after its cytoplasmic portion interacts directly or indirectly with protein kinase C.

TRRE induction by PMA did not require de novo protein synthesis, RNA synthesis and transmission inside the cytoplasm, but only membrane internalization and movement. This is compatible with the data that TRRE released very quickly by PMA-stimulation and halted once PMA was removed. With PMA-stimulation, however, TRRE synthesis began at the same time as TRRE release. After the initial release, TRRE accumulated inside the cell or on the cell surface within 2 hours ready to be secreted by the next stimulation. Evidence for direct cleavage of TNF-R is that the shedding of sTNF-R occurs very quickly (5 min) and with maximal shedding within 30 min.

Except for PMA, shedding of sTNF-R has been known to be enhanced by several cytokines including TNF, IL-1, IL-6, IL-10 and IFN, leukocyte migration enhancement factors including formyl-methionyl-leucyl-phenylalanine (fMLP) and C5a, and calcium ionophore. Gatanaga (1993) *Lymphokine Res.* 12:249–253; Porteu (1994) *J. Biol. Chem.* 269:2834–2840; van der Poll (1995) *J. Immunol.* 155:5397–5401; Porteu et al. (1991); and Porteu and Natah (1990) *J. Exp. Med.* 172:599–607. In the experiments provided herein, IL-10 and epinephrine induced TRRE from THP-1 cells with 2 hour stimulation, though their induction was not as strong as PMA.

IL-10 is a potent inhibitor of monocyte- and macrophage-functions. Moore (1993) *Annu. Rev. Immunol.* 11:165–190. IL-10 has anti-inflammatory activity on monocytes and inhibits the release of pro-inflammatory cytokines including TNF and IL-1. Bogdan et al. (1991) *J. Exp. Med.* 174:1549–1555; Fiorentino et al. (1991) *J. Immunol.* 147:3815–3822; de Waal Malefyt et al. (1991) *J. Exp. Med.* 174:1209–1220; Katsikis et al. (1994) *J. Exp. Med.* 179:1517–1527; Joyce et al. (1994) *Eur. J. Immunol.* 24:2699–2705; and Simon et al. (1994) *Proc. Natl. Acad. Sci. USA* 91:8562–8566. Elevated levels of IL-10 have been detected in plasma of patients with sepsis, and after administration of LPS to animals. Marchant et al. (1994) *Lancet* 343:707–708; Derkx et al. (1995) *J. Infect. Dis.* 171:229–232; Durez et al. (1993) *J. Exp. Med.* 177:551–555; and Marchant et al. (1994) *Eur. J. Immunol.* 24:1167–1171. In vivo, IL-10 has also been shown to protect mice against endotoxin shock. Gerard et al. (1993) *J. Exp. Med.* 177:547–550; and Howard et al. (1993) *J. Exp. Med.* 177:1205–1208. IL-10 leads to increased levels of mRNA for p75 TNF-R, increased release of soluble p75 TNF-R and a concomitant reduction of surface expression of p75 TNF-R on monocytes. Joyce et al. (1994). Thus, IL-10 may be considered to reduce the pro-inflammatory potential of TNF by (i) inhibiting the release of TNF itself, and (ii) down-regulating surface TNF-R expression while (iii) increasing production of sTNF-R capable of neutralizing TNF cytotoxicity. Joyce et al. (1994); and Leeuwenberg et al. (1994) *J. Immunol.* 152:4036–4043. The data presented herein that IL-10 may induce TRRE activity are consistent with these findings and indicate a newly revealed function of IL-10 as an anti-inflammatory cytokine.

In stressful situations including endotoxic shock, serum levels of catecholamines and glucocorticoids are elevated chiefly from adrenal medulla and adrenal cortex, respectively, in response to high serum level of adrenocorticotropic hormone (ACTH) throughout the whole body system. TNF also has been implicated in the early metabolic events following stressful situations, and infusion of recombinant TNF in dogs was associated with increase of serum levels of catecholamines, glucocorticoids and glucagon. Tracey et al. (1987) *Surg. Gynecol. Obstet.* 164:415–422. On the other hand, as a local phenomenon, epinephrine and norepinephrine are found in macrophages which express β-adrenergic receptors and these endogenous catecholamines seem to regulate LPS-induced TNF production in an autocrine fashion in vitro. Hjemdahl et al. (1990) *Br. J. Clin. Pharmacol.* 30:673–682; Hjemdahl et al. (1990) *Br. J. Clin. Pharmacol.* 30:673–682; Talmadge et al. (1993) *Int. J. Immunopharmacol.* 15:219–228; and Spengler et al. (1994) *J. Immunol.* 152:3024–3031. Actually, exogenous epinephrine and isoproterenol, a specific β-adrenergic agonist, inhibit the production of TNF from human blood and THP-1 cells stimulated by LPS. Hu et al. (1991) *J. Neuroimmunol.* 31:35–42; and Severn (1992) *J. Immunol.* 148:3441–3445.

While epinephrine may be an important endogenous inhibitor of TNF production, especially in sepsis, epinephrine also decreases the number of TNF-R on macrophages. Bermudez et al. (1990) *Lymphokine Res.* 9:137–145. We have shown that in trauma patients both p55 and p75 TNF-R levels were significantly elevated within 1 hour of injury along with high serum level of epinephrine. Tan et al. (1993) *J. Trauma* 34:634–638. These findings are in agreement with the data that epinephrine induced TRRE activity and may lead to the increase of sTNF-R.

Figure 20:
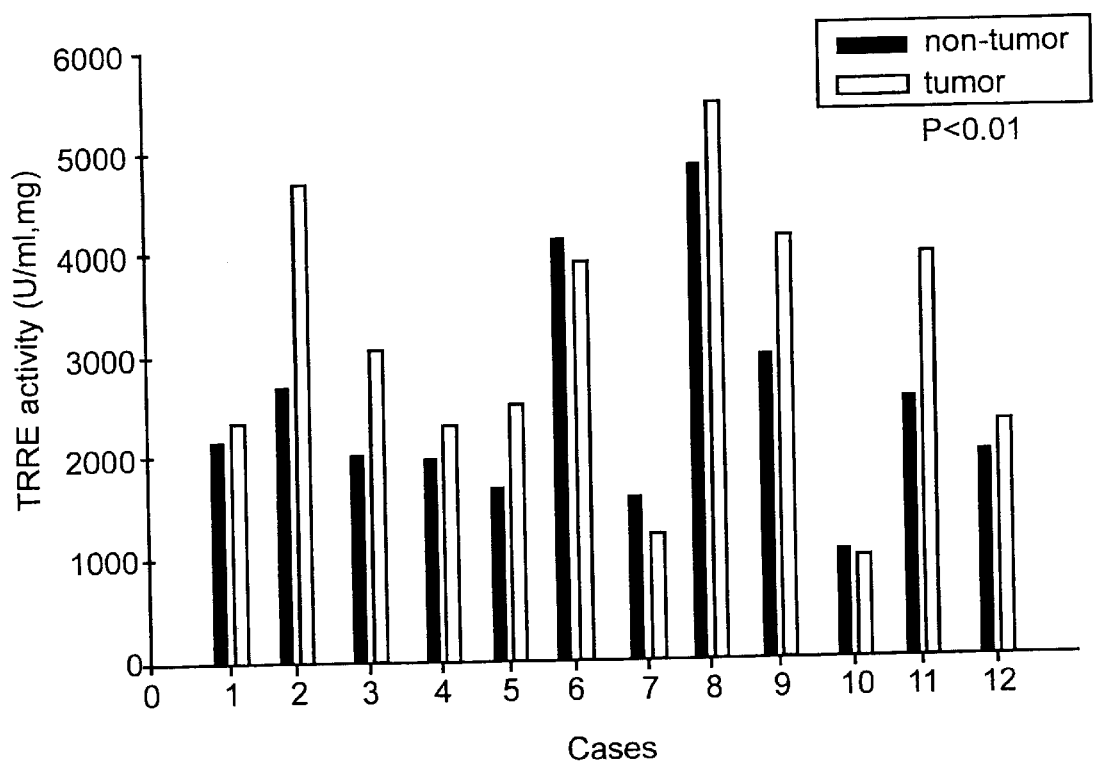
FIG. 20 is a bar graph demonstrating TRRE activity in human lung tumor tissue (solid bar) or adjacent non-tumor tissue (white bars).

Insulin and glucagon have the function to down-regulate TNF-R in addition to epinephrine. Bermudez et al. (1990). Many inflammatory cytokines besides IL-10 may influence the shedding of sTNF-R including TNF, IL-1, IL-6, and IFN for up-regulation and IL-4 for down-regulation. van der Poll et al. (1995); Gatanaga et al. (1993); and Joyce et al. (1994). According to the data presented herein, insulin, IL-1β and IL-6 induced sTNF-R from THP-1 cells with 2 hours stimulation but no apparent TRRE activity, suggesting that the sTNF-R may be produced by (a) protease(s) other than TRRE or by another form of TRRE which may be membrane-bound. Thus, there may be at least two pathways responsible for the shedding of sTNF-R, not only in vitro but also in vivo. In vivo, one is seen in trauma patients, who experience a rapid increase of sTNF-R in the serum. This pattern of increase is similar to that caused by PMA stimulation and therefore is presumably mediated by TRRE. Another pathway in vivo is involved in chronic or spontaneous induction of sTNF-R seen in cancer patients and even in healthy individuals. Gatanaga et al. (1990a); and Gatanaga et al. (1990b). Presumably (a) protease(s) other than TRRE or various forms of TRRE including a membrane-bound form activated by cleavage to a soluble form could be responsible for this increase of sTNF-R. However, the induction of sTNF-R in cancer patients may be at least partially due to increased TRRE activity. This activity was generally higher in human lung tumors than in non-cancerous surrounding tissues. As shown in FIG. 20, in 9 out of 12 cases, TRRE activity was higher in culture supernatants of tumor cells than in that of adjacent non-tumor cells. In cases 2, 3, 5, 9, and 11, the TRRE activity was approximately 75%, 50%, 30%, 36%, and 60% higher, respectively, in tumor than in non-tumor cells.

EXAMPLE 4

Physiologic Properties of TRRE

In this Example, the physiologic properties of TRRE were investigated, including (a) stability versus temperature and pH, (b) metal requirements, (c) mechanistic class of protease, (d) comparison with known proteases, especially MMPs, and (e) conformational relationship between sTNF-R and TRRE. The example further provides partial purification steps and results for TRRE.

In order to purify TRRE, TRRE medium was concentrated by 100% saturated ammonium sulfate precipitation method at 4° C. The precipitate was pelleted by centrifugation at 10,000×g for 30 min and resuspended in PBS in approximately twice the volume of the pellet. This solution was then dialyzed at 4° C. against 10 mM Tris-HCl, 60 mM NaCl, pH 7.0. This sample was loaded on an anion-exchange chromatography, Diethylaminoethyl (DEAE)-Sephadex A-25 column (Pharmacia Biotech) (2.5×10 cm) previously equilibrated with 50 mM Tris-HCl, 60 mM NaCl, pH 8.0. TRRE was then eluted with an ionic strength linear gradient of 60 to 250 mM NaCl, 50 mM Tris-HCl, pH 8.0. Each fraction was measured for absorbance at 280 nm and assayed for TRRE activity. The DEAE fraction with the highest specific activity (the highest value of TRRE units/A280) was pooled and used in the characterizations of TRRE described in this example. These samples are termed herein "partially-purified" TRRE.

The partially-purified TRRE was preincubated at 37° C. for 30 min with several classes of protease inhibitors. Protease inhibitors were purchased from Sigma Chemical (St. Louis, Mo.), including phenylmethylsulfonyl fluoride (PMSF), 4-(2-aminoethyl)-benzenesulfonyl fluoride (AEBSF), 3,4-dichloroisocoumarin (3,4-DCI), N-α-tosyl-L-lysine chloromethyl ketone (TLCK), N-tosyl-L-phenylalanine chloromethyl ketone (TPCK), ethylenediaminetetraacetic acid (EDTA), ethyleneglycol bis(2-aminoethyl ether)tetraacetic acid (EGTA), 1,10-phenanthroline, and phosphoramidon. These inhibitors can be divided into the following classes: (i) serine protease inhibitors (4 mM PMSF, 0.5 mM AEBSF, and 0.1 mM 3,4-DCI); (ii) serine and cysteine protease inhibitors (0.1 mM TLCK and TPCK); (iii) chelating agents (2 mM EDTA, EGTA, and 1,10-phenanthroline); (iv) a metallo-endoprotease inhibitor (0.5 mM phosphoramidon); and (v) divalent heavy metal ions (2 mM $CaCl_2$, $MgCl_2$, $MnCl_2$, $ZnCl_2$, $CoCl_2$, $CuCl_2$, and $FeCl_2$). After the preincubation, the samples were assayed for TRRE activity. For the TRRE assay, spontaneous release of soluble p75 TNF-R in each sample from C75R cells was obtained by incubating C75R cells with the corresponding reagents without TRRE. Partially-purified TRRE preincubated at 37° C. for 30 min without any reagent and assayed for TRRE activity was taken as a control. The percent activity remaining (% control) was expressed relative to the control.

The partially-purified TRRE was preincubated with 4 mM $CaCl_2$, 0.1 mM $ZnCl_2$, 2 mM 1,10-phenanthroline, 2 mM 1,10-phenanthroline plus 2 mM CaCl2, or 2 mM 1,10-phenanthroline plus 2 mM ZnCl2 at 37° C. for 30 min prior to assaying for TRRE activity. The percent activity remaining (% control) was calculated as above.

The results obtained are depicted in Table 6. Partial inhibition of TRRE activity was obtained by chelating agents such as 1,10-phenanthroline, EDTA and EGTA (% TRRE activities remaining were 41%, 67% and 73%, respectively, at 2 mM concentration), which are potent inhibitors of metalloproteases (Table 5). On the other hand, serine protease inhibitors such as PMSF, AEBSF and 3,4-DCI, and serine and cysteine protease inhibitors such as TLCK and TPCK had no effect on the inhibition of TRRE. These data suggest that TRRE requires (a) metal ion(s) for its activity. To assess further the metal requirement of TRRE, the enzymatic activity was assayed in the presence of divalent metal ions at 2 mM concentration. TRRE was slightly activated in the presence of $Mn^{2+}$, $Ca^{2+}$, $Mg^{2+}$, and $Co^{2+}$ (% TRRE activities remaining were 157%, 151%, 127%, and 123%, respectively), whereas partial inhibition occurred in the presence of $Zn^{2+}$ and $Cu^{2+}$ (% TRRE activities remaining were 23% and 47%, respectively) (Table 5).

TABLE 5

| Inhibitor | Concentration (mM) | % Control of TRRE activity |
|---|---|---|
| PMSF | 4 | 116 ± 4 |
| AEBSF | 0.5 | 92 ± 8 |
| TLCK | 0.1 | 108 ± 5 |
| TPCK | 0.1 | 107 ± 7 |
| 3,4-DCI | 0.1 | 108 ± 4 |
| EDTA | 2 | 67 ± 7 |
| EGTA | 2 | 73 ± 4 |
| 1,10-Phenanthroline | 2 | 41 ± 6 |
| Phosphoramidon | 0.5 | 84 ± 13 |
| $Ca^{2+}$ | 2 | 151 ± 23 |
| $Mg^{2+}$ | 2 | 127 ± 9 |
| $Mn^{2+}$ | 2 | 157 ± 33 |
| $Zn^{2+}$ | 2 | 23 ± 15 |
| $Co^{2+}$ | 2 | 123 ± 15 |
| $Cu^{2+}$ | 2 | 47 ± 21 |
| $Fe^{2+}$ | 2 | 98 ± 8 |

As shown in Table 6, TRRE with 4 mM $Ca^{2+}$ and 0.1 mM $Zn^{2+}$ showed 189±4% and 122±6% activity (% TRRE activities remaining), respectively (Table 5). As shown previously in Table 7, however, high concentrations of $Zn^{2+}$ (over 2 mM) partially inhibited TRRE activity. Therefore, $Zn^{2+}$ has two opposite effects on TRRE activity based upon its concentrations, while $Ca^{2+}$ can activate TRRE at any concentration. TRRE with 2 mM 1,10-phenanthroline, which is a potent inhibitor of metalloproteases, partially inhibited TRRE and the addition of 2 mM $Ca^{2+}$ or 2 mM $Zn^{2+}$ partially restored TRRE activity inhibited by 2 mM 1,10-phenanthroline. Thus, at least $Ca^{2+}$ and $Zn^{2+}$ modulated TRRE activity. Since the activity of TRRE appears to be metal dependent, TRRE can be a metalloprotease-like enzyme.

TABLE 6

| | % Control of TRRE Activity |
|---|---|
| $Ca^{2+}$ (4 mM) | 189 ± 4 |
| $Zn^{2+}$ (0.1 mM) | 122 ± 6 |
| 1,10-Phenanthroline (2 mM) | 47 ± 9 |
| + $Ca^{2+}$ (2 mM) | 80 ± 15 |
| + $Zn^{2+}$ (2 mM) | 62 ± 6 |

In order to detect MMP activities, aliquots of crude and partially-purified TRRE samples were assayed by gelatin, casein, elastin, and type I collagen zymography according to the method described by Hibbs et al. (1985) *J. Biol. Chem.* 260:2493–2500 with slight modifications. Briefly, these samples were dissolved in nonreducing Laemmli sample buffer without boiling and separated by electrophoresis using an 8% SDS polyacrylamide slab gel impregnated with 1 mg/ml gelatin, casein, elastin, and type I collagen. After electrophoresis, the gel was washed twice, to remove SDS, with 50 mM Tris-HCl buffer, pH 7.6, containing 5 mM $CaCl_2$, 1 µM $ZnCl_2$, 2.5% Triton X-100 (v/v) for 30 min at room temperature with shaking, followed by a brief rinse in washing buffer without Triton X-100. The gel was then incubated in 50 mM Tris-HCl buffer, pH 7.6, containing 5 mM $CaCl_2$, 1 µM $ZnCl_2$, 1% Triton X-100, 0.02% $NaN_3$ at 37° C. overnight with shaking. The enzymatic reaction was terminated by 10% acetic acid, followed by staining with 0.1% Coomassie Brilliant Blue R-250 and destaining with a solution of 10% acetic acid and 10% methanol.

In this assay, clear zones against the blue background indicate the presence of gelatinolytic, caseinolytic, elastinolytic, and type I collagenolytic activity in gelatin, casein, elastin, and type I collagen zymography, respectively. These MMP activities on zymography gels were compared with the TRRE activity of the corresponding samples. For the 4 crude TRRE samples, THP-1 cells at a density of $1 \times 10^6$ cells/ml were stimulated with or without $10^{-6}$ M PMA for 30 min in 0% or 1% FCS-containing RPMI-1640 followed by 2 more hours incubation in PMA-free medium with the same concentrations of FCS. The partially-purified TRRE sample was prepared from serum-free TRRE source as described. For the positive control of MMPs, THP-1 cells were incubated in serum-free RPMI-1640 with $10^{-8}$ M PMA for 24 hours, and after the culture medium was washed away, the cells were incubated in fresh serum-free medium without PMA for additional 24 hours and then the supernatant was harvested.

Figure 10A:
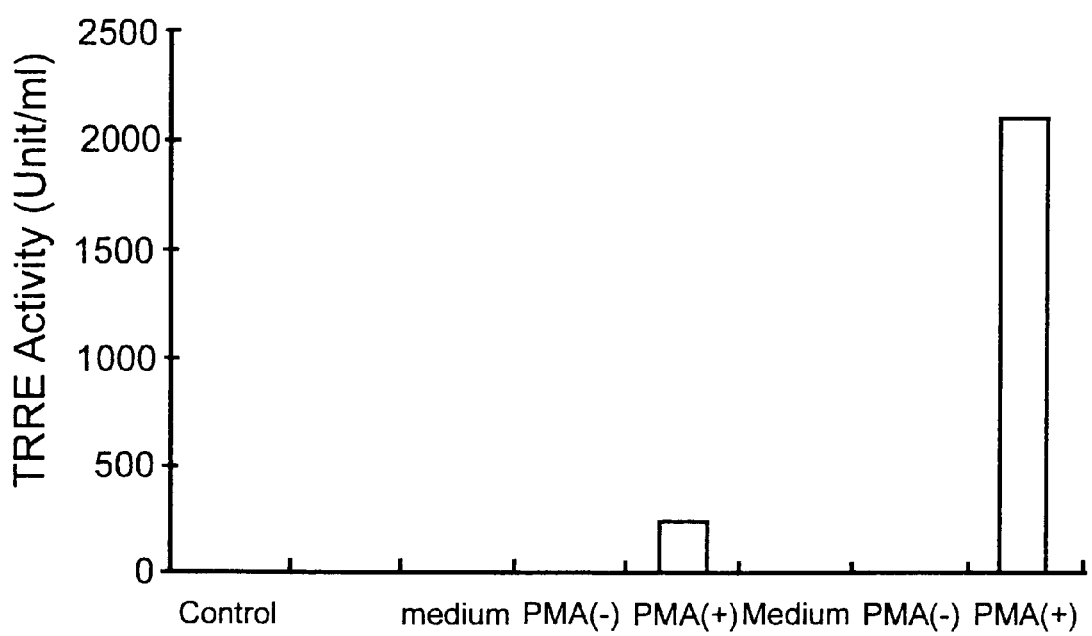
FIG. 10A is a bar graph depicting TRRE activity in PMA stimulated THP-1 cells and controls. 10B is a photograph of gelatin zymography of the samples listed in 10A.
Figure 10B:
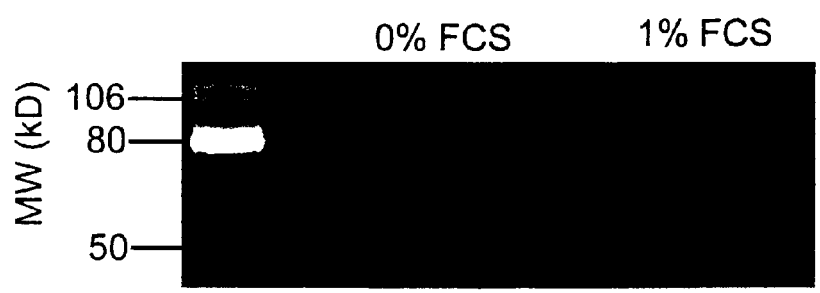
FIG. 10C is a bar graph depicting TRRE activity of gelatin zymography on a partially purified TRRE sample.
FIG. 10D is a photograph of gelatin zymography corresponding to the samples in 10C.
Figure 10C:
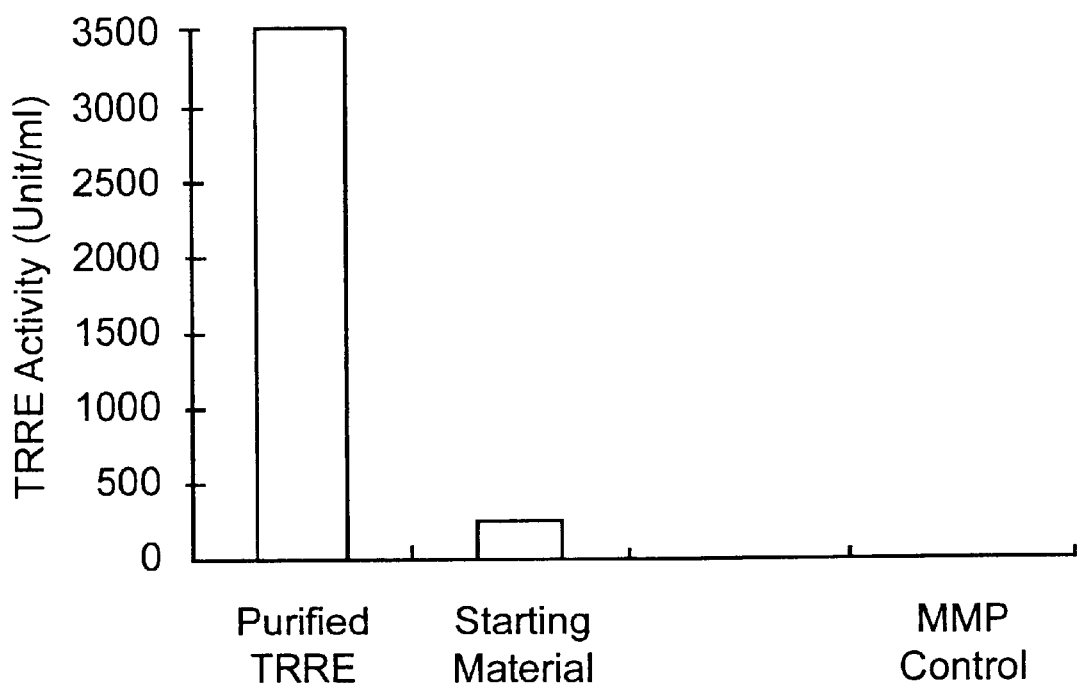
Figure 10D:

Previously, MMPs have been reported to be responsible for the cleavage of pro-TNF. Gearing et al. (1994); and Gearing et al. (1995). Since TRRE appears to be a metalloprotease, zymography was performed to detect MMP activities in TRRE samples. Zymography on gelatin-, casein-, elastin-, and type I collagen-containing gels may primarily detect 72 kD gelatinase A and 92 kD gelatinase B (MMP-2 and -9), stromelysin (MMP-3) and matrilysin (MMP-7), macrophage metalloelastase (MMP-12), and interstitial collagenase (MMP-1), respectively. These MMPs have been shown to be secreted by macrophages. Hibbs et al. (1985); Chin et al. (1985) *J. Biol. Chem.* 260:12367–12376; Miyazaki et al. (1990) *Cancer Res.* 50:7758–7764; Senior et al. (1991) *J. Biol. Chem.* 266:7870–7875; Dansette et al. (1979) *Anal. Biochem.* 97:340–345. FIGS. 10A and 10B show the relationship between TRRE activity and gelatin zymography on crude and partially-purified TRRE samples, respectively. Each is a representative example of four different substrate-impregnated zymography gels. Only PMA-stimulated THP-1 cells in 0% and 1% FCS-contained supernatants produced TRRE at concentrations of 217 and 2,096 U/ml, respectively (FIG. 10A). The latter crude sample with 1% FCS was treated in the same manner as the enzyme source of TRRE previously described. On gelatin zymography, two gelatinolytic bands derived from gelatinase A and B were detected only in three 1% FCS-contained samples with completely equal intensity, suggesting that these MMP activities resulted not from TRRE but from 1% FCS. No gelatinolytic activity was detected in partially-purified TRRE without FCS, contrary to its high TRRE activity (3,514 U/ml) (FIG. 10B). Despite the strong gelatinolytic activities, the positive control had no TRRE activity. The casein, elastin, and type I collagen zymography gels showed no MMP activity in either crude or partially-purified samples. Therefore, TRRE appears to have a distinctly different activity than that of known macrophage-associated MMPs.

In order to determine the molecular weight of TRRE by gel filtration, TRRE was obtained from PMA-stimulated THP-1 cells in RPMI-1640 with 1% FCS. This source was adjusted to 100% saturation with ammonium sulfate and the precipitate was pelleted and resuspended in PBS followed by dialysis as described for the partial purification. This concentrated TRRE (1 ml) was loaded onto a Sephadex G-150 column (1.0×30 cm) (Pharmacia Biotech) which was equilibrated in 10 mM Tris-HCl, 60 mM NaCl, pH 7.0. The flow rate was 1 ml/min, and 1-ml fractions were collected for the measurement of TRRE activity, soluble p75 TNF-R, and absorbance at 280 nm.

Figure 11:
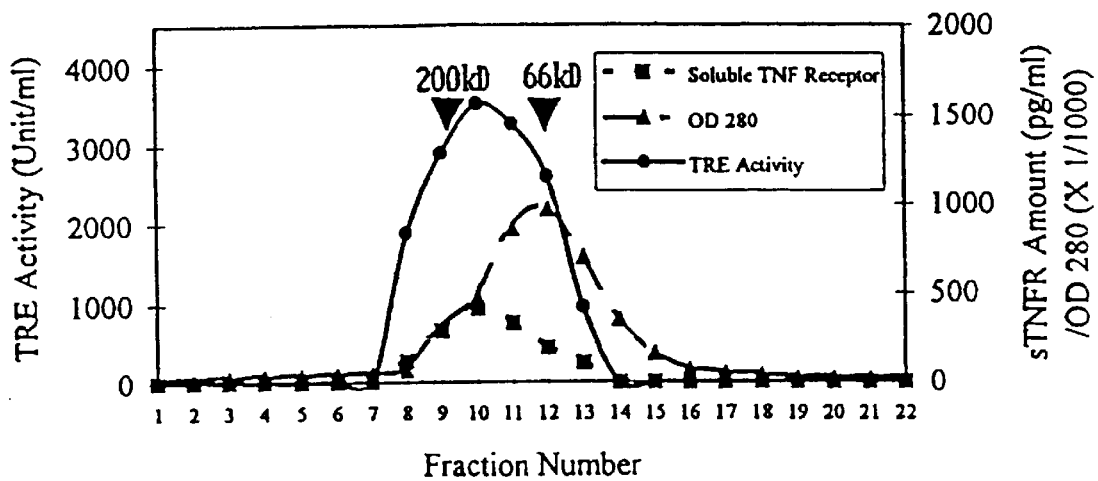
FIG. 11 is a graph depicting the TRRE activity of fractions obtained using a Sephadex G-150 column. Each fraction (1 ml) was assayed for TRRE activity (●) and soluble p75 TNF-R (■), and measured for absorbance at 280 nm (▲). The peak elutions of standards, beta-amylase (200 kDa) and bovine serum albumin (66 kDa) are shown.

The results obtained indicate that TRRE activity was detected as a single peak accompanied by a similar profile of soluble p75 TNF-R in gel filtration (FIG. 11). The peak elution of both TRRE and soluble p75 TNF-R was at Fraction Number 10, which had migrated approximately at 150 kDa molecular weight according to the standards. The same sample was also applied to DEAE-Sephadex chromatography and a similar profile between TRRE and soluble p75 TNF-R was obtained. This evidence suggests that some of TRRE and sTNF-R, an enzymatic product of TRRE, remain bound in the reacting solution and migrate as a complex in both gel filtration and DEAE columns.

In order to assure that TRRE was being specifically purified, purified TRRE was subject to affinity chromatography on soluble p75 TNF-R Sepharose affinity chromatography. The activity of partially-purified TRRE was adjusted to 5,000 U/ml with 10 mM Tris-HCl, 60 mM NaCl, pH 7.0. This diluted TRRE was incubated with C75R cells growing in logarithmic phase in a 150 mm cell culture plate for 30 min at 37° C. in 5 % $CO_2$ (15 ml of TRRE sample per plate). The supernatants from five plates (75 ml) were collected and centrifugally concentrated to approximately 2 ml with Centriprep-10 filter (Amicon). This concentrated sample was applied directly to soluble p75 TNF-R affinity chromatography (soluble p75 TNF-R- and Affigel 10 (Bio-Rad)-conjugated column) (column size; 1×2 cm) at 4° C. which was equilibrated with 10 mM Tris-HCl, 60 mM NaCl, pH 7.0. The column was then washed with 10 ml of the same Tris-buffer and eluted with 5 ml of elution Buffer (ImmunoPure elution Buffer, Pierce). The eluate from the affinity column was applied to gel filtration (Naps 5 column, Pharmacia) to change the elution buffer for the buffer of 10 mM Tris-HCl, 60 mM NaCl, pH 7.0 and 2 ml fractions were collected. Each fraction was measured for TRRE activity and absorbance at 280 nm. The total TRRE activity from the active fractions of gel filtration was considered as the TRRE activity in the eluate of soluble p75 TNF-R-affinity chromatography. The flow through and washing of the affinity column, whose buffer was 10 mM Tris-HCl, 60 mM NaCl, pH 7.0, were directly measured for TRRE activity without gel filtration.

Figure 12:
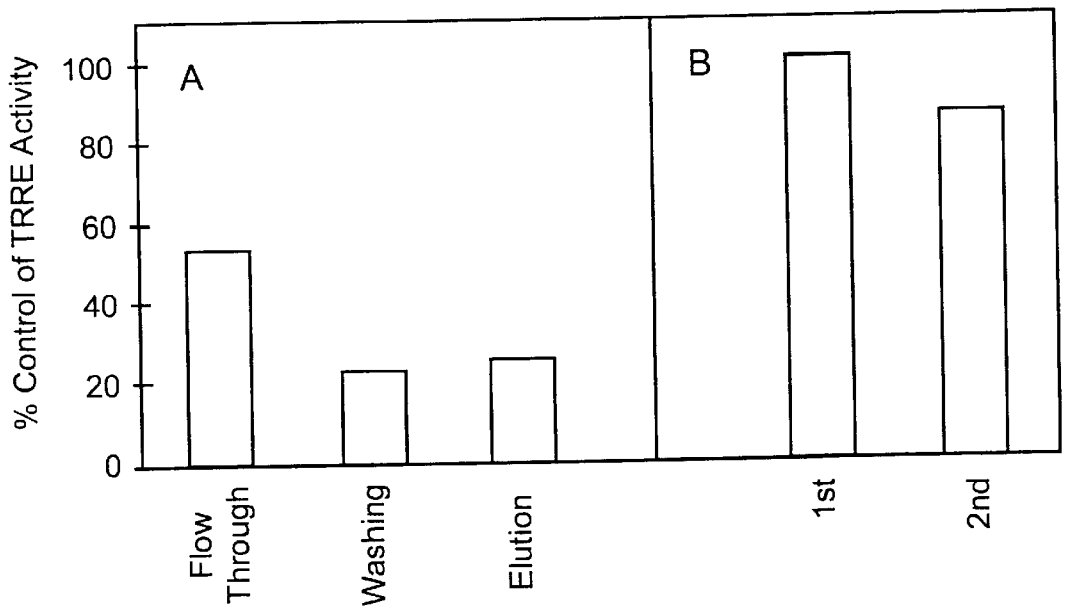
FIG. 12A depicts the results obtained from the soluble p75 TNF-R affinity column. Total amount of recovered TRRE from the affinity column is adjusted to 100%. 12B depicts successive treatment of the same TRRE sample to C75R cells. TRRE activity of the first treatment to C75R is adjusted to 100%.
Figure 13:
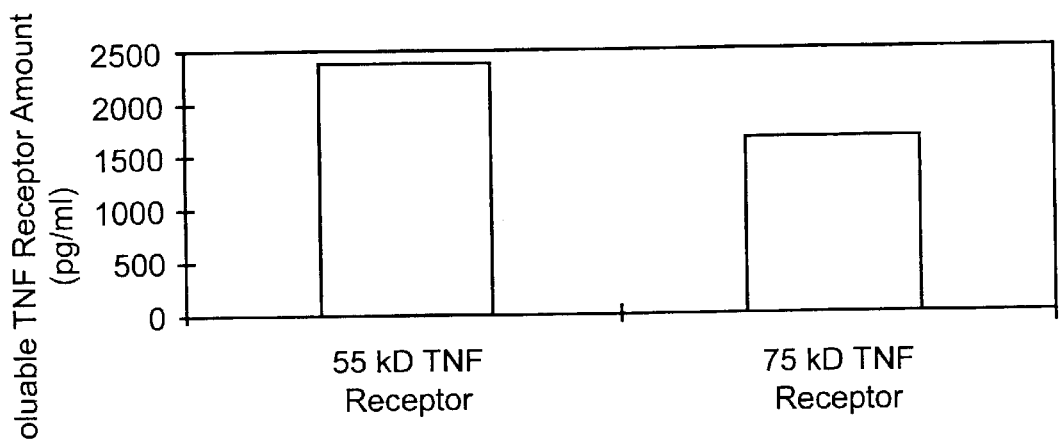
FIG. 13 depicts the results obtained from cleavage of both p55 and p75 TNF-R on THP-1 cells by TRRE.

To verify the hypothesis that a bound form of TRRE and its enzymatic product, sTNF-R, exists in vitro, the reacting solution between TRRE and its substrate-expressing C75R cells was applied to soluble p75 TNF-R-affinity chromatography as described. Among the total amount of recovered TRRE from soluble p75 TNF-R-affinity column (100%), 53%, 22%, and 25% was distributed in the flow through, the wash, and the elution, respectively (FIG. 12A). This data means that 25% of active TRRE may combine with soluble p75 TNF-R affinity column even after TRRE was once treated with its substrate and then that their binding form might exist in vivo.

The stability of partially-purified TRRE was investigated against various temperatures and pH values. TRRE activity was stable when stored at −70° C. TRRE activity, however, was reduced by incubation at 4° C. for 2 days, heating at 56° C. for 30 min, and boiling for 15 min to 82%, 84% and 16% of its initial activity, respectively. TRRE samples treated at various pH levels were pre-incubated at 37° C. for 30 min and then applied to the TRRE assay after adjusting the pH of all samples to 7.4. TRRE samples pre-incubated at pH 6.0, 7.0, 8.0, and 9.0 showed 52%, 100%, 69%, and 73%, respectively of TRRE activity contained in the original supernatant (pH 7.4), respectively (Table 8). Thus, the optimal pH of TRRE was around 7.0 and its activity deteriorated more in acidic than basic conditions. T

TABLE 8

| Temperature | % Control of TRRE Activity | pH | % Control of TRRE Activity |
|---|---|---|---|
| 4° C. for 48 hours | 82 | 6.0 | 52 |
| 56° C. for 30 min. | 84 | 7.0 | 100 |
| 100° C. for 15 min. | 16 | 8.0 | 69 |
|  |  | 9.0 | 73 |

Since TRRE and sTNF-R may remain associated in the reaction solution in vitro, their affinity was investigated to determine whether this complex functioned as an inhibitor or a protector of TRRE in the enzymatic reaction. Partially-purified TRRE was incubated with C75R cells growing in logarithmic phase in a 150 mm cell culture plate for 30 min at 37° C. in 5% $CO_2$. TRRE activity was assayed before and after the treatment of the culture plate. During the incubation, the substrate (TNF-R) was considered to be much more abundant than the enzyme (TRRE). Relative to the TRRE activity before the reaction, 86% TRRE activity was detected even after the reaction (FIG. 12B). Therefore, although TRRE was treated once with excessive substrate, thereby creating conditions in which there is a high concentration of TRRE/sTNF-R complex, TRRE activity remained comparatively high against the next reaction. Thus, this TRRE/sTNF-R complex form was not inhibitory for TRRE.

Due to the metal requirement of TRRE indicated by the effect of chelating agents and divalent heavy metal ions, TRRE appears to be a metalloprotease. The reason for incomplete inhibition by chelating agents may be because this partially purified TRRE from DEAE-Sephadex chromatography consists of several other enzymes or factors which also have an influence on the cleavage of TNF-R. Another explanation is that the concentration of chelating agents and divalent metal ions necessary to achieve complete inhibition was not attained due to their toxicities to C75R cells in this assay system. The inhibition of TRRE activity by 1,10-phenanthroline was partially restored by $Ca^{2+}$ and $Zn^{2+}$ independently, suggesting that several metal ions including $Ca^{2+}$ and $Zn^{2+}$ are related to the activity or stability of TRRE. Two reports describe the involvement of a metalloprotease in the production of sTNF-R by utilizing a specific metalloprotease inhibitor, TNF-α protease inhibitor (TAPI).

TAPI blocks the shedding of soluble p75 and p55 TNF-R, respectively. Crowe et al. (1995); and Mullberg et al. (1995). Moreover, the processing of pro-TNF on the cell membrane was reported to be dependent on a MMP-like enzyme). Gearing et al. (1994); and Gearing et al. (1995). MMPs are a family of structurally related matrix-degrading enzymes that play a major role in tissue remodeling and repair associated with development and inflammation. Matrisian (1990) *Trends Genet.* 6:121–125; Woessner (1991) *FASEB J.* 5:2145–2154; and Birkedal-Hansen et al. (1993) *Crit. Rev. Oral Biol. Med.* 4:197–250. Pathological expression of MMPs is responsible for tumor invasiveness, osteoarthritis, atherosclerosis, and pulmonary emphysema. Mignatti et al. (1986) *Cell* 47:487–498; Khokha (1989) *Science* 243:947–950; Dean et al. (1989) *J. Clin. Invest.* 84:678–685; Henney et al. (1991) *Proc. Natl. Acad. Sci. USA* 88:8154–8158; and Senior et al. (1989) *Am. Rev. Respir. Dis.* 139:1251–1256. MMPs are $Zn^{2+}$-dependent enzymes which have $Zn^{2+}$ in their catalytic domains. $Ca^{2+}$ stabilizes their tertiary structure significantly. Lowry et al. (1992) *Proteins* 12:42–48; and Lovejoy et al. (1994) *Science* 263:375–377. Thus, according to the similar metal dependency, TRRE may be a part of the MMPs family of which 11 MMPs have been cloned.

It has been reported that not only metalloproteases but also serine proteases are involved in the cleavage of TNF-R by adding PMA and serine protease inhibitors simultaneously in the culture medium of THP-1 cells. These results indicate that at least two different kinds of proteases are involved in the induction phase of TRRE and that these enzymes form a cascade for their activation. According to the results presented herein, however, serine protease inhibitors had no effect toward partially-purified TRRE samples whose enzymatic activity was already established. Bjomberg et al. (1995); and Hwang et al. (1993). This evidence suggests that TRRE may be a metalloprotease and a serine protease might act on the activation of TRRE. Most MMPs are actually secreted in an inactive soluble proenzyme form (zymogen) which undergoes proteolytic modulation by several serine proteases and an autocatalytic mechanism to be active forms. Van Wart and Birkedal-Hansen (1990) *Proc. Natl. Acad. Sci. USA* 87:5578–5582.

Human monocytes and macrophages have been shown to produce several MMPs; however, no gelatinolytic, caseinolytic, elastinolytic, and type I collagenolytic activity was detected in crude and partially-purified TRRE.

The induction patterns of TRRE and known MMPs by PMA stimulation are quite different. In order to induce MMPs, monocytic U-937 cells, fibrosarcoma HT-1080 cells, or peritoneal exudate macrophages (PEM) usually have to be stimulated for one to three days with LPS or PMA. On the other hand, as compared with this prolonged induction, TRRE is released very quickly in culture supernatant following 30 min of PMA-stimulation. As disclosed in Example 2, TRRE is stored in the cell very close to the cell membrane to be secreted immediately by PMA-stimulation, and TRRE is synthesized very quickly within 2 hours also by PMA-stimulation. Therefore, judging from zymography gel data and the different induction patterns by PMA, TRRE cannot be classified into one of the pre-existing MMP families, despite their resemblance regarding metal-requirement and involvement of serine proteases in their activation.

Soluble TNF-R has been shown to bind to TNF or LT and form a complex consisting of 3 sTNF-R with 3 TNF or LT. Banner et al. (1993). According to gel filtration analysis presented above, the profile of TRRE and soluble p75 TNF-R was quite similar, with both peaks approximately at 150 kDa. Since the molecular size of soluble p75 TNF-R was reported to be 40 kDa, this suggests that sTNF-R exist as a complex formed with TRRE or TNF, or otherwise as homo oligomers. The hypothesis that TRRE and sTNF-R form a complex in vitro was confirmed by the experiment that 25% TRRE activity was recovered from soluble p75 TNF-R affinity column. This means that free TRRE has the ability to bind to its catalytic product, sTNF-R. The remaining 75% which did not combine to the affinity column may already be bound to sTNF-R or may not have enough affinity to bind to sTNF-R even though it is in a free form.

Although a considerable amount of enzyme product (EP) complex is thought to exist in the reacting solution, TRRE retained 86% of its activity after treated once with excessive substrate, suggesting that this complex can be easily separated when it meets new substrate. This EP complex does not seem to inhibit the enzymatic reaction of TRRE significantly. While sTNF-R is a potent inhibitor against the biological activities of TNF and LT, it was also shown that sTNF-R has another role in stabilizing TNF activity in vitro. Aderka et al. (1992) *J. Exp. Med.* 175:323–329. Thus sTNF-R might act as a stabilizer not only for TNF, but also for TRRE by composing complex formation. This EP complex between TRRE and sTNF-R may be formed presumably under in vitro conditions, however it is possible that TRRE, sTNF-R and TNF make up several types of complexes in vivo as well as in vitro, and therefore may have physiological significance.

EXAMPLE 5

Biological Effect of TRRE

In this Example, the effect and biological significance of TRRE is investigated, including (a) substrate specificity and (b) function in vitro.

Fluorescein isothiocyanate (FITC)-conjugated anti-CD54, FITC-conjugated goat anti-rabbit and mouse antibodies, mouse monoclonal anti-CD30, anti-CD11b and anti-IL-1R (Serotec, Washington D.C.) were utilized in this study. Rabbit polyclonal anti-p55 and p75 TNF-R were constructed according to the method described by Yamamoto et al. (1978) *Cell Immunol.* 38:403–416. THP-1 cells were treated for 30 min with 1,000 and/or 5,000 U/ml of TRRE eluted from the DEAE-Sephadex column and transferred to 12×75 mm polystyrene tubes (Fischer Scientific, Pittsburgh, Pa.) at $1 \times 10^5$ cells/100 µl/tube. The cells were then pelleted by centrifugation at 350×g for 5 min at 4° C. and stained directly with 10 µl FITC-conjugated anti-CD54 (diluted in cold PBS/0.5% sodium aside), indirectly with FITC-conjugated anti-mouse antibody after treatment of mouse monoclonal anti-CD11b, IL-1R and CD30 and also indirectly with FITC-conjugated anti-rabbit antibody after treatment of rabbit polyclonal anti-p55 and p75 TNF-R.

THP-1 cells stained with each of the antibodies without treatment of TRRE were utilized as negative controls. The tubes were incubated for 45 min at 4° C., agitated every 15 min, washed twice with PBS/2% FCS, repelleted and then resuspended in 200 µl of 1% paraformaldehyde. These labeled THP-1 cells were analyzed using a fluorescence activated cell sorter (FACS) (Becton-Dickinson, San Jose, Calif.) with a 15 mW argon laser with an excitation of 488 nm. Fluorescent signals were gated on the basis of forward and right angle light scattering to eliminate dead cells and aggregates from analysis. Gated signals ($10^4$) were detected at 585 BP filter and analyzed using Lysis II software. Values were expressed as percentage of positive cells, which was calculated by dividing mean channel fluorescence intensity (MFI) of stained THP-1 cells treated with TRRE by the MFI of the cells without TRRE treatment (negative control cells).

In order to test the in vitro TNF cytolytic assay by TRRE treatment the L929 cytolytic assay was performed according to the method described by Gatanaga et al. (1990b). Briefly, L929 cells, an adherent murine fibroblast cell line, were plated (70,000 cells/0.1 ml/well in a 96-well plate) overnight. Monolayered L929 cells were pretreated for 30 min with 100, 500 or 2,500 U/ml of partially-purified TRRE and then exposed to serial dilutions of recombinant human TNF for 1 hour. After washing the plate with RPMI-1640 with 10% FCS to remove the TRRE and TNF, the cells were incubated for 18 hours in RPMI-1640 with 10% FCS containing 1 µg/ml actinomycin D at 37° C. in 5% $CO_2$. Culture supernatants were then aspirated and 50 µl of 1% crystal violet solution was added to each well. The plates were incubated for 15 min at room temperature. After the plates were washed with tap water and air-dried, the cells stained with crystal violet were lysed by 100 µl per well of 100 mM HCl in methanol. The absorbance at 550 nm was measured using an EAR 400 AT plate reader (SLT-Labinstruments, Salzburg, Austria).

Figure 15:
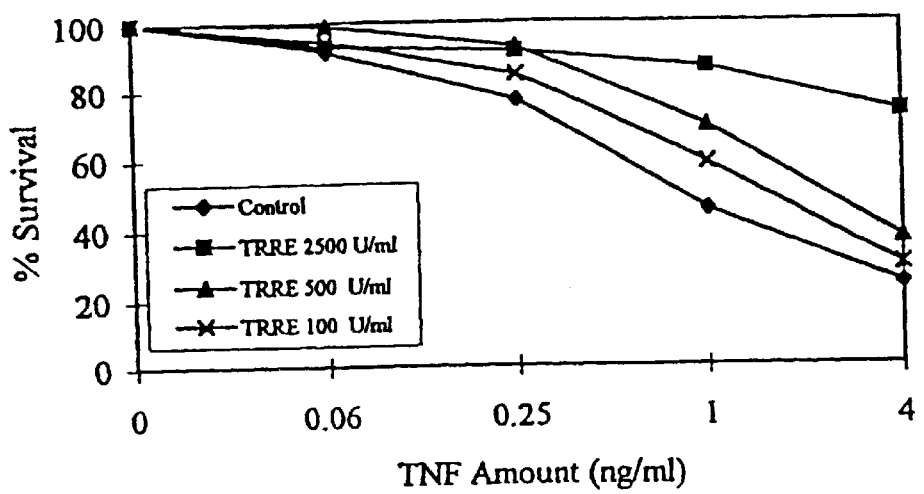
FIG. 15 is a graph depicting the results of a modified in vitro TNF cytolytic assay by TRRE treatment to L929 cells.

TRRE was originally defined as a protease which truncated the human p75 TNF-R that was overexpressed on cDNA-transduced COS-1 cells (C75R). To investigate whether TRRE may truncate not only p75 but also p55 TNF-R on human cells, partially-purified TRRE from human THP-1 cells was applied to THP-1 cells which express low levels of both p55 and p75 TNF-R (approximately 1,500 receptors/cell by Scatchard analysis, data not shown). TRRE eluate from the DEAE-Sephadex column was added to THP-1 cells ($5 \times 10^6$ cells/ml) at a final TRRE concentration of 1,000 U/ml for 30 min. The concentration of soluble p55 and p75 TNF-R in that supernatant was measured by soluble p55 and p75 TNF-R ELISA. TRRE was found to truncate both human p55 and p75 TNF-R on THP-1 cells and released 2,382 and 1,662 pg/ml soluble p55 and p75 TNF-R, respectively (FIG. 15). Therefore, TRRE was capable of truncating human p75 TNF-R on C75R cells and both human p55 and p75 TNF-R on THP-1 cells.

Figure 14:
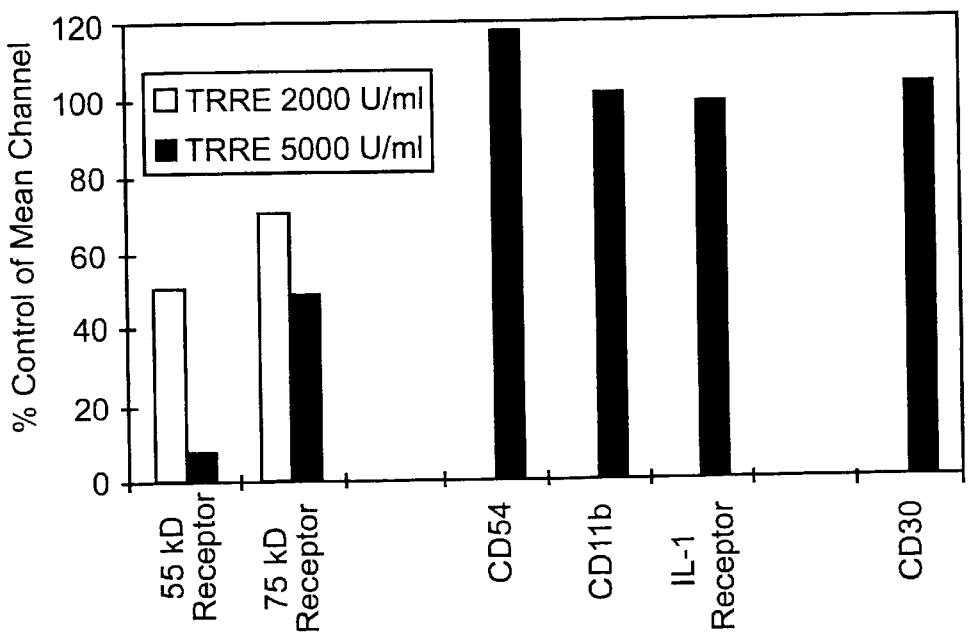
FIG. 14 is a graph depicting the effect of TRRE against various cell surface antigens.

For substrate specificity of TRRE, the cell surface expression of p55 and p75 TNF-R, CD54, CD11b, IL-1R, and CD30 on THP-1 cells treated with TRRE was investigated by flow cytometry after labeling THP-1 cells with specific antibodies as described above. Following treatment of THP-1 cells with 5,000 U/ml TRRE, the expression of p55 and p75 TNF-R had decreased to 8% and 49% (percent control), respectively (FIG. 14), and a dose response to TRRE (1,000 and 5,000 U/ml) was seen in the truncation of p55 and p75 TNF-R. No significant change, however, was found in the expression of CD54, CD11b, IL-1R and CD30 with (5,000 U/ml) and without TRRE treatment (FIG. 14). Among the receptors and antigens examined, TRRE was effective against only p55 and p75 TNF-R. The % control was obtained by dividing mean channel fluoresence intensity (MFI) of stained THP-1 cells treated with TRRE by the MFI of the cell without TRRE (control).

In order to investigate the in vitro biological significance of shedding sTNF-R by TRRE, L929 cytolytic assay, modified by the addition of TRRE treatment, was performed as described above. L929 cells without TRRE treatment were utilized as a negative control. L929 cells were pretreated for 30 min with 100, 500 or 2,500 U/ml TRRE from DEAE-fractions and then exposed to serial dilutions of recombinant human TNF for 1 hour. After washing the plate with medium to remove the TRRE and TNF, the cells were incubated for 18 hours in 1 µg/ml ActD, stained with crystal violet (the live cells stained blue) and then assayed for their cytolysis with measuring absorbance at 550 nm. The results obtained and depicted in FIG. 15. The ratios of surviving L929 cells pretreated with 0 (negative control), 100, 500 and 2,500 U/ml TRRE with 4 ng/ml TNF stimulation to those cells without TNF stimulation were 24%, 30%, 38%, and 74%, respectively. TRRE-treated L929 cells were thus protected against TNF-induced lysis, and more importantly, a dose-response for this protection was detected.

The substrate-specificity of TRRE was investigated using membrane receptors and antigens other than the two TNF-Rs. These receptors and antigens are expressed at sufficient levels on THP-1 cells to be detected by FACS analysis including (i) IL-1R, whose soluble form is known to be produced by proteolytic cleavage, (ii) CD30 (ki-1), which belongs to the same receptor family as TNF-R (TNF-R/NGF-R superfamily) and whose soluble form is produced presumally by a $Zn^{2+}$-dependent metalloprotease, (iii) CD54 (ICAM1), which belongs to immunoglobulin superfamily of adhesion molecules including VCAM-1 and is known to have a soluble form, and (iv) CD11b, which belongs to the integrin family of adhesion molecules and which has not been shown to have a soluble form. The FACS analysis presented above revealed that TRRE is very specific to only the cleavage of both TNF-Rs and did not affect any other membrane receptors and antigens which have soluble forms. In addition, the ability of TRRE to cleave both TNF-Rs was supported by the soluble p55 and p75 TNF-R ELISA data presented herein.

TRRE down-regulated the expression of TNF-R on the cell-surface of L929 cells in the TNF binding assay. Pre-treatment with TRRE protected L929 cells from the killing activity of TNF. Thus, TRRE may control TNF activity by two methods; by reducing the number of TNF-R or by producing sTNF-R which bind and inactivate TNF. Cleavage of TNF-R by TRRE may possibly protect TNF-sensitive cells and organs in diseases associated with high levels of TNF. On the other hand, while high serum levels of TNF and sTNF-R are often associated with various types of cancers, cleavage of TNF-R by TRRE may condition cancer cells more resistant to the effects of TNF.

EXAMPLE 6

Purification of TRRE

TRRE was purified to apparent homogeneity by 100% saturated ammonium sulfate precipitation, DEAE-Sephadex chromatography, and native PAGE. Partially-purified TRRE was fractionated by SDS-PAGE and several protein bands were apparent. Two protein bands, at 60 kDa and 37 kDa, were selected as possible TRRE candidates.

THP-1 cells were cultured in 8 roller bottles (Corning, Corning, N.Y.) per preparation with 500 ml of 10% FCS-contained RPMI-1640 per roller bottle. The cells were collected for the induction of TRRE when the cell density reached approximately $1\times10^6$ to $1.5\times10^6$ cells/ml. The cells were then incubated in 1% FCS-contained medium with $10^6$ M phorbol 12-myristate 13-acetate PMA (Sigma) for 30 min and were washed to obtain PMA-free sample. After washing serum free medium, the cells were incubated for an additional 2 hours in a 4 liter, 1% FCS containing medium with PMA and the supernatants were collected as the source of the enzyme.

The cell-free supernatants were concentrated by the 100% saturated ammonium sulfate precipitation method. All of the following procedures were performed at 4° C. 69.7 g of solid ammonium sulfate per 100 ml was slowly added to the collected supernatant over 4 hours with gentle stirring followed by an additional 1 hour of stirring. The precipitate was collected by centrifugation at 10,000×g for 30 min and redissolved in PBS at approximately two times the volume of the pellet. The re-dissolved precipitates was then dialyzed against a buffer of 10 mM Tris-HCl, 60 mM NaCl, pH 7.0 (buffer 1) with dialysis tubing which had a nominal molecular weight cut-off (NMWC) of about 6,000 to 8,000 for 60 hours.

The concentrated samples were diluted in the same volume of a buffer of 50 mM Tris-HCl, 60 mM NaCl, pH 8.0 (buffer 2) and then applied onto an anion-exchange chromatography, DEAE-Sephadex A-25 (Pharmacia Biotech, Uppsala, Sweden) (2.5×10 cm), which was previously equilibrated with buffer 2. Following washing of the column with (150 ml) of buffer 2, the sample was eluted with an ionic strength linear gradient (total volume; 250 ml) of 60 mM (buffer 2) to 250 mM NaCl, 50 mM Tris-HCl, pH 8.0. The flow rate was 1 ml/min, and 4-ml fractions of sample A and 3-ml fractions of sample B were collected. Each fraction was measured for absorbance at 280 nm and assayed for TRRE activity. Several DEAE fractions with the highest specific TRRE activity (the highest value of TRRE units/A280) were collected and applied to the further steps.

These active DEAE fractions were centrifugally concentrated to approximately 500 μl with Centriprep-10 filter (10,000 MW cut-off membrane) (Amicon). This concentrated sample was then applied to several lanes of a 6% polyacrylamide gel electrophoresis (PAGE) (15×10 cm) under non-denaturing native conditions with cooling to recover the biological activity of TRRE after electrophoretic separation. One complete lane was cut off vertically from the side of the native PAGE slab gel and stained with a silver staining kit (Bio-Rad). The remainder of the native PAGE gel was then sliced horizontally into 5 mm strips and each strip was eluted in 1 ml of PBS at 4° C. overnight with shaking. Each eluate was assayed for TRRE activity. The TRRE activity of each eluate was compared with protein bands of the silver-stained native gel for the localization of TRRE. Next, each TRRE active fraction eluted from native PAGE gel was centrifugally concentrated to approximately 50 μl with Microcon-10 filter (10,000 MW cut-off membrane) (Amicon). These concentrated samples were applied to 8% SDS-PAGE under denaturing conditions, and stained with Coomassie Brilliant Blue R-250 (CBB). The stained gel was then used to determine the existence of a correlation between TRRE activity and the intensity of the protein bands.

With 4 L of the original THP-1 cell supernatant (8 roller bottles), representing one lot, the PMA-stimulated THP-1 cells were prepared at a density of $1.5\times10^6$ cells/ml, and 3,679±144 ml and 3,623±118 ml of the TRRE sources were obtained for sample A and sample B, respectively (mean±standard error). After 100% saturated ammonium sulfate precipitation, sample A and sample B were dissolved in 49±5 ml and 4.5±1.1 ml of PBS and reached a final volume of 109±12 ml after 60 hours of dialysis and 13.2±2.7 ml after 24 hours of dialysis, respectively. The final fold-concentrations of sample A and sample B were 34.2±2.3 times and 268±26 times, respectively. Sample A had 4,327±1,150 U/ml of TRRE and a total amount of $(15.9\pm2.5)\times10^6$ U in the original supernatant. After dialysis for 60 hours, the concentrated sample A had $(12.1\pm2.9)\times10^4$ U/ml and a total of $(13.2\pm2.1)\times10^6$ U of TRRE. Therefore, 81.6±8.1% TRRE was recovered in sample A through 100% saturated ammonium sulfate precipitation. For sample B, TRRE activity in the original supernatant was unable to be assayed because of the contamination of $10^{-6}$ M PMA. After ammonium sulfate precipitation followed by intensive dialysis for 24 hours to remove ammonium sulfate and PMA, the concentrated sample B had $(21.9\pm2.1)\times10^4$ U/ml and a total of $(28.9\pm3.8)\times10^5$ U of TRRE which corresponded to about one fifth of total TRRE of sample A.

Figure 16:
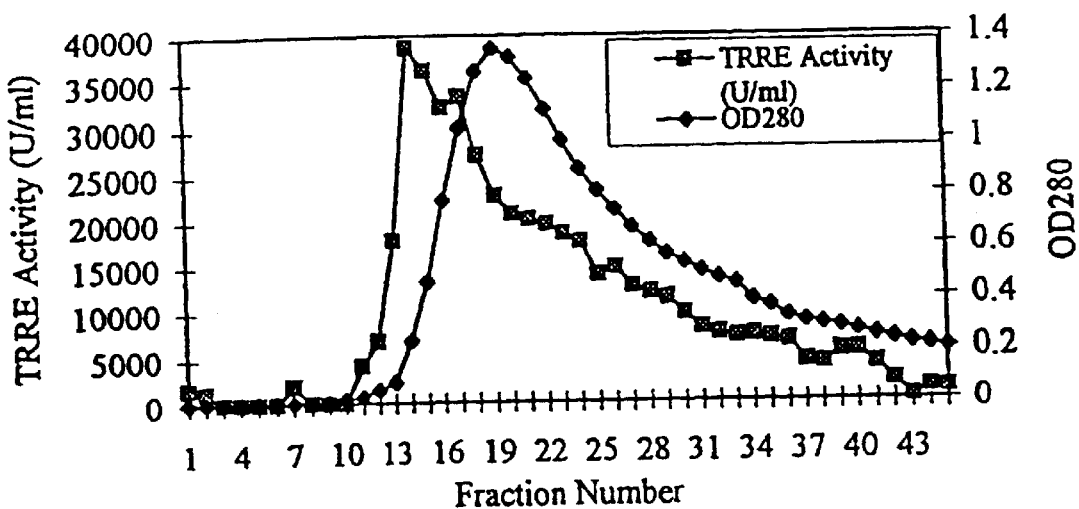
FIG. 16 is a graph depicting the DEAE-Sephadex profile of sample A obtained in Example 5.
Figure 17:
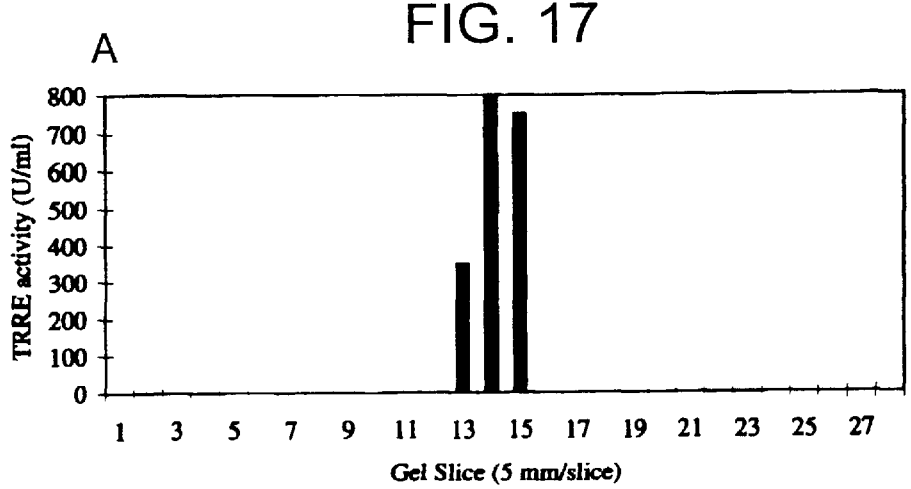
FIG. 17 is a photograph of a native PAGE profile of sample B obtained in Example 5. 17A depicts the TRRE activity of each sliced strip (fraction) and 17B depicts the silver-stained native PAGE corresponding to 17A. In 17B, the left side is the top of the gel.
Figure 18:
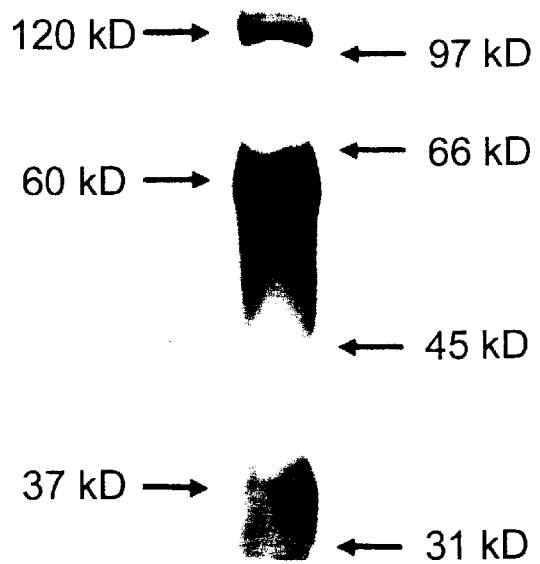
FIG. 18 is a photograph of an SDS-PAGE of the highest TRRE eluate of native PAGE of sample A obtained in Example 5.

One lot of dialyzed sample A was loaded onto a DEAE-Sephadex column with 4 aliquots. With this column, both proteins and TRRE activity eluted as similarly-shaped single broad peaks which tapered gradually in the latter fractions. The peak protein fraction (A280) and TRRE activity fraction was always found near Fr. 20 and Fr. 15, respectively (FIG. 16). Thus, TRRE was eluted in 4 or 5 fractions prior to the main proteins which is predominantly comprised of bovine serum albumin (BSA). The concentration of the highest TRRE fraction was $(25.5\pm2.4)\times10^3$ U/ml. With this column, 0.3±0.2%, 4.5±1.1%, and 35.1±6.3% TRRE activity were recovered in flow through, washing, and all fractions, respectively, compared to the original TRRE activity loaded on the column (100%). Among the total proteins recovered (100%), 21.8±2.5%, 32.6±2.8%, and 45.6±5.3% proteins were obtained in flow through, washing, and all fractions, respectively.

On the other hand, due to extremely low amounts of proteins, two lots of sample B were combined and loaded onto a DEAE-Sephadex column per column purification. TRRE activity eluted as a broad single peak as in sample A (data not shown). The elution of proteins, however, held at a low value once it reached a certain point, and so no significant peak was detected. The peak of TRRE activity was at Fr. 18 and the proteins gradually reached their highest value near Fr. 40. With this column, 0±0%, 2.2±0.4%, and 11.2±1.3% TRRE activity were recovered in flow through, washing, and all fractions, respectively, compared to the original TRRE activity loaded on the column (100%). 9.5±3.7%, 42.4±5.5%, and 48.1±6.1% of the total proteins recovered (100%) were located in the flow through, washing, and all fractions, respectively, very similar to the percentages of sample A. The recovered efficacy of TRRE in sample B, however, was lower than sample A.

Several DEAE fractions with the highest relative TRRE activity were concentrated and loaded onto a native PAGE. TRRE activity of sample A was detected in 4 fractions (strips) from Fr. 8 to 11 in the native PAGE. The highest TRRE activity was at Fr. 9 or 10 which had $(9.3\pm1.6)\times10^3$ U/ml activity and the total recovery of TRRE activity was 16.2±4.1% through concentration and native PAGE. The highest TRRE fraction was found with a tight group of several bands detected by silver staining of the native PAGE gel. On the other hand, TRRE activity of sample B was detected in 3 fractions of Fr. 13 to 15 in native PAGE. The total recovery rate of TRRE activity from these 3 fractions was 8.7±1.0% through concentration and native PAGE. Only 2 or 3 silver-stained protein bands were detected at Fr. 13–15 of the TRRE-active eluates in the native PAGE.

SDS-PAGE of concentrated active eluates from the native PAGE revealed several protein bands in sample B. The TRRE eluate with highest-activity had protein bands at approximate 120 kDa, 60 kDa and 37 kDa, while several other TRRE-active eluates had protein bands at 70 kDa, 55 kDa, 40 kDa and 20 kDa including the 120 kDa, 60 kDa and 37 kDa bands. More bands were detected in sample A due to the contaminated proteins from FCS. The intensity of the protein bands of TRRE should correlate with TRRE activity. Thus, the 60 kDa and 37 kDa bands were the strongest candidates as TRRE because of their corresponding increase in intensity with higher levels of TRRE. The 37 kDa band appeared to correlate better with TRRE than the 60 kDa band.

Two types of enzyme sources of TRRE were prepared for its purification. First, in sample A, TRRE was induced to high levels from PMA-stimulated THP-1 cells in 1% FCS-contained medium without PMA. This was a good source of TRRE, but high protein contamination from FCS was observed. In the second source, named sample B, TRRE was induced much less than sample A from THP-1 cells in PMA-contained medium without FCS. Here a very pure protein sample was obtained without FCS-contamination but much less TRRE activity was detected. Moreover, the recovery of TRRE activity in sample B was markedly less than sample A at every step of the purification procedure including dialysis, centrifugal concentration by a membrane-filter, DEAE column and native PAGE. Therefore, an insufficient amount of purified TRRE was isolated for AA sequencing with the procedure of sample B. However, sample B was helpful in identifying the possible TRRE band at the final step of SDS-PAGE due to its purity. Thus, after a potential band in the SDS-PAGE was identified from the more pure sample B, sample A was utilized to prepare enough of purified TRRE for AA sequencing.

In DEAE-Sephadex column chromatography TRRE eluted in earlier fractions than the main proteins, most of which considered as BSA. Since DEAE-Sephadex also has a gel-filtration effect in addition to an anion-exchange effect, the molecular size of TRRE may be larger than BSA whose molecular size is about 69 kDa. However, the finding that the molecular sizes of possible TRRE candidates at the final purification step were 37 kDa and 60 kDa may also support data presented herein indicating that TRRE exists as a complex formed with sTNF-R and TNF, as TRRE displayed the ability to combine with sTNF-R in Chapter III. Another possibility is that TRRE may exist as a homo or hetero oligomer presumably consisting of 37 kDa and/or 60 kDa monomer.

In this Example, TRRE was shown to easily lose its activity through every purification step especially at low protein and salt concentrations. We have performed several other purification procedures in addition to those described in this Example. For example, TRRE sample was subjected to C4 reverse-phase high-performance liquid chromatography (HPLC) in the 5 to 95% gradient of acetonitrile with moderate resolution. TRRE activity, however, was completely inactivated in acetonitrile, although a small amount of the activity was restored after lyophilization. Fast protein liquid chromatography (FPLC) was then applied and turned out to be inappropriate for separating TRRE from major proteins or for large-scale purification. To purify TRRE specifically, we tried two kinds of affinity chromatography such as soluble p75 TNF-R affinity column mentioned in Chapter III and anti-soluble p75 TNF-R antibody affinity column by taking advantage of the ability of TRRE to make a complex form with sTNF-R. These methods were acceptable for obtaining pure TRRE but were unsuitable for handling large amounts necessary for AA sequencing. Taking all these factors into account, our present purification scheme has worked quite efficiently to recover high specific TRRE activity and was capable of handling both large amounts and volume of protein samples necessary for AA sequencing.

EXAMPLE 7

Purification of TRRE

The following protocol was used in purification of TRRE.

1. Supernatant from large scale cell culture of 10−6M PMA stimulated THP-1
   ↓
2. Ammonium sulfate precipitation
   ↓
3. DEAE-Sephadex chromatography
   ↓

4. 6% Native PAGE
↓
5. 10% SDS-PAGE
↓
6. Transfer to nitrocellulose membrane
↓
7. Trypsin digestion
↓
8. Reverse-phase HPLC C18 column
↓
9. Analysis of amino acid sequence Step 1: Large Scale Cell Culture THP-1 were cultured in 4.0 L serum containing medium until the cell density reached $1 \times 10^6$ to $1.5 \times 10^6$ cell/ml. The cells were incubated in 1% FCS containing medium with $10^{-6}$M PMA (phorbol 12-myristate 13-acetate) (Sigma Chemical, St. Louis, Mo.) for 30 min. After washing in serum free medium, the cells were incubated for additional 2 hours in 4 L 1% FCS containing medium without PMA and the supernatant was collected as the source of the enzyme.

Step 2: Ammonium Sulfate Precipitation

The supernatant was concentrated by the 100% saturated ammonium sulfate precipitation method described in Example 4. The precipitate was collected and redissolved in PBS and dialyzed against 10 mM Tris-HCl, 60 mM NaCl (pH 7.0) for 60 hours.

Step 3: DEAE-Sephadex Chromatography

The concentrated samples were diluted in the same volume of 50 mM Tris-HCl, 60 mM NaCl (pH 8.0) and applied onto an anion-exchange chromatography, DEAE-Sephadex A-25 (Pharmacia Biotech, Uppsala; Sweden) column. The samples were eluted with a sodium linear gradient (60 mM to 250 mM NaCl). Several fractions with the highest specific TRRE activity were collected.

Step 4: Native PAGE

The active DEAE fractions were centrifugally concentrated to 500 μl with a Centriprep-10 filter (10,000 MW cut-off membrane) (Amicon). This concentrated sample was applied to 6% PAGE under non-denaturing native conditions. The gel was sliced horizontally into 5 mm strips and each was eluted into 1 ml PBS. Each TRRE active fraction was centrifugally concentrated to 50 μl with a Centriprep-10 filter.

Step 5: SDS-PAGE and Protein Blotting

The concentrated active samples eluted from native PAGE were loaded on 10% SDS-PAGE. The proteins were then electrophoretically transferred to nitrocellulose membrane and stained with 0.1% Ponceau S.

Step 6: Preparation of Peptide Fragments for Microsequencing

Each band was cut out from the nitrocellulose membrane and digested with 1 μg trypsin (Boehringer) in digestion buffer (0.1 M Tris-HCl pH 8.0, 1 mM $CaCl_2$, 10%(v/v) acetonitorile) overnight.

The digested samples were spun down and the supernatants were injected onto reverse phase HPLC $C_{18}$ column (4.6×250 mm). The peptide fragments were eluted with a linear gradient of 0–60% acetonitrile containing 0.1% trifluoroacetic acid. Several peak fractions were collected and subjected to amino acid sequence analysis using an Applied Biosystems, Inc. peptide sequencer.

Candidates of the TRRE

SDS-PAGE of concentrated active eluates from the native PAGE revealed several protein bands. The TRRE eluate with highest activity had protein bands at approximate 120 kDa, 60 kDa, and 37 kDa. The 60 kDa and 37 kDa bands were the strongest candidates as TRRE because of their corresponding increase in intensity with higher levels of TRRE activity. Thus, at first the 60 kDa band (p60) of blotting membrane stained with 0.1% Ponceau S were cut out and subjected to further analysis.

EXAMPLE 8

Use of TRRE in Treating Septic Shock

The following protocol was followed to test the effects of TRRE in preventing mortality in test animals which were treated with lipopolysaccharides (LPS) to induce sepsis and septic shock.

Generally, mice were injected with lethal or sublethal levels of LPS, and then with a control buffer or TRRE. Samples of peripheral blood were then collected at intervals to establish if TRRE blocked TNF-induced production of other cytokines in the bloodstream. Animals were assessed grossly for the ability of TRRE to block the clinical effects of shock and then euthanized and tissues examined by histopathological methods.

More specifically, adult Balb/c mice, the traditional animal model for septic shock studies [see, for example, Mack et al. (1997) *J. Surg. Res.* 69:399–407; and Seljelid et al. (1997) *Scand. J. Immunol.* 45:683–7], were placed in a restraining device and injected intravenously via the tail vein with a 0.1 ml solution containing 10 ng to 10 mg of LPS in phosphate buffer saline (PBS). These levels of LPS induce mild to lethal levels of shock in this strain of mice. Shock results from changes in vascular permeability, fluid loss, and dehydration, and is often accompanied by symptoms including lethargy, a hunched, stationary position, rumpled fur, cessation of eating, cyanosis, and, in serious cases, death within 12 to 24 hours. Control mice received an injection of PBS. Different amounts (2,000 or 4,000 U) of purified human TRRE were injected IV in a 0.1 ml volume within an hour prior to or after LPS injection. Serum (0.1 ml) was collected with a 27 gauge needle and 1 ml syringe IV from the tail vein at 30, 60 and 90 minutes after LPS injection. This serum was heparinized and stored frozen at −20° C. Samples from multiple experiments were tested by ELISA for the presence of sTNF-R, TNF, IL-8 and IL-6. Animals were monitored over the next 12 hours for the clinical effects of shock. Selected animals were euthanized at periods from 3 to 12 hours after treatment, autopsied and various organs and tissues fixed in formalin, imbedded in paraffin, sectioned and stained by hematoxalin-eosin (H and E). Tissue sections were subjected to histopathologic and immunopathologic examination.

Figure 19:
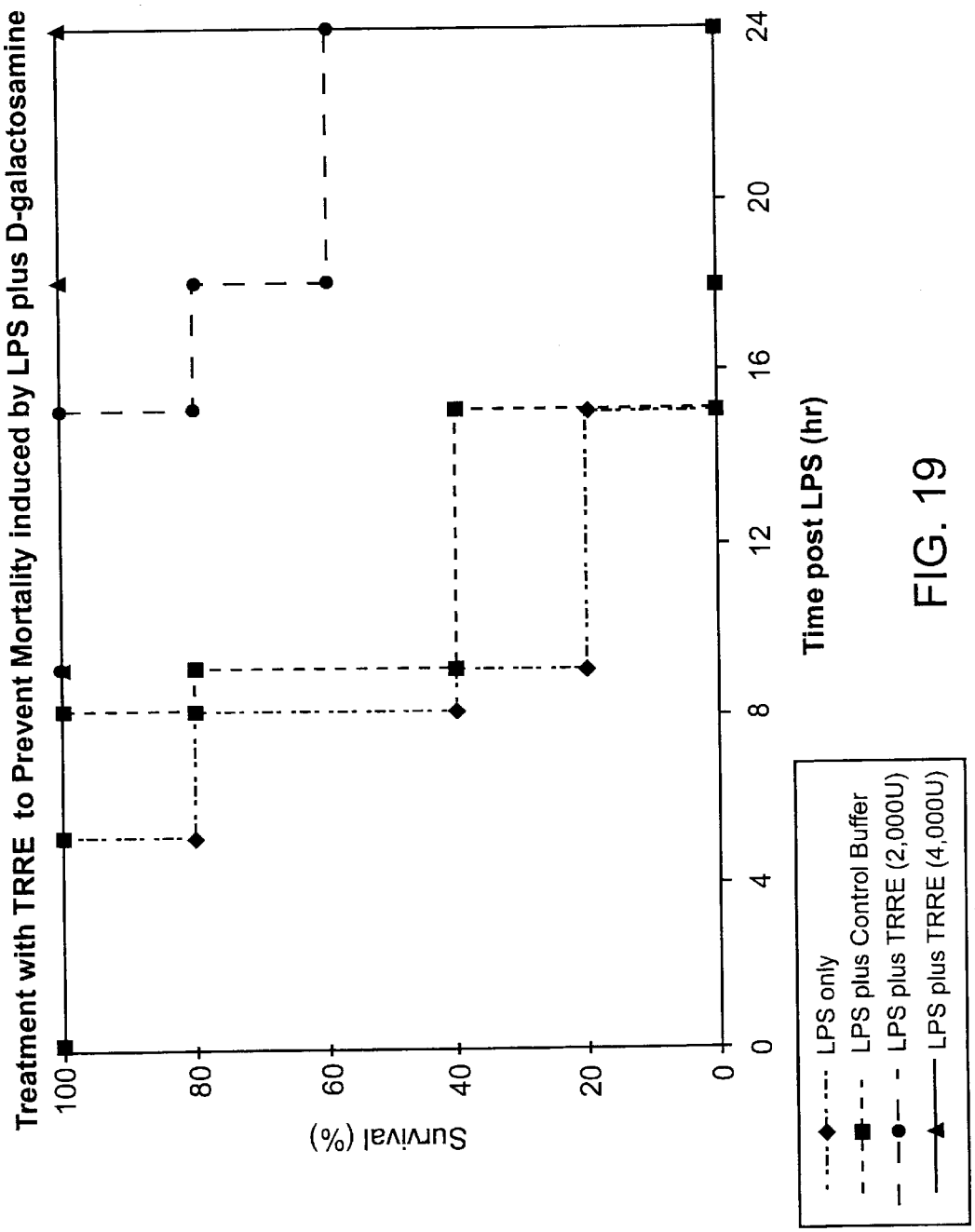
FIG. 19 is a graph depicting the effect of TRRE on preventing mortality in mice treated with lipopolysaccharide (LPS) to induce septic peritonitis.

As shown in FIG. 19, mice injected with LPS alone or LPS and a control buffer demonstrated rapid mortality. 50% of the test animals were dead after 8 hours (LPS) or 9 hours (LPS plus control buffer), and 100% of the animals were dead at 15 hours. In contrast, when injections of LPS were accompanied by injections of a 2,000 U of TRRE, death was delayed and death rates were lower. Only 40% of the animals were dead at 24 hours. When 4,000 U of TRRE was injected along with LPS, all of the animals had survived at 24 hours. Thus, TRRE is able to counteract the mortality induced by LPS in test animals.

EXAMPLE 9

Effect of TRRE on the Necrotizing Activity of Human TNF In vivo

The following protocol was followed to test the effects of TRRE in affecting tumor necrosis in test animals in which tumors were produced, and in which TNF was subsequently injected.

Generally, on Day 0, cutaneous Meth A tumors were produced on the abdominal wall of fifteen BALB/c mice by intradermal injection of 2×20$^5$ Meth A tumor cells.

On Day 7, the mice were divided into three groups of five mice each and treated as follows:

Group 1: Injected intravenously with TNF (1 µg/mouse).

Group 2: Injected intravenously with TNF (1 µg/mouse) and injected intratumorally with TRRE (400 units/mouse, 6, 12 hours after TNF injection).

Group 3: Injected intravenously with TNF (1 µg/mouse) and injected intratumorally with control medium (6, 12 hours after TNF injection).

On Day 8, tumor necrosis was measured with the following results:

% of Necrosis

Group 1: 100 (5/5)
Group 2: 20 (1/5)
Group 3: 80 (4/5)

Therefore, injections of TRRE greatly reduced the ability of TNF to induce necrosis in Meth A tumors in BALB/c mice.

Although the foregoing invention has been described in some detail by way of illustration and example for purposes of clarity and understanding, it will be apparent to those skilled in the art that certain changes and modifications can be practiced. Therefore, the description and examples should not be construed as limiting the scope of the invention which is delineated by the appended claims.

What is claimed is:

1. An isolated composition comprising a TNF receptor releasing enzyme, obtainable by a process comprising:
   a) stimulating THP-1 cells with phorbol myristate acetate;
   b) harvesting culture medium from the stimulated cells; and
   c) isolating the enzyme from the harvested medium;
   wherein the enzyme causes cleaving and release of TNF receptor expressed on a cell surface.

2. The composition of claim 1, isolated by a method comprising ion exchange chromatography and separation by molecular weight.

3. The composition of claim 1, obtained by separating a polypeptide having an apparent molecular weight by SDS polyacrylamide gel electrophoresis of about 120,000.

4. The composition of claim 3, which is at least about 95% homogeneous when analyzed by SDS polyacrylamide gel electrophoresis.

5. The composition of claim 1, obtained by separating a polypeptide having an apparent molecular weight by SDS polyacrylamide gel electrophoresis of about 60,000.

6. The enzyme composition of claim 5, which is at least about 95% homogeneous when analyzed by SDS polyacrylamide gel electrophoresis.

7. The composition of claim 1, obtained by separating a polypeptide having an apparent molecular weight by SDS polyacrylamide gel electrophoresis of about 37,000.

8. The composition of claim 7, which is at least about 95% homogeneous when analyzed by SDS polyacrylamide gel electrophoresis.

9. The composition of claim 1, having enzymatic activity that is inhibitable by a metalloprotease inhibitor but not by a serine protease inhibitor or a cysteine protease inhibitor.

10. The composition of claim 1, having enzymatic activity that is enhanced in the presence of $Ca^{++}$ and is diminished in the presence of phenanthroline.

11. A method of obtaining the composition of claim 1, comprising:
    a) culturing a cell expressing an enzyme that causes cleaving and release of TNF receptor expressed on a cell surface, said culturing being under conditions to cause the release of TNF receptor releasing enzyme activity into the medium;
    b) harvesting medium from the cultured cell; and,
    c) isolating the composition from the culture medium.

12. The method of claim 11, wherein the isolating comprises ion exchange chromatography and separation by molecular weight.

13. The method of claim 11, wherein the composition has been obtained from THP-1, U-937, HL-60, ME-180, MRC-5, Raji, or K-562 cells or normal human monocytes.

14. A method for decreasing signal transduction from TNF into a cell, comprising contacting the cell with the composition of claim 1, under conditions where the composition causes cleaving and release of TNF receptors from the cell surface.

15. The composition of claim 1, which is obtainable from the supernatant of cultured THP-1 cells upon induction with PMA, without de novo protein synthesis.

16. The composition of claim 1, which is obtainable from the supernatant of cultured THP-1 cells upon induction by IL-10 or epinephrine.

17. The composition of claim 1, which causes cleaving and release of the human p75 TNF receptor.

18. The composition of claim 1, which causes cleaving and release of the human p55 TNF receptor.

19. The composition of claim 1, which has an apparent molecular weight of 66–200 kDa as determined by gel filtration chromatography on Sephadex G-150 at pH 7.0.

20. The composition of claim 1, which has an apparent molecular weight of about 150 kDa as determined by gel filtration chromatography on Sephadex G-150 at pH 7.0.

21. The composition of claim 1, which migrates as a single band when subject to polyacrylamide gel electrophoresis in non-denaturing conditions.

22. The composition of claim 1, which is at least 80% pure (wt/wt protein).

23. The composition of claim 1, wherein TNF receptor releasing activity as measured by cleavage of p75 TNF receptor from isolated cells is at least 5,000 U/mL.

24. The composition of claim 1, wherein TNF receptor releasing activity as measured by cleavage of p75 TNF receptor from isolated cells is at least 15,000 U/mL.

25. The composition of claim 1, wherein TNF receptor releasing activity as measured by cleavage of p75 TNF receptor from isolated cells is at least 40,000 U/mL.

26. The composition of claim 1, obtained according to the method of claim 11.

27. The method of claim 14, wherein the composition has been obtained according to the method of claim 11.

28. The method of claim 14, wherein the composition has been obtained from THP-1 cells.

* * * * *